United States Patent
Urano et al.

(10) Patent No.: US 11,655,269 B2
(45) Date of Patent: May 23, 2023

(54) PRODRUG-TYPE ANTICANCER AGENT USING CANCER-SPECIFIC ENZYMATIC ACTIVITY

(71) Applicant: The University of Tokyo, Tokyo (JP)

(72) Inventors: Yasuteru Urano, Tokyo (JP); Mako Kamiya, Tokyo (JP); Kento Hayashi, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 16/977,607

(22) PCT Filed: Mar. 4, 2019

(86) PCT No.: PCT/JP2019/008483
§ 371 (c)(1),
(2) Date: Sep. 2, 2020

(87) PCT Pub. No.: WO2019/172210
PCT Pub. Date: Sep. 12, 2019

(65) Prior Publication Data
US 2020/0399305 A1    Dec. 24, 2020

Related U.S. Application Data

(60) Provisional application No. 62/638,075, filed on Mar. 3, 2018.

(51) Int. Cl.
| | | |
|---|---|---|
| C07H 23/00 | (2006.01) | |
| A61P 35/00 | (2006.01) | |
| C07C 237/04 | (2006.01) | |
| C07D 207/16 | (2006.01) | |
| C07F 7/08 | (2006.01) | |
| C07H 15/203 | (2006.01) | |

(52) U.S. Cl.
CPC .............. *C07H 23/00* (2013.01); *A61P 35/00* (2018.01); *C07C 237/04* (2013.01); *C07D 207/16* (2013.01); *C07F 7/081* (2013.01); *C07F 7/0812* (2013.01); *C07H 15/203* (2013.01)

(58) Field of Classification Search
CPC ... C07K 5/06026; A61P 35/00; C07C 237/04; C07C 271/22
See application file for complete search history.

(56) References Cited

U.S. PATENT DOCUMENTS

| | | | | |
|---|---|---|---|---|
| 8,067,411 B2 * | 11/2011 | Bonnert | .............. | A61P 25/00 514/263.37 |
| 2016/0324983 A1 | 11/2016 | Li | | |
| 2017/0364744 A1 | 12/2017 | Savchenkov et al. | | |
| 2020/0190101 A1 | 6/2020 | Niitsuma et al. | | |

FOREIGN PATENT DOCUMENTS

| | | |
|---|---|---|
| CN | 102603695 | 7/2012 |
| CN | 106831904 | 6/2017 |
| EP | 3 378 495 | 9/2018 |
| JP | 2017-502068 | 1/2017 |
| WO | 2015/178265 | 11/2015 |
| WO | 2017/086392 | 5/2017 |

OTHER PUBLICATIONS

Hai et al., "Bioluminescence sensing of γ-glutamyltranspeptidase activity in vitro and in vivo", *Anal. Chem.*, vol. 89, No. 13, pp. 7017-7021 (2017).
Souza et al., "Brazoides A-D, new alkaloids from *Justicia gendarussa* Burm. F. species", *J. Braz. Chem. Soc.*, vol. 28, No. 7, pp. 1281-1287 (2017).
Keillor et al., "Pre-steady-state kinetic studies of rat kidney γ-glutamyl transpeptidase confirms its ping-pong mechanism", *J. Phys. Org. Chem.*, vol. 17, No. 67, pp. 529-536 (2004).
Extended European Search Report issued in EP Patent App. No. 19764794.4, dated Nov. 10, 2021.
Carl et al., "A novel connector linkage applicable in prodrug design", *Journal of Medicinal Chemistry*, vol. 24, No. 5, pp. 479-480(1981).
Hsu et al., "Development of activity-based probes for imaging human α-L-fucosidases in cells", *Journal of Organic Chemistry*, vol. 80, No. 16, pp. 8458-8463 (2015).
Halazy et al., "Ortho- and para-(difluoromethyl)aryl-β-D-glucosides: a new class of enzyme-activated irreversible inhibitors of β-glucosidases", *Bioorganic Chemistry*, vol. 18, No. 3, pp. 330-344 (1990).
Ichikawa et al., "A mechanism-based affinity-labeling agent for possible use in isolating N-acetylglucosaminidase", *Bioorganic & Medicinal Chemistry Letters*, vol. 11, No. 13, pp. 1769-1773 (2001).
Lo et al., "Synthesis of activity probes for β-xylosidase", *Journal of the Chinese Chemical Society* (Taipei, Taiwan), vol. 53, No. 2, pp. 479-488 (2006).
Polaske et al., "Quinone methide signal amplification: covalent reporter labeling of cancer epitopes using alkaline phosphatase substrates", *Bioconjugate Chemistry*, vol. 27, No. 3, pp. 660-666 (2016).
Shi et al., "Identification of novel kinase inhibitors by targeting a kinase-related apoptotic protein-protein interaction network in HeLa cells", *Cell Proliferation*, vol. 47, No. 3, pp. 219-230 (2014).
International Search Report issued in PCT/JP2019/008483, dated May 21, 2019, along with an English language translation.

* cited by examiner

*Primary Examiner* — Pancham Bakshi

(74) *Attorney, Agent, or Firm* — Greenblum & Bernstein, P.L.C.

(57) ABSTRACT

To provide novel compounds that are promising as prodrug-type anticancer agents, a compound represented by general formula (I) or a salt thereof is provided.

(I)

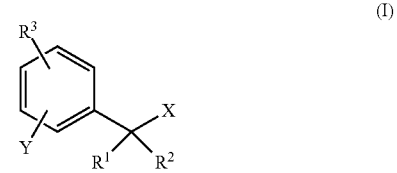

4 Claims, 16 Drawing Sheets

[FIG. 1]
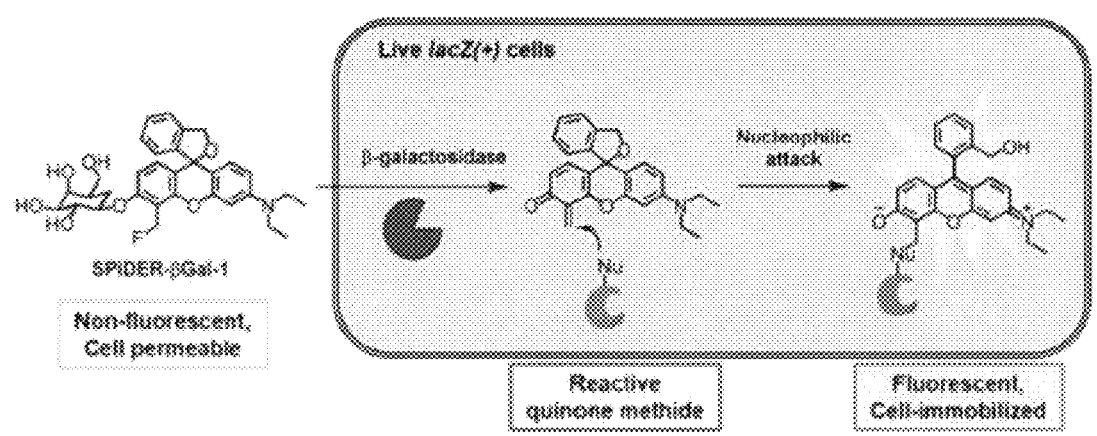
[FIG. 2]
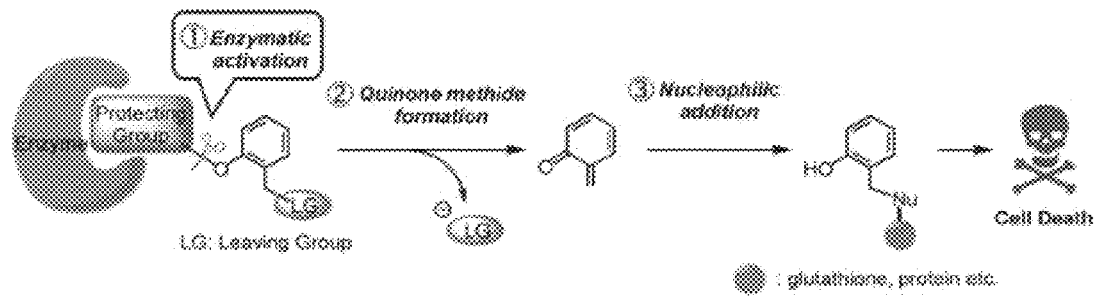

[FIG. 3]
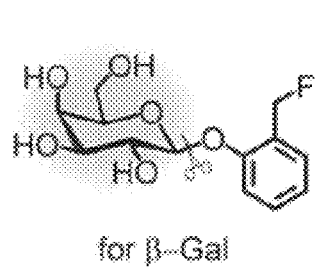
for β-Gal
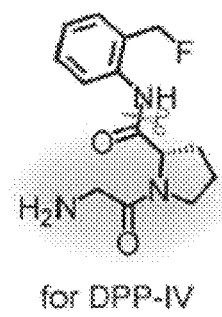
for DPP-IV
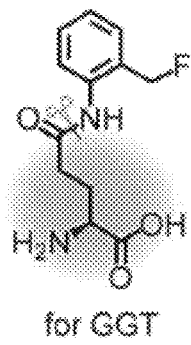
for GGT

[FIG. 4]
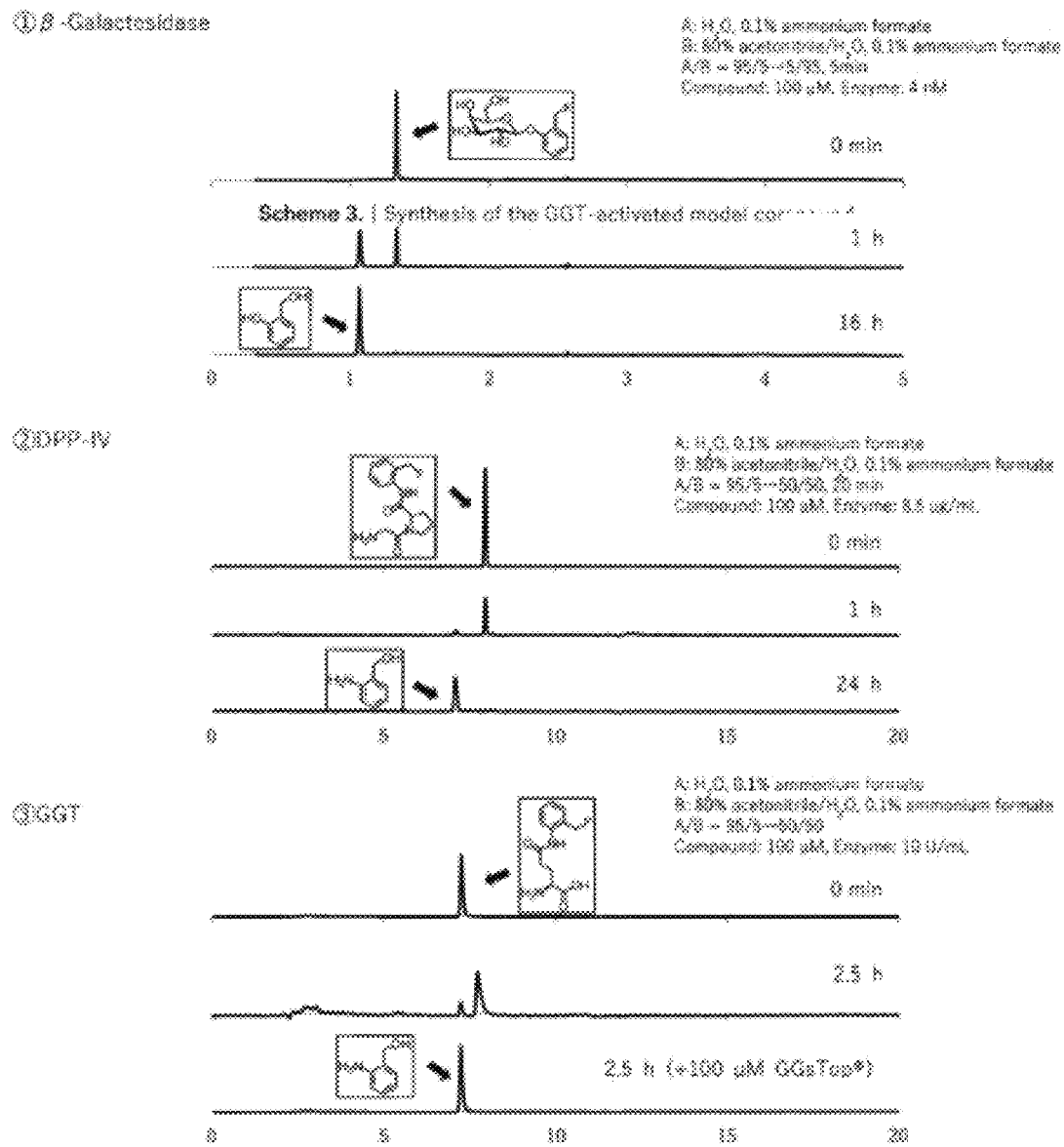

[FIG. 5]
① β-Galactosidase
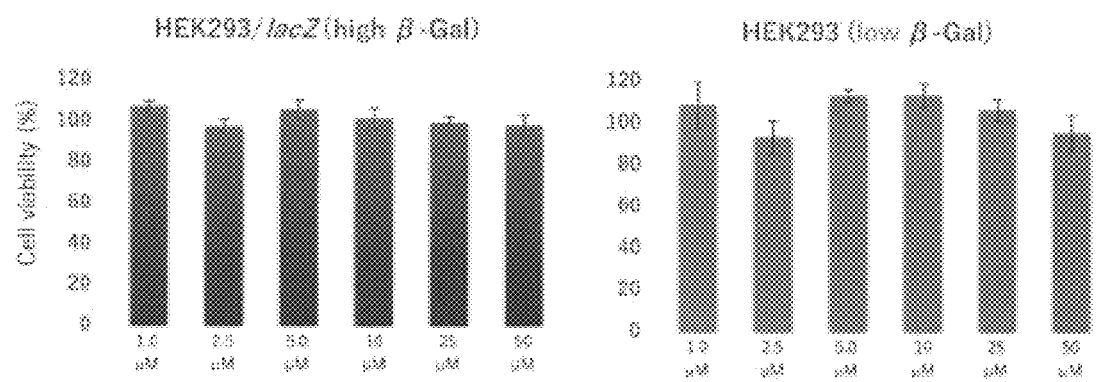
[FIG. 6]
② DPP-IV
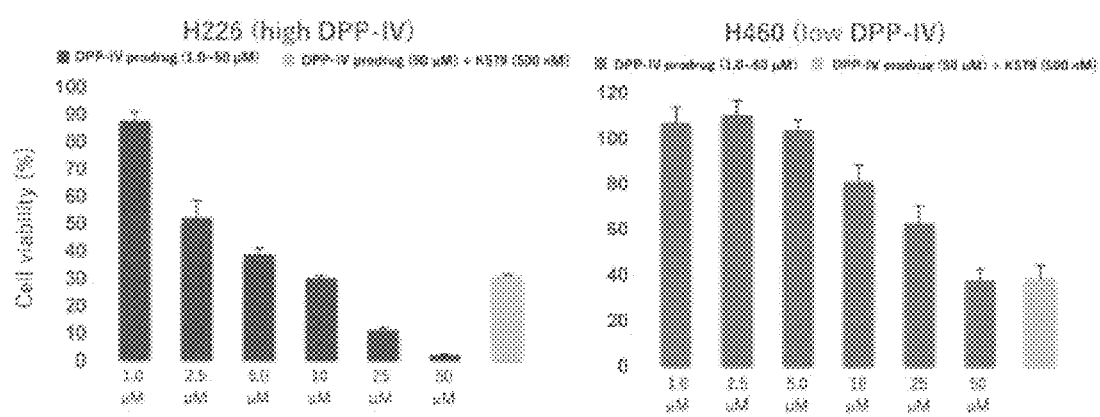

[FIG. 7]
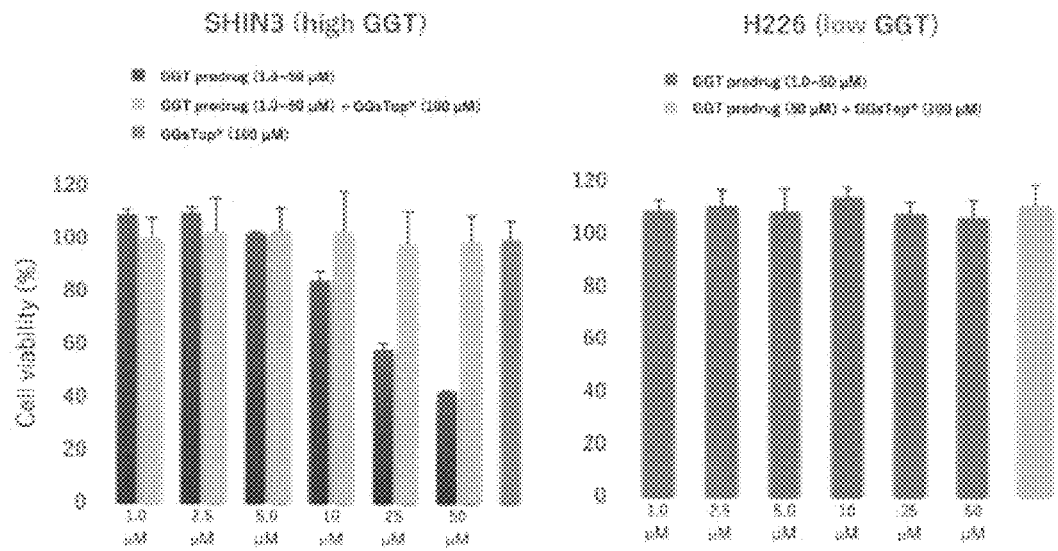
[FIG. 8]
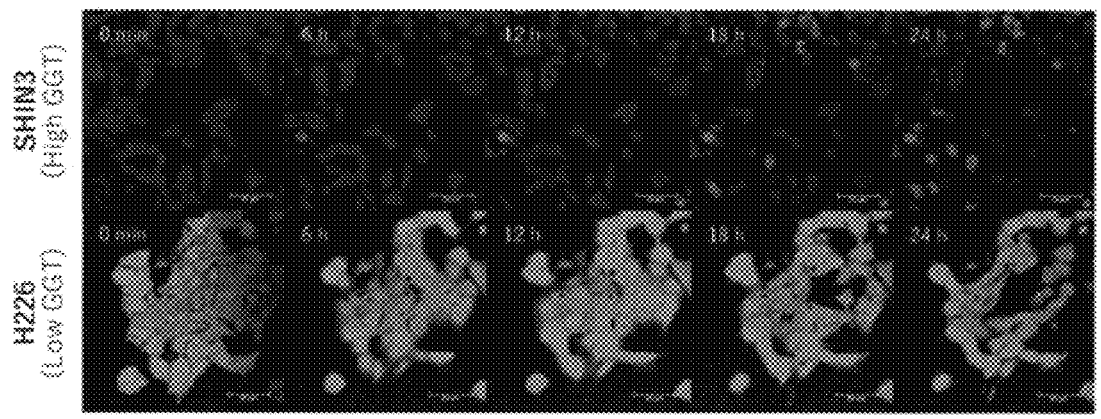
Time-lapse fluorescence imaging of SHIN3 cells (top) and H226 cells (bottom) with GGT model compound and EthD-1 (dead cell staining, Ex/Em = 525 nm/511-564 nm), Lens 63x/1.4 Oil, Scan mode: xyzt, x = 512, y = 512, z = 4, t = 24. Scale bars, 50 μm.

[FIG. 9]
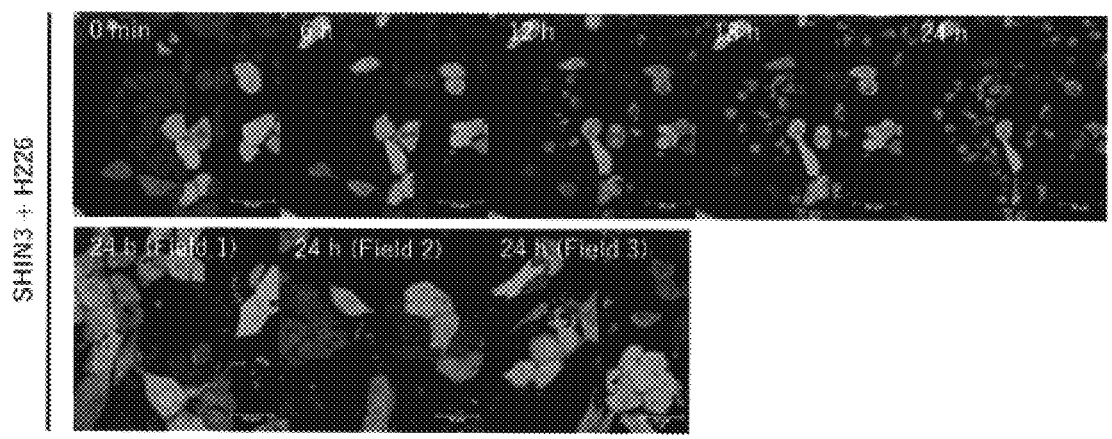
Time-lapse fluorescence imaging of cocultured cells (SHIN3 cells: Blue, H226 cells: Green) with GGT model compound and EthD-1 (dead cell staining, Ex/Em = 525nm/511-564 nm) (top). Confocal imaging of cells in other 3 fields after 24 h imaging (bottom). Lens 63x/1.4 Oil. Scan mode: xyzt, x = 512, y = 512, z = 4, t = 24. Scale bars, 50 μm.

[FIG. 10]
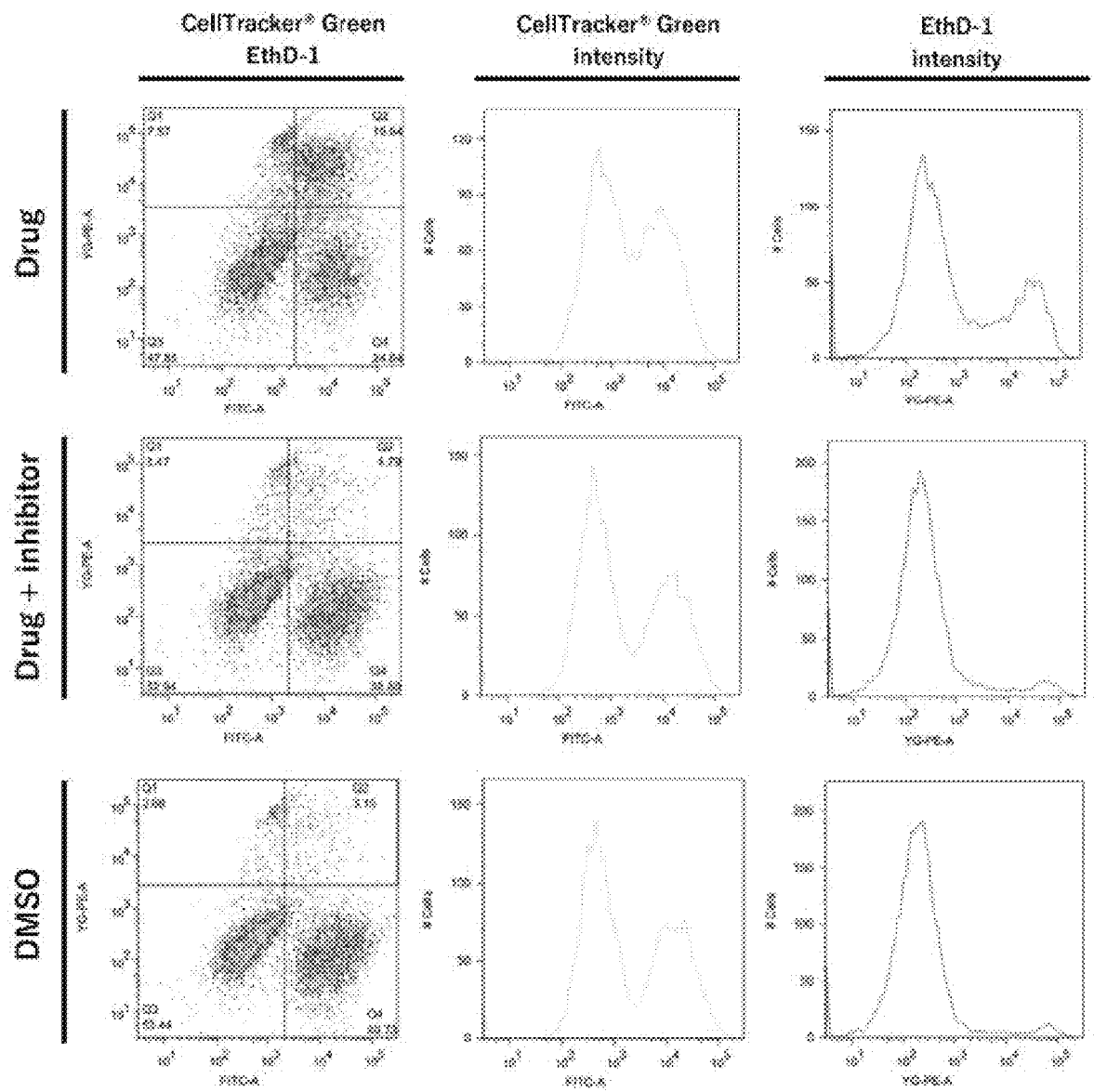
Flow cytometry analysis of cell proliferation in SHIN3 cell (Green) and H226 cell (not stained) with GGT-activated model compound. (top) 25 µM model compound, (middle) 25 µM model compound + 100 µM GGsTop, (bottom) 0.25%DMSO control. Analysis have done after 24 h incubation.

[FIG. 11]
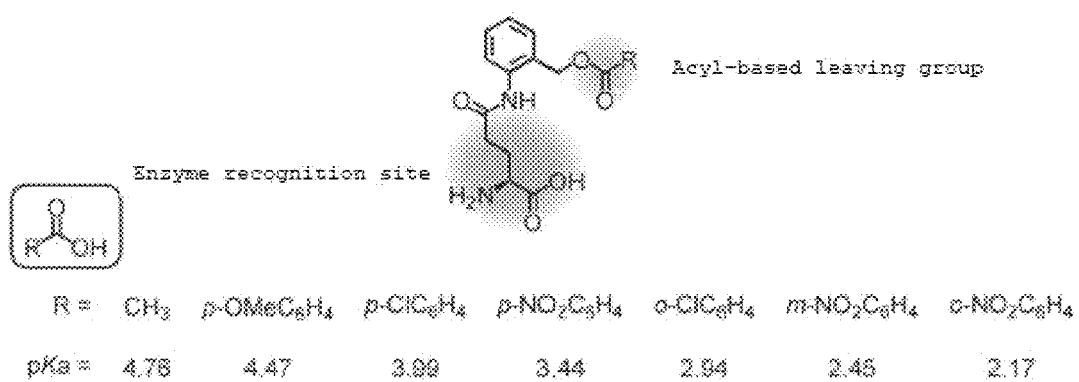

[FIG. 12]
Confirmation of enzyme recognition capacity using benzyl-position leaving group-converted derivatives
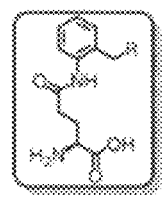
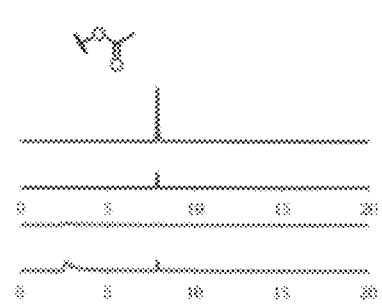
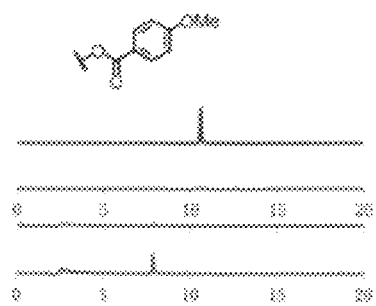
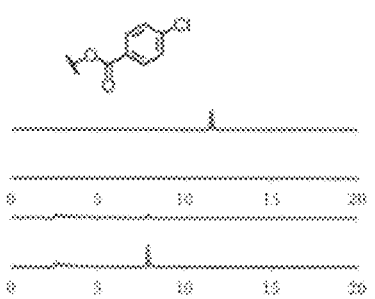
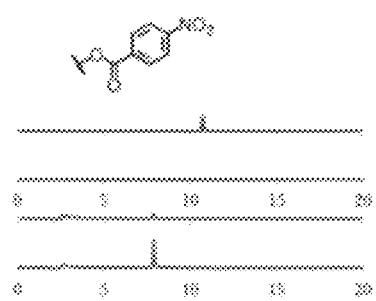
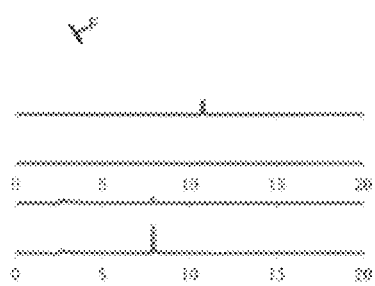
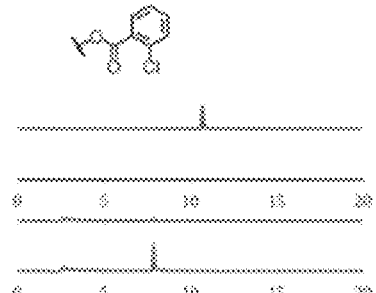
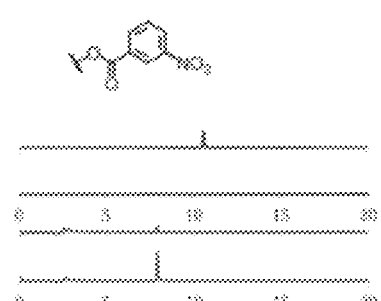
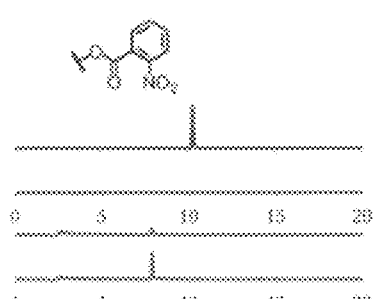

[FIG. 13]
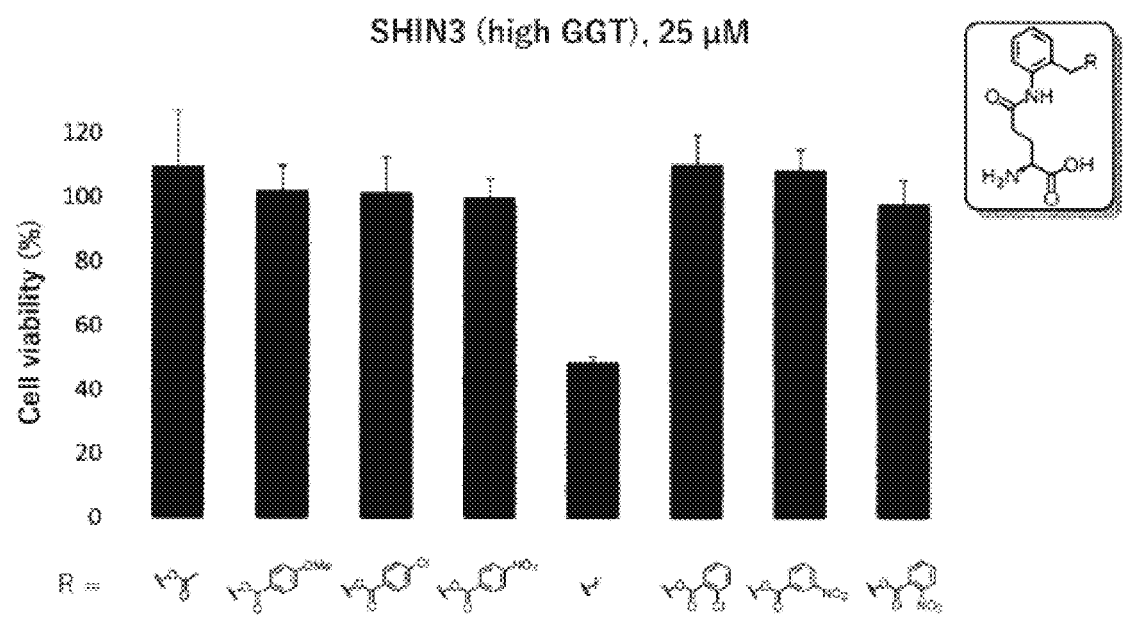

[FIG. 14]
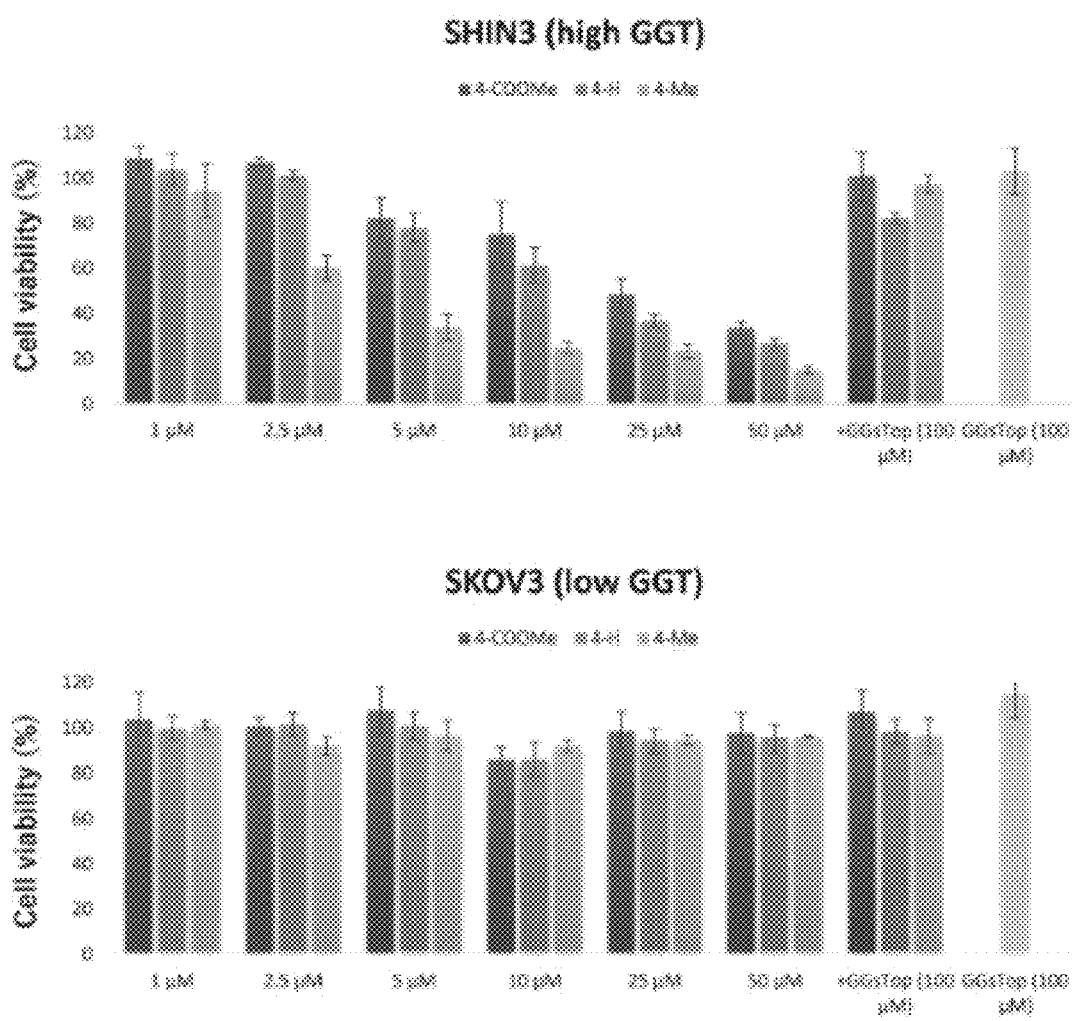

[FIG. 15]
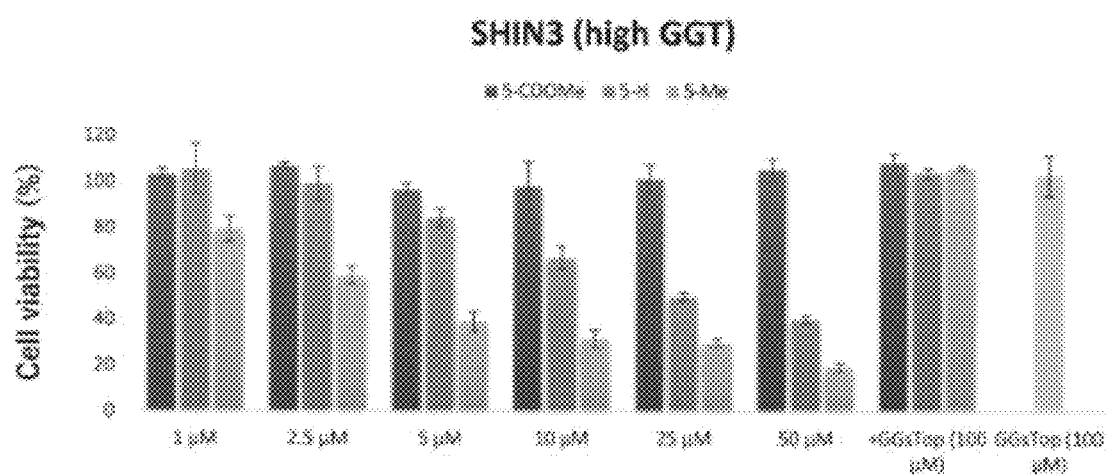
Figure 16. | Effects of 5-substituted GGT prodrug derivatives on cell proliferation (n =3).
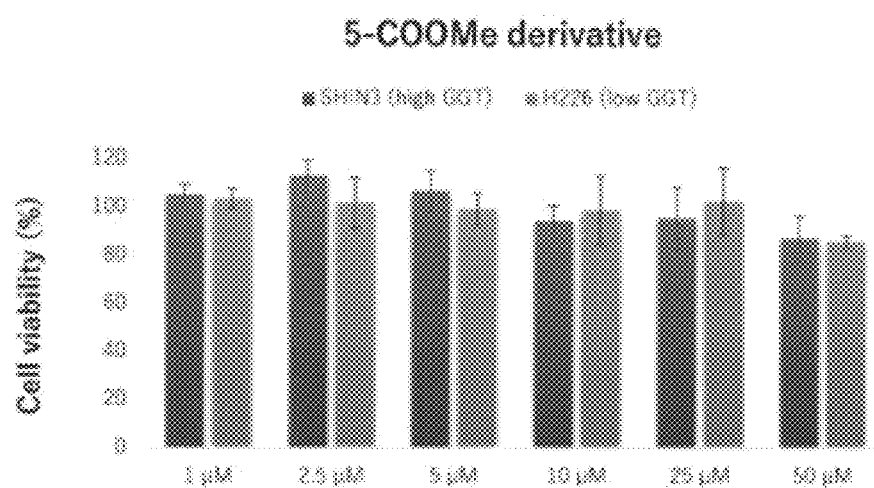

[FIG. 16]
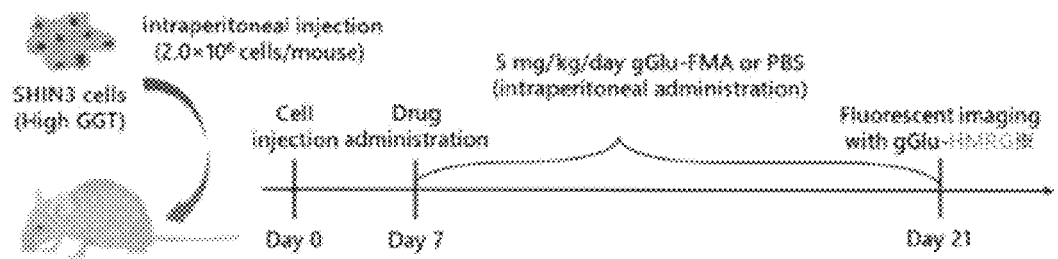
※Fluorescent imaging was obtained 10 min after intraperitoneal administration of gGlu-HMRG.
Tumor quantification was performed by integrating total green fluorescence in images.
[FIG. 17]
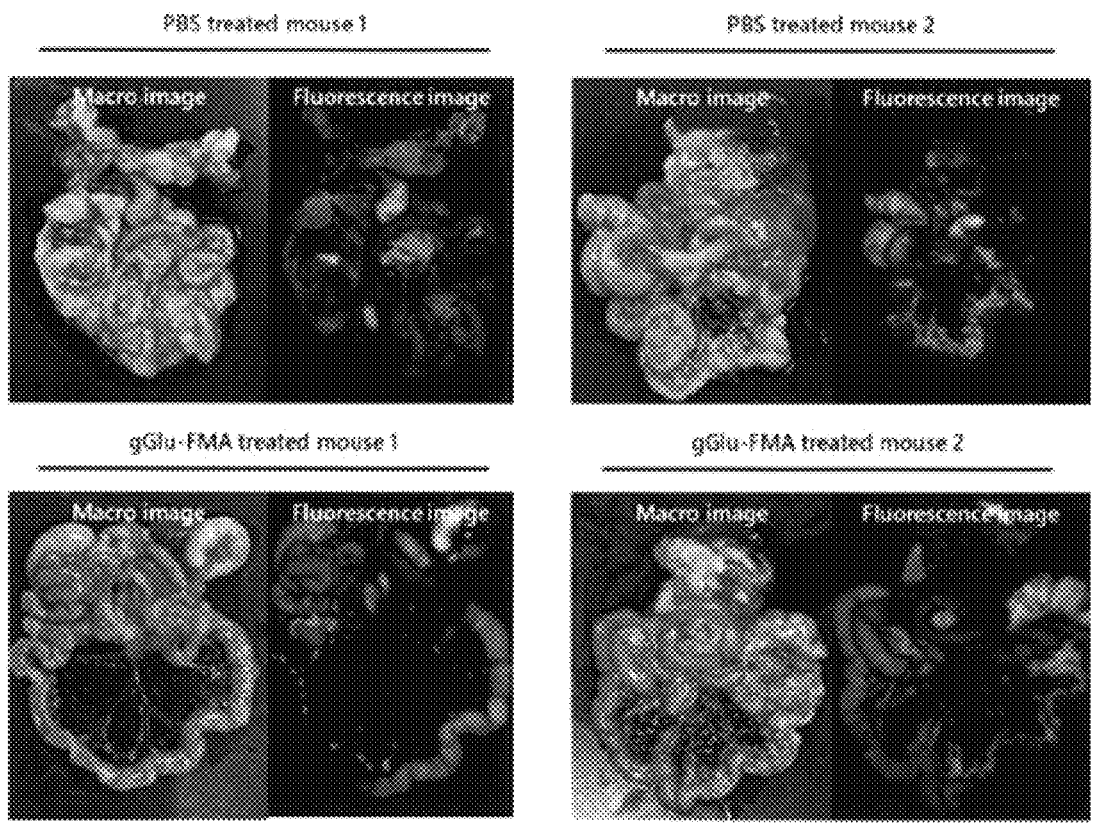

[FIG. 18]
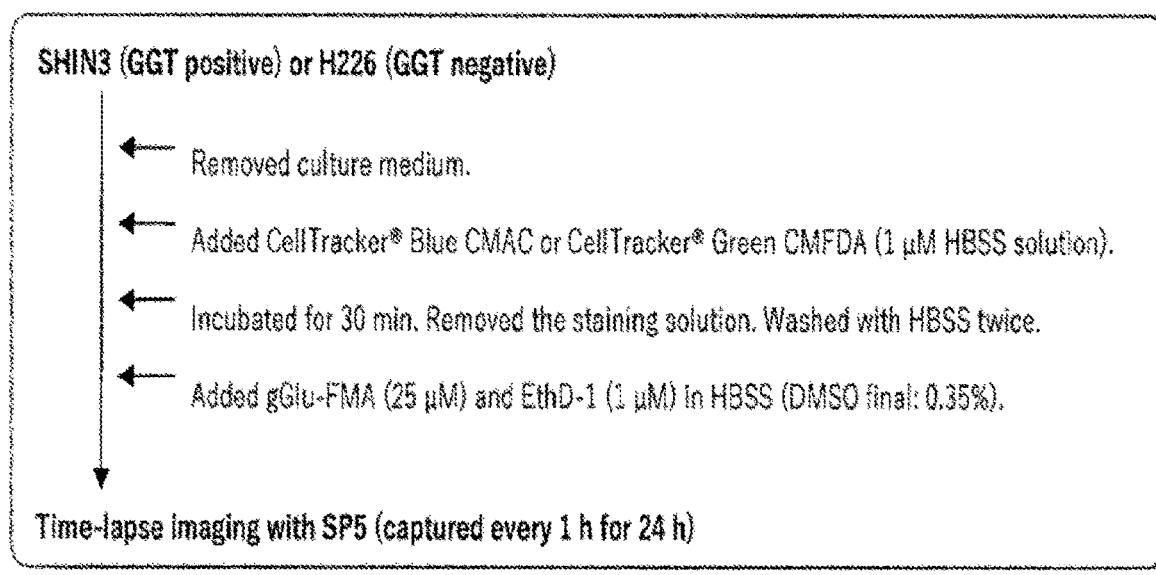

[FIG. 19]
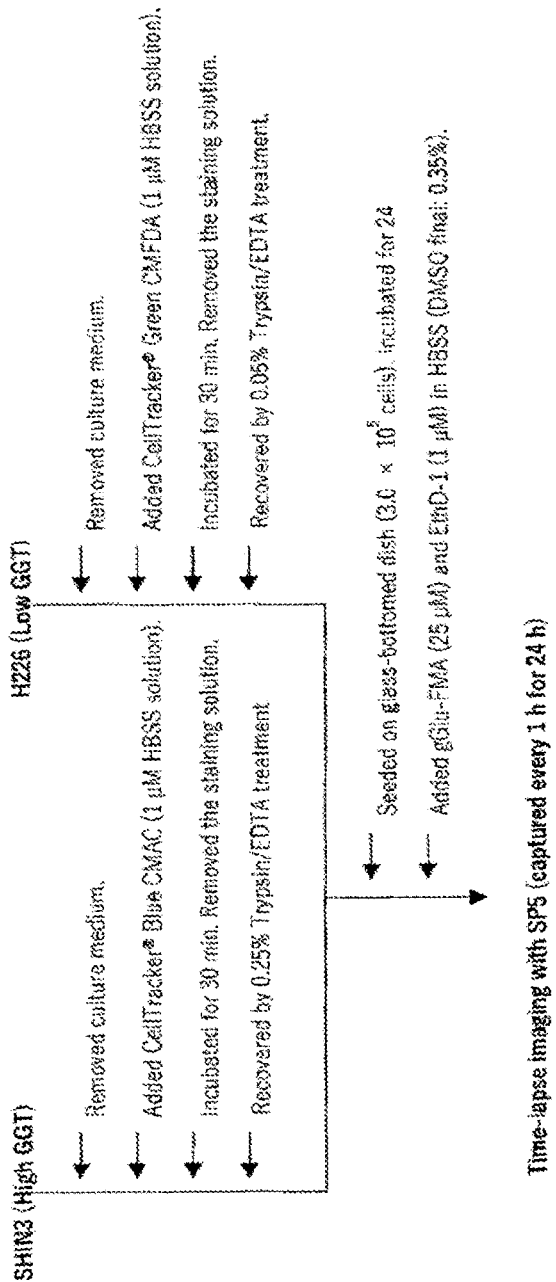

[FIG. 20]

SHIN3 (High GGT) or H226 (Low GGT)
- Removed culture medium.
- Added CellTracker® Green CMFDA (1 µM HBSS solution, stained only SHIN3 cell).
- Incubated for 30 min. Removed the staining solution. Washed with HBSS twice.
- Added gGlu-FMA (25 µM) in RPMI-1640. Incubated 24 h.
- Added EthD-1 (1 µM) and incubated 30 min. Treated with 0.25% Trypsin/EDTA (1 mL).
- Recovered with RPMI-1640 (2 mL × 2). Centrifuged and removed solution.
- Suspended with HBSS (1 mL).

Flowcytometry analysis

PRODRUG-TYPE ANTICANCER AGENT USING CANCER-SPECIFIC ENZYMATIC ACTIVITY

TECHNICAL FIELD

The present invention relates to novel compounds that are promising as prodrug-type anticancer agents and to a prodrug-type anticancer agent and a pharmaceutical composition that uses said compounds.

BACKGROUND ART

Given that the tissue/cell/target selection system of an anticancer agent is still never satisfactory in cancer chemotherapy, which plays an important role in cancer treatment, manifestation of efficacy is constantly associated with the simultaneous risk of serious side effects.

Creating a prodrug is known as one technique for releasing these anticancer agents specifically in cancer cells. Creating a prodrug is an approach that subjects a drug to structural modification so that the drug changes into the active form (anticancer agent) for the first time due to an enzymatic reaction or chemical reaction within the cancer cells. On the other hand, the fact that it is difficult to identify enzymes that are specifically enhanced in cancer cells and that structural modification of existing anticancer agents, which have complex structures, is not easy can be cited as problems.

SUMMARY OF THE INVENTION

Problems to be Solved by the Invention

A purpose of the present invention is to provide novel compounds that are promising as prodrug-type anticancer agents.

Means Used to Solve the Above-Mentioned Problems

In the laboratory of the present inventors, research has been conducted into establishing a search-based technology capable of evaluating metabolic reaction characteristics characteristic of a disease site comprehensively and noninvasively on fresh clinical specimens, and the present inventors thought that it might be possible to develop highly specific therapeutic drugs efficiently by a prodrug approach through utilizing useful information relating to the metabolic reactivity of disease sites obtained directly from human clinical specimens to date.

The research group of the present inventors also developed a SPiDER probe that emits fluorescence by an enzymatic reaction and prevents leakage from cells by being tagged to intracellular thiols based on ideas based on quinone methides chemistry (FIG. 1).

Here, it became clear when the present inventors were conducting live-cell application experiments of this probe that pronounced cytotoxicity is seen when the probe is used in high concentrations. Although the mechanism of toxicity has not been clarified, it is thought that intracellular thiols such as glutathione are consumed by the quinone methide intermediate produced in association with the enzymatic reaction, causing oxidative stress on the cells.

Therefore, the present inventors conceived that it might be possible to utilize the above phenomenon and cause serious damage cell-selectively through cancer cell-specific enzyme activity and perfected the present invention as a result of developing novel prodrug-type anticancer agents.

Specifically, the present invention provides:

[1] A compound represented by general formula (I) or a salt thereof.

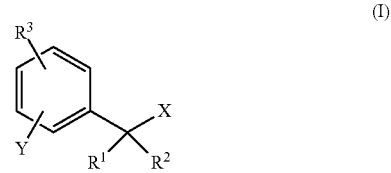

(wherein,

X is selected from the group consisting of a fluorine atom, ester group (—OC(=O)—R'), carbonate group (—OCO$_2$—R'), carbamate group (—OCONH—R'), phosphoric acid and ester groups thereof (—OP(=O)(—OR')(—OR")), and sulfuric acid and ester groups thereof (—OSO$_2$—OR'), where, R' and R" are each independently selected from substituted or unsubstituted alkyl groups or substituted or unsubstituted aryl groups;

Y is —NH—CO-L, —NH-L', or —OL', where, L is a partial structure of an amino acid, L' is a saccharide or a partial structure of a saccharide, a saccharide having a self-cleaving linker, an amino acid or a peptide having a self-cleaving linker;

$R^1$ and $R^2$ are each independently selected from a hydrogen atom or a monovalent substituent;

$R^3$ represents a hydrogen atom or one to four monovalent substituents present on a benzene ring, which are the same or different.)

[2] The compound or a salt thereof according to [1], wherein the partial structure of an amino acid of L, together with the C=O to which L bonds, constitutes an amino acid, an amino acid residue, a peptide, or part of an amino acid.

[3] The compound or a salt thereof according to [1], wherein the partial structure of a saccharide of L', together with the O to which L' bonds, constitutes a saccharide or part of a saccharide.

[4] The compound or salt thereof according to any one of [1] to [3], wherein —Y in general formula (I) bonds to —C($R^1$)($R^2$)X on the ortho position or para position of the benzene ring.

[5] The compound or salt thereof according to any one of [1] to [4], wherein Y has a structure selected from the following.

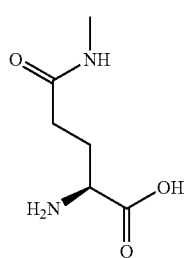

-continued

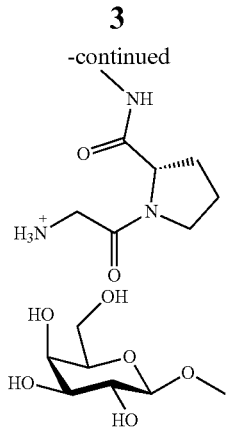

[6] The compound or salt thereof according to any one of [1] to [5], wherein X is a fluorine atom or an ester group (—OCO—R').

[7] The compound or salt thereof according to any one of [1] to [6], wherein $R^1$ and $R^2$ are each independently selected from a hydrogen atom or a fluorine atom.

[8] The compound or salt thereof according to any one of [1] to [7], wherein the monovalent substituent of $R^3$ is selected from the group consisting of an alkyl group, an alkoxycarbonyl group, a nitro group, an amino group, a hydroxyl group, an alkylamino group (—NHR', —NH-COR'), an alkoxy group (—OR', —OCOR'), a halogen atom, a boryl group, and a cyano group (R' is a substituted or unsubstituted alkyl group or a substituted or unsubstituted aryl group).

[9] The compound or salt thereof according to [8], wherein the monovalent substituent of $R^3$ is an alkyl group such as a methyl group) or an alkoxycarbonyl group such as a methoxycarbonyl group.

[10] A prodrug-type anticancer agent comprising a compound according to any one of [1] to [9] or a pharmaceutically acceptable salt thereof.

[11] A prodrug-type anticancer agent that acts cell-selectively by cancer cell-specific enzyme activity comprising a compound according to any one of [1] to [9] or a pharmaceutically acceptable salt thereof.

[12] The prodrug-type anticancer agent according to [11], wherein the enzyme is a peptidase or a glycosidase.

Advantages of the Invention

The present invention can provide novel compounds that are promising as prodrug-type anticancer agents.

BRIEF DESCRIPTION OF THE DRAWINGS

FIG. 1 Schematic diagram of the fluorescence emission of a SPIDER β-Gal probe.

FIG. 2 Schematic diagram of the expression mechanism of a novel prodrug-type anticancer agent of the present invention.

FIG. 3 Structures of quinone methides release-type prodrug compounds.

FIG. 4 Results of LC-MS analysis of products obtained by reacting compounds 1, 2, and 3 with β-Gal, DPP-IC, and GGT, respectively, in vitro.

FIG. 5 Test results of CCK-8 assay of compound 1.

FIG. 6 Test results of CCK-8 assay of compound 2.

FIG. 7 Test results of CCK-8 assay of compound 3.

FIG. 8 Study results relating to cell death observation in SHIN3 cells using compound 3.

FIG. 9 Study results relating to cell death observation under coculture conditions using compound 3.

FIG. 10 Results of flow cytometry analysis of cell proliferation in SHIN3 cells and H226 cells using compound 3.

FIG. 11 Structural formula of intermediates having an acyl-based leaving group synthesized in an example.

FIG. 12 Results that confirmed enzyme recognition capacity using a benzyl-position leaving group-converted derivatives.

FIG. 13 Results of CCK-8 assay of benzyl-position leaving group-converted derivatives.

FIG. 14 Results of CCK-8 assay of 4-substituted derivatives synthesized in an example.

FIG. 15 Results of CCK-8 assay of 5-substituted derivatives synthesized in an example.

FIG. 16 gGlu-FMA administration test summary in peritoneal dissemination model mice.

FIG. 17 Tumor imaging results on the mesentery (upper row: mice administered PBS, lower row: mice administered gGlu-FMA).

FIG. 18 Diagram of protocol 1.
FIG. 19 Diagram of protocol 2.
FIG. 20 Diagram of protocol 3.

BEST MODE FOR CARRYING OUT THE INVENTION

In the present specification, a "halogen atom" means a fluorine atom, chlorine atom, bromine atom, or iodine atom.

In the present specification, an "alkyl" may be any aliphatic hydrocarbon group having a linear, branched, or cyclic structure, or a combination thereof. The number of carbon atoms of an alkyl group is not particularly limited; for example, 1-6 carbons ($C_{1-6}$), 1-10 carbons ($C_{1-10}$), 1-15 carbons ($C_{1-15}$), 1-20 carbons ($C_{1-20}$). When a number of carbon atoms is indicated, it means an "alkyl" having a number of carbon atoms of that numerical range. For example, $C_{1-8}$ alkyls include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, etc. In the present specification, an alkyl group may have one or more arbitrary substituents. Examples of such substituents include, but are not limited to, an alkoxy group, halogen atom, amino group, mono- or di-substituted amino group, substituted silyl group, or acyl, etc. When an alkyl group has two or more substituents, the substituents may be the same or different. The same also holds for the alkyl moiety of other substituents including an alkyl moiety (e.g., an alkoxy group, arylalkyl group, etc.).

In the present specification, when certain functional groups are defined as "optionally substituted," the type of substituent, substitution position, and number of substituents are not particularly limited, and when there are two or more substituents, the substituents may be the same or different. Examples of substituents include, but are not limited to, an alkyl group, alkoxy group, hydroxyl group, carboxyl group, halogen atom, sulfo group, amino group, alkoxycarbonyl group, oxo group, etc. Further substituents may be present in these substituents. Examples thereof include, but are not limited to, a halogenated alkyl group, dialkylamino group, etc.

In the present specification, an "aryl" may be either a monocyclic or fused polycyclic aromatic hydrocarbon group and may be an aromatic heterocycle including one or more hetero atoms (e.g., an oxygen atom, nitrogen atom, or sulfur atom, etc.) as ring constituent atoms. The terms "heteroaryl" or "hetero aromatic" are sometimes also used in this case.

Nonlimiting examples of monocyclic aryls include a phenyl group (Ph), thienyl group (2- or 3-thienyl group), pyridyl group, furyl group, thiazolyl group, oxazolyl group, pyrazolyl group, 2-pyrazinyl group, pyrimidinyl group, pyrrolyl group, imidazolyl group, pyridazinyl group, 3-isothiazolyl group, 3-isoxazolyl group, 1,2,4-oxadiazol-5-yl group or 1,2,4-oxadiazol-3-yl group, etc. Nonlimiting examples of fused polycyclic aryls include a 1-naphthyl group, 2-naphthyl group, 1-indenyl group, 2-indenyl group, 2,3-dihydroinden-1-yl group, 2,3-dihydroinden-2-yl group, 2-anthryl group, indazolyl group, quinolyl group, isoquinolyl group, 1,2-dihydroisoquinolyl group, 1,2,3,4-tetrahydroisoquinolyl group, indolyl group, isoindolyl group, phthalazinyl group, quinoxalinyl group, benzofuranyl group, 2,3-dihydrobenzofuran-1-yl group, 2,3-dihydrobenzofuran-2-yl group, 2,3-dihydrobenzothiophen-1-yl group, 2,3-dihydrobenzothiophen-2-yl group, benzothiazolyl group, benzimidazolyl group, fluorenyl group, or thioxanthenyl group, etc. In the present specification, an aryl group may have one or more arbitrary substituents on its ring. Examples of these substituents include, but are not limited to, an alkoxy group, halogen atom, amino group, mono- or di-substituted amino group, substituted silyl group, or acyl, etc. When an aryl group has two or more substituents, the substituents may be the same or different. The same also holds for the aryl moiety of other substituents including an aryl moiety (e.g., an aryloxy group, arylalkyl group, etc.).

In the present specification, an "arylalkyl" represents an alkyl substituted by the above aryl. An arylalkyl may have one or more arbitrary substituents. Examples of the substituents include, but are not limited to, an alkoxy group, halogen atom, amino group, mono- or di-substituted amino group, substituted silyl group, or acyl group, etc. When an acyl group has two or more substituents, the substituents may be the same or different. Nonlimiting examples of arylalkyls include a benzyl group, 2-thienylmethyl group, 3-thienylmethyl group, 2-pyridylmethyl group, 3-pyridylmethyl group, 4-pyridylmethyl group, 2-furylmethyl group, 3-furylmethyl group, 2-thiazolylmethyl group, 4-thiazolylmethyl group, 5-thiazolylmethyl group, 2-oxazolylmethyl group, 4-oxazolylmethyl group, 5-oxazolylmethyl group, 1-pyrazolylmethyl group, 3-pyrazolylmethyl group, 4-pyrazolylmethyl group, 2-pyrazinylmethyl group, 2-pyrimidinylmethyl group, 4-pyrimidinylmethyl group, 5-pyrimidinylmethyl group, 1-pyrrolylmethyl group, 2-pyrrolylmethyl group, 3-pyrrolylmethyl group, 1-imidazolylmethyl group, 2-imidazolylmethyl group, 4-imidazolylmethyl group, 3-pyridazinylmethyl group, 4-pyridazinylmethyl group, 3-isothiazolylmethyl group, 3-isoxazolylmethyl group, 1,2,4-oxadiazol-5-ylmethyl group, or 1,2,4-oxadiazol-3-ylmethyl group, etc.

In the present specification, an "alkoxy group" is a structure in which an oxygen atom is bonded to the above alkyl group, for example, a saturated alkoxy group having a linear, branched, or cyclic structure, or a combination thereof. Suitable examples include a methoxy group, ethoxy group, n-propoxy group, isopropoxy group, cyclopropoxy group, n-butoxy group, isobutoxy group, s-butoxy group, t-butoxy group, cyclobutoxy group, cyclopropylmethoxy group, n-pentyloxy group, cyclopentyloxy group, cyclopropylethyloxy group, cyclobutylmethyloxy group, n-hexyloxy group, cyclohexyloxy group, cyclopropylpropyloxy group, cyclobutylethyloxy group, or cyclopentylmethyloxy group, etc.

In the present specification, an "alkylene" is a divalent group comprising a linear or branched saturated hydrocarbon, for example, methylene, 1-methylmethylene, 1,2-dimethylmethylene, ethylene, 1-methylethylene, 1-ethylethylene, 1,1-dimethylethylene, 1,2-dimethylethylene, 1,1-diethylethylene, 1,2-diethylethylene, 1-ethyl-2-methylethylene, trimethylene, 1-methyltrimethylene, 2-methyltrimethylene, 1,1-dimethyltrimethylene, 1,2-dimethyltrimethylene, 2,2-dimethyltrimethylene, 1-ethyltrimethylene, 2-ethyltrimethylene, 1,1-diethyltrimethylene, 1,2-diethyltrimethylene, 2,2-diethyltrimethylene, 2-ethyl-2-methyltrimethylene, tetramethylene, 1-methyltetramethylene, 2-methyltetramethylene, 1,1-dimethyltetramethylene, 1,2-dimethyltetramethylene, 2,2-dimethyltetramethylene, 2,2-di-n-propyltrimethylene, etc.

1. Compound Represented by General Formula (I) or Salt Thereof

One embodiment of the present invention is a compound represented by general formula (I) or a salt thereof.

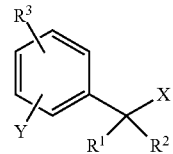

(I)

Specifically, as a result of molecular design of compounds that release quinone methides upon activation by specific enzyme activity in cancer cells utilizing the research findings of the present inventors obtained from SPiDER probes, etc., which, as mentioned above, emit fluorescence by an enzymatic reaction and prevent leakage from cells by being tagged to intracellular thiols, based on ideas based on quinone methides chemistry, the present inventors discovered that compounds represented by general formula (I) can cause serious damage cell-selectively by cancer cell-specific enzyme activity and are useful as novel prodrug-type anticancer agents (see FIG. 2).

Here, in general formula (I), Y is an enzyme recognition site, a part of which is cleaved by cancer cells-specific enzyme activity to induce formation of quinone methides.

Y can be selected in accordance with the type of enzyme. When the target enzyme of the prodrug-type anticancer agent is a glycosidase, Y is selected from groups derived from saccharides; when the target enzyme is a peptidase, Y is selected from groups derived from amino acids and groups including amino acids.

In general formula (I), Y is preferably —NH—CO-L, —NH-L', or —OL'.

Here, L is a partial structure of an amino acid. "Partial structure of an amino acid of L" means that L, together with the C=O to which L bonds, constitutes an amino acid, amino acid residue, peptide, or part of an amino acid.

In the present specification, any compound can be used as an "amino acid" as long as the compound has both an amino group and a carboxyl group, including natural and non-natural amino acids. An amino acid may be any of a neutral amino acid, basic amino acid, or acidic amino acid. In addition to amino acids that themselves function as transmitters such as neurotransmitters, amino acids that are structural components of polypeptide compounds such as bioactive peptides (including oligopeptides as well as dipeptides, tripeptides and tetrapeptides) and proteins can be used, for example, α amino acids, β amino acids, γ amino acids, etc. The use of an optically active amino acid as an amino acid is preferred. For example, either D- or L-amino acids may be used for a amino acids, but it is sometimes preferable to select an optically active amino acid that functions in the body.

In the present specification, "amino acid residue" means a structure corresponding to a partial structure remaining after a hydroxyl group has been removed from a carboxyl group of an amino acid.

Amino acid residues include residues of a amino acids, residues of β amino acids, and residues of γ amino acids. Examples of preferred amino acid residues include a "γ-glutamyl group" of a GGT substrate and a dipeptide "dipeptide comprising an amino acid-proline" of a DPP4 substrate, etc.

L' is a saccharide or a partial structure of a saccharide, a saccharide having a self-cleaving linker, an amino acid or a peptide having a self-cleaving linker.

The partial structure of a saccharide of L', together with the O to which L' bonds, constitutes a saccharide or part of a saccharide.

Examples of saccharides include β-D-glucose, β-D-galactose, β-L-galactose, β-D-xylose, α-D-mannose, β-D-fucose, α-L-fucose, β-L-fucose, β-D-arabinose, β-L-arabinose, β-D-N-acetylglucosamine, β-D-N-acetylgalactosamine, etc. β-D-galactose is preferred.

A self-cleaving linker means a linker that spontaneously cleaves and decomposes. Examples include a carbamate, urea, p-aminobenzyloxy group, etc.

According to one preferred aspect of the present invention, Y has a structure selected from the following.

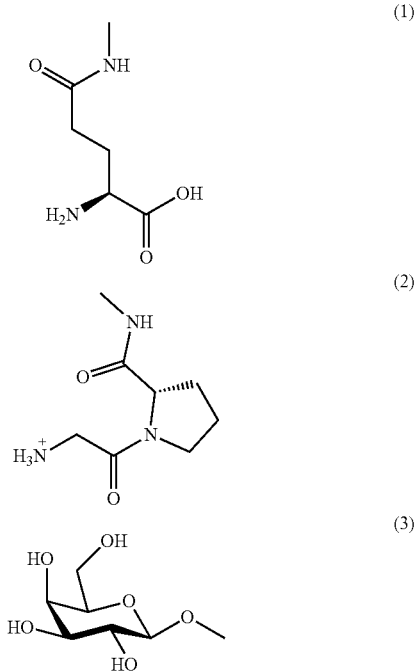

In general formula (I), X acts as a leaving group that leaves the benzene ring due to cleavage of part of the enzyme recognition site of Y by cancer cell-specific enzyme activity, resulting in formation of quinone methides.

X is selected from the group consisting of a fluorine atom, ester group (—OC(=O)—R'), carbonate group (—OCO$_2$—R'), carbamate group (—OCONH—R'), phosphoric acid and ester groups thereof (—OP(=O)(—OR')(—OR")), and sulfuric acid and ester groups thereof (—OSO$_2$—OR').

Here, R' and R" are each independently selected from substituted or unsubstituted alkyl groups or substituted or unsubstituted aryl groups.

A fluorine atom or an ester group (—OCO—R') is preferred as X. Without wishing to be bound by any theory, quinone methides is formed quickly upon cleavage of Y when X is a fluorine atom or an ester group (—OCO—R').

$R^1$ and $R^2$ are each independently selected from a hydrogen atom or a monovalent substituent. Monovalent substituents include halogen atoms and $C_1$ or higher alkyl groups (e.g., $C_{1-6}$ alkyl groups).

$R^1$ and $R^2$ are preferably each independently selected from a hydrogen atom or a fluorine atom.

—Y in general formula (I) preferably bonds to —$C(R^1)(R^2)X$ on the ortho position or para position of the benzene ring. A quinone methides structure can be formed upon cleavage of Y when —Y and $C(R^1)(R^2)X$ have such a positional relationship.

$R^3$ represents a hydrogen atom, or from one to four identical or different monovalent substituents present on a benzene ring.

The monovalent substituent of $R^3$ is selected from the group consisting of a $C_1$ or higher alkyl group (e.g., $C_{1-6}$ alkyl groups), alkoxycarbonyl group, nitro group, amino group, hydroxyl group, alkylamino group (—NHR', —NH-COR'), alkoxy group (—OR', —OCOR'), halogen atom, boryl group, and cyano group. Here, R' is a substituted or unsubstituted alkyl group or a substituted or unsubstituted aryl group.

An alkyl group having one or more carbons (e.g., an about $C_{1-6}$ alkyl group (e.g., a methyl group)) is preferred as the monovalent substituent of $R^3$. Without wishing to be bound by any theory, an alkyl group can improve the electron donating property and improve the cytocidal activity.

The 5 position, which is the para position, or the 4 position, which is the meta position, of —$C(R^1)(R^2)X$ is preferred as the position of $R^3$.

In addition, unless stated otherwise, compounds represented by general formula (I) also include stereoisomers such as tautomers, geometric isomers (e.g., E form, Z form, etc.), enantiomers, etc. Specifically, when a compound represented by general formula (I) includes one or more asymmetric carbons, the stereochemistry of asymmetric carbons allows each independently to take on an (R) form or an (S) form and to exist as a stereoisomer such as enantiomer or a diastereomer of the derivative. Therefore, any stereoisomer in pure form, any mixture of stereoisomers, racemates, and the like can be used as an active ingredient of a microtubule polymerase inhibitor of the present invention, and all are encompassed within the scope of the present invention.

Nonlimiting examples of compounds represented by general formula (I) or salts thereof appear below.

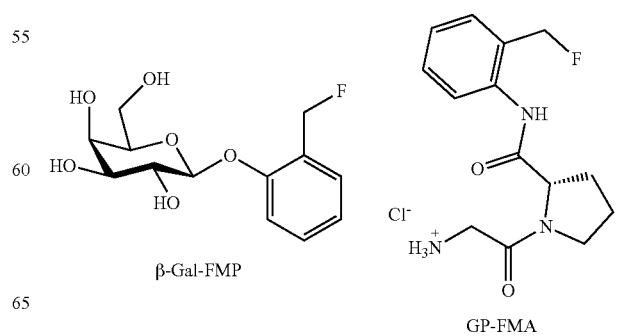

β-Gal-FMP

GP-FMA

-continued

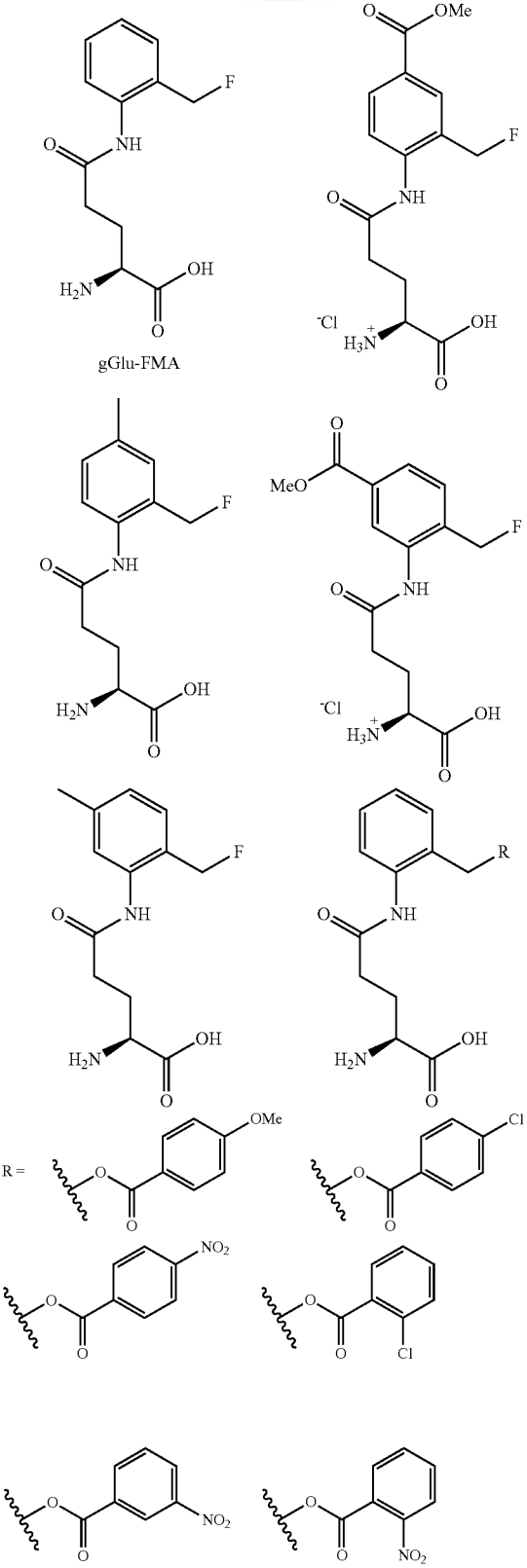

2. Prodrug-Type Anticancer Agent

Another embodiment of the present invention is a prodrug-type anticancer agent that comprises a compound of general formula (I) or a pharmaceutically acceptable salt thereof (also referred to hereinafter as the "prodrug-type anticancer agent of the present invention").

In addition, another embodiment of the present invention is a prodrug-type anticancer agent that acts cell-selectively by cancer cell-specific enzyme activity, the prodrug-type anticancer agent comprising a compound of general formula (I) or a pharmaceutically acceptable salt thereof.

Peptidases and glycosidases exist as cancer cell-specific enzymes.

Examples of peptidases include γ-glutamyl transpeptidase (GGT), dipeptidyl peptidase IV (DPP-IV), and calpain.

Examples of glycosidases include β-galactosidase, β-glucosidase, α-mannosidase, α-L-fucosidase, β-hexosaminidase, β-N-acetylgalactosaminidase, etc.

In addition, another embodiment of the present invention is a pharmaceutical composition for treating or preventing cancers such as breast cancer, esophageal cancer, lung cancer, head and neck cancer, oral cancer, liver cancer, etc. that includes a compound of general formula (I) or a pharmaceutically acceptable salt thereof (also referred to hereinafter as the "pharmaceutical composition of the present invention").

In addition, another embodiment of the present invention is a method for treating cancers such as breast cancer, esophageal cancer, lung cancer, head and neck cancer, oral cancer, liver cancer, etc. in a mammal, especially in a human, wherein the method administers an effective amount of a compound of the present invention of general formula (I) or a pharmaceutically acceptable salt thereof or a pharmaceutical composition comprising a compound represented by general formula (I) or a pharmaceutically acceptable salt thereof to a mammal requiring treatment.

A prodrug-type anticancer agent or pharmaceutical composition of the present invention may comprise not only a compound represented by general formula (I) but a salt thereof or a solvate or hydrate of these. Salts are not particularly limited as long as they are pharmaceutically acceptable salts, and examples can include base addition salts, acid addition salts, amino acid salts, etc. Examples of base addition salts include a sodium salt, potassium salt, calcium salt, magnesium salt, and other such alkaline earth metal salts, an ammonium salt, or a triethylamine salt, piperidine salt, morpholine salts, or other such organic amine salts. Examples of acid addition salts include a hydrochloride, hydrobromide, sulfate, nitrate, phosphate, and other such mineral acid salts; methanesulfonic acid, benzenesulfonic acid, p-toluenesulfonic acid, acetic acid, propionate, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid, salicylic acid, and other such organic acid salts. Examples of amino acid salts include a glycine salt, aspartate, glutamate, etc. Metal salts such as an aluminum salt, etc. are also acceptable.

The type of solvent for forming a solvate is not particularly limited. Examples include ethanol, acetone, isopropanol, and other such solvents.

Significant effects can be expected in a wide range of cancers, especially breast cancer, esophageal cancer, lung cancer, head and neck cancer, oral cancer, liver cancer, etc., as diseases that can be treated or prevented by the prodrug-type anticancer agent of the present invention.

The prodrug-type anticancer agent or pharmaceutical composition of the present invention may be administered as a compound represented by general formula (I) or a pharmaceutically acceptable salt thereof, a hydrate, or a solvate, which is the active ingredient, alone but administration in the form of a pharmaceutical composition comprising the above substance, which is the active ingredient, and one or more formulation additives is generally preferred. The term "composition" as in the pharmaceutical composition encompasses not only a product comprising an active ingredient and an inert ingredient which constitutes a carrier (pharmaceutically acceptable excipient) but also any product that occurs directly or indirectly as a result of association, complexation, or aggregation of any two or more components, as a result of dissociation of one or more components, or as a result of another type of reaction or interaction of one or more components.

Two or more of the above compounds can be used in combination as an active ingredient of the prodrug-type anticancer agent or pharmaceutical composition of the present invention.

In addition, the prodrug-type anticancer agent or pharmaceutical composition of the present invention can also be made into a combination drug that uses a compound represented by general formula (I) or a pharmaceutically acceptable salt thereof, hydrate, or solvate which is an active ingredient in combination with an existing anticancer agent. Those known in the art can be used as existing anticancer agents. Examples include methotrexate, doxorubicin, cisplatin, etc.

There are no particular limitations as to the type of prodrug-type anticancer agent or pharmaceutical composition of the present invention. Examples of drug forms include a tablet, capsule, granule, powder, syrup, suspension, suppository, ointment, cream, gel, patch, inhalant, injection, etc. These formulations are prepared by the usual methods. Furthermore, liquid formulations may be in a form dissolved or suspended in water or another suitable solvent at the time of use. Tablets and granules may also be coated by a known method. In the case of an injection, an injection is prepared by dissolving a compound of the present invention in water, but the compound may be dissolved in physiological saline or glucose solution as needed and buffers and preservatives may be added. A formulation is supplied in any formulation form for oral or parenteral administration. For example, formulations can be prepared as pharmaceutical compositions for oral administration in the form of granules, fine granules, powders, hard capsules, soft capsules, syrups, emulsions, suspensions, or solutions, etc. and as pharmaceutical compositions for parenteral administration in the form of injections for intravenous administration, intramuscular administration, subcutaneous administration, etc., drip infusions, percutaneous absorption agents, transmucosal absorption agents, nasal drops, inhalants, suppositories, etc. Injections and drip infusions, etc. can also be used by preparing a powdered drug form such as a freeze-dried form and using it dissolved in an appropriate aqueous solvent such as physiological saline at the time of use. In addition, slow-release formulations coated by a polymer, etc. can also be administered directly into the brain.

The types of formulation additives used in production of a prodrug-type anticancer agent or pharmaceutical composition of the present invention, proportions of formulation additives to active ingredient, and method of producing a pharmaceutical composition can also be selected appropriately by one skilled in the art in accordance with the form of the composition. Inorganic or organic materials or solid or liquid materials can be used as formulation additives, and from 1% by weight to 90% by weight can generally be blended relative to the active ingredient weight. Specifically, examples of such materials include lactose, glucose, mannitol, dextrin, cyclodextrin, starch, sucrose, magnesium aluminometasilicate, synthetic aluminum silicate, carboxymethylcellulose sodium, hydroxypropyl starch, carboxymethylcellulose calcium, ion-exchange resin, methylcellulose, gelatin, gum Arabic, hydroxypropylcellulose, hydroxypropylmethylcellulose, polyvinyl pyrrolidone, light silicic anhydride, magnesium stearate, talc, tragacanth, bentonite, Veegum, titanium oxide, sorbitan fatty acid esters, sodium lauryl sulfate, glycerin, fatty acid glycerin esters, purified lanolin, glycerogelatin, Polysorbate, Macrogol, vegetable oils, waxes, liquid paraffin, white petrolatum, fluorocarbons, nonionic surfactants, propylene glycol, water and so on.

When producing a solid formulation for oral administration, the active ingredient and excipient components, for example, lactose, starch, crystalline cellulose, calcium lactate, silicic anhydride, etc., are mixed to make a powder and, if needed, a binder such as white sugar, hydroxypropylcellulose, polyvinylpyrrolidone, etc., a disintegrant such as carboxymethylcellulose, carboxymethylcellulose calcium, etc. is added and subjected to wet or dry granulation to make granules. When producing tablets, these powders and granules may be tableted without further modification or after adding a lubricant such as magnesium stearate, talc, etc. These granules and tablets can also be coated with an enteric coating base such as hydroxypropylmethylcellulose phthalate, methacrylic acid-methyl methacrylate polymer, etc. to make enteric-coated formulations or coated with ethyl cellulose, carnauba wax, hydrogenated oil, etc. to make a sustained-release formulation. In addition, when producing capsules, a powder or granules can be filled into a hard capsule, or soft capsules can be made by coating the active ingredient without further modification or after being dissolved in glycerin, polyethylene glycol, sesame oil, olive oil, etc. by a gelatin film.

When producing an injection, the active ingredient and, if needed, a pH adjuster such as hydrochloric acid, sodium hydroxide, lactose, lactic acid, sodium, sodium monohydrogen phosphate, sodium dihydrogen phosphate, etc. and an isotonifying agent such as sodium chloride, glucose, etc. are dissolved in distilled water for injection, filter sterilized, and filled into ampules, or an injection for dissolution at the time of use is made by adding mannitol, dextrin, cyclodextrin, gelatin, etc., and vacuum freeze drying. In addition, the active ingredient can also be emulsified in water by adding lecithin, Polysorbate 80, polyoxyethylene hydrogenated castor oil, etc. to make an emulsion for an injection.

There are no particular limitations as to the dosage and number of doses of the prodrug-type anticancer agent or pharmaceutical composition of the present invention; these can be selected as deemed appropriate by a physician in accordance with conditions such as the goal of preventing exacerbation/advance and/or treating the treatment target disease, type of disease, patient's weight and age, severity of the disease, etc. Generally, the daily adult dose in oral administration is about 0.01-1000 mg (active ingredient weight) and can be administered once or several times a day or every several days. When used as an injection, it is preferable to administer a daily dose of 0.001-100 mg (active ingredient weight) continuously or intermittently for an adult.

There are no particular limitations as to the method for producing compounds represented by general formula (I); synthesis methods for representative compounds among compounds encompassed by general formula (I) are presented concretely in the examples in the present specification. One skilled in the art could produce compounds encompassed by formula (I) by appropriately changing or modifying the starting raw materials, reaction reagents, reaction conditions, etc. while referring to the examples in the present specification and the schemes below.

EXAMPLES

The present invention is explained below through examples, but the present invention is not limited to these examples.

1. Synthesis of Quinone Methides Release-Type Prodrug Compounds

First, as shown in FIG. 3, monocyclic compounds having enzyme recognition sites for three types of enzymes (β-Gal, DPP-IV, GGT) and fluorine in the leaving group were synthesized according to the following procedure.

Synthesis Example 1

Compound 1 (β-Gal-FMP) of the present invention was synthesized according to scheme 1 below.

Scheme 1

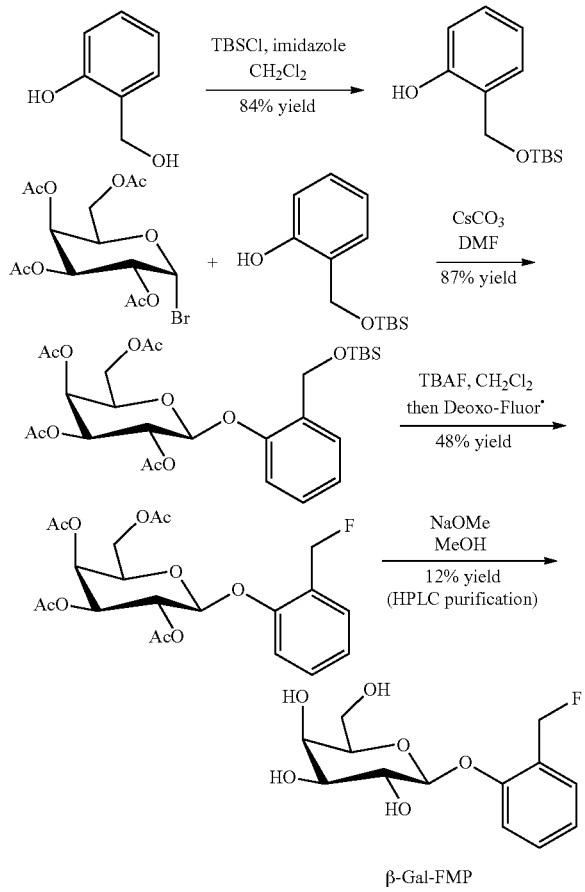

β-Gal-FMP (1) Synthesis of Compound 1

Compound 1

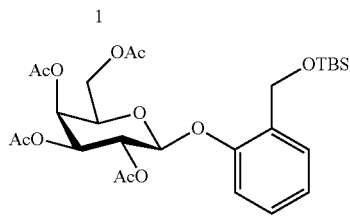

2-(((tert-butyldimethylsilyl)oxy)methyl)phenol (301 mg, 1.26 mmol) and cesium carbonate (4.11 g, 12.6 mmol) were dissolved in dehydrated DMF (7 mL) and stirred for five minutes at 0° C. in an argon atmosphere. (2R,3S,4S,5R,6R)-2-(acetoxymethyl)-6-bromotetrahydro-2H-pyran-3,4,5-trityl triacetate (4.51 g, 11.0 mmol) was added and stirred for five hours at 0° C. The end of the reaction was confirmed, saturated ammonium chloride aqueous solution was added, and the solution was extracted twice by ethyl acetate. The ethyl acetate layer was washed with saturated sodium bicarbonate and saline, dried by sodium sulfate, and then concentrated. A residue was generated by silica gel chromatography (34 g silica gel, 20%→40% ethyl acetate/hexane), and the target substance was obtained as a colorless liquid (626.8 mg, 87%).

$^1$H NMR (CD$_2$Cl$_2$, 400 MHz): δ7.50 (d, 1H, J=8.0 Hz), 7.20 (dd, 1H, J=8.0 Hz, J=7.3 Hz), 7.08 (dd, 1H, J=7.8 Hz, J=7.3 Hz), 7.00 (d, 1H, J=7.8 Hz), 5.47-5.43 (m, 2H), 5.13 (dd, 1H, J=11 Hz, J=3.7 Hz), 5.08 (d, 1H, J=8.2 Hz), 4.75 (d, 1H, J$_{gem}$=15 Hz), 4.62 (d, 1H, J$_{gem}$=15 Hz), 4.22-4.09 (m, 3H), 2.16 (s, 3H, OCOCH$_3$), 2.04 (s, 3H, OCOCH$_3$), 2.03 (s3H, OCOCH$_3$), 1.98 (s, 3H, OCOCH$_3$), 0.96 (s, 9H, Si(CH$_3$)$_3$), 0.12 (s, 6H, Si(CH$_3$)$_2$).

(2) Synthesis of Compound 2

Compound 2

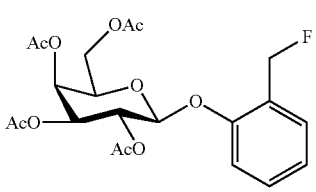

Compound 1 (76.7 mg, 0.135 mmol) was dissolved in dehydrated dichloromethane (5 mL) and the resulting solution was cooled to −78° C. TBAF (ca. 1 mol/L in THF, 39 μL, 0.135 mmol) was added and the resulting solution was stirred for one hour at −78° C. Next, Deoxo-Fluor® (132 μL, 0.675 mmol) was added and stirred for another hour. The end of the reaction was confirmed, saturated sodium bicarbonate aqueous solution was added, and the solution was extracted twice by dichloromethane. The ethyl acetate layer was washed with water and saline, dried by sodium sulfate, and then concentrated. A residue was generated by silica gel chromatography (34 g silica gel, 20%→40% ethyl acetate/hexane), and the target substance was obtained as a light-yellow liquid (29.7 mg, 48%).

$^1$H NMR (CDCl$_3$, 400 MHz): δ7.38 (d, 1H, J=7.8 Hz), 7.32 (dd, 1H, J=7.8 Hz, J=7.8 Hz), 7.10 (dd, 1H, J=8.2 Hz, J=7.8 Hz), 7.07 (d, 1H, J=8.2 Hz), 5.54 (dd, 1H, J=11 Hz, J=7.8 Hz), 5.47 (dd, 1H, J$_{HBn-F}$=48 Hz, J$_{gem}$=11 Hz), 5.46 (d, 1H, J=2.7 Hz), 5.23 (dd, 1H, J$_{HBn-F}$=48 Hz, J$_{gem}$=11 Hz), 5.11 (dd, 1H, J=11 Hz, J=3.7 Hz), 5.03 (d, 1H, J=7.8 Hz), 4.25 (dd, 1H, J=11 Hz, J=6.9 Hz), 4.15 (dd, 1H, J=11 Hz, J=6.0 Hz), 4.08 (dd, 1H, J=6.9 Hz, J=6.0 Hz), 2.18 (s, 3H, OCOCH$_3$), 2.06 (s, 3H, OCOCH$_3$), 2.06 (s, 3H, OCOCH$_3$), 2.01 (s, 3H, OCOCH$_3$).

(3) Synthesis of Compound 3

Compound 3

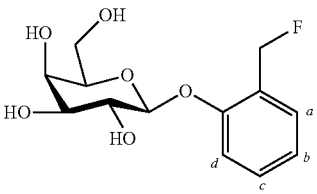

Compound 2 (29.7 mg, 0.0650 mmol) was dissolved in dehydrated methanol (5 mL) and cooled to 0° C. 28% NaOMe/MeOH (50 μL) was added and stirred for 12 hours at −78° C. The end of the reaction was confirmed, the reaction mixture was neutralized by Amberlite IR120®, filtered, and then concentrated. A residue was generated by reverse-phase HPLC (0%→100% acetonitrile/water), and the target substance was obtained as a white solid (2.25 mg, 12%).

¹H NMR (CD₃OD, 400 MHz): δ7.35 (d, 1H, Ha, $J_{Ha-Hb}$=7.3 Hz), 7.29 (dd, 1H, Hc, $J_{Hc-Hd}$=8.2 HZ, 3 Hz) 7.21 (d, 1H, Hd, $J_{Hd-Hc}$=8.2 Hz), 7.03 (dd, 1H, Hb, $J_{Hb-Ha}$=$J_{Hb-Hc}$=7.3 HZ), 5.51 (d, 2H, $H_{Bn}$, $J_{HBn-F}$=48 Hz), 4.85 (d, 1H, H1, JH1-H2=7.8 Hz), 3.88 (d, 1H, H4, $J_{H2-H3}$=3.7 Hz), 3.79 (dd, 1H, H2, $J_{H2-H3}$=9.6 Hz, $J_{H2-Hn}$=7.8 Hz), 3.78-3.70 (m, 2H, H6, 6'), 3.65 (dd, 1H, H5, $J_{H}$5-H6=6.9 Hz, $J_{H5-H6'}$=5.0 Hz), 3.55 (dd, 1H, H3, $J_{H3-H2}$=9.6 Hz, $J_{H3-H4}$=3.7 Hz); HRMS 311.08976 (M+Na⁺).

Synthesis Example 2

Compound 2 (GP-FMA) of the present invention was synthesized according to scheme 2 below.

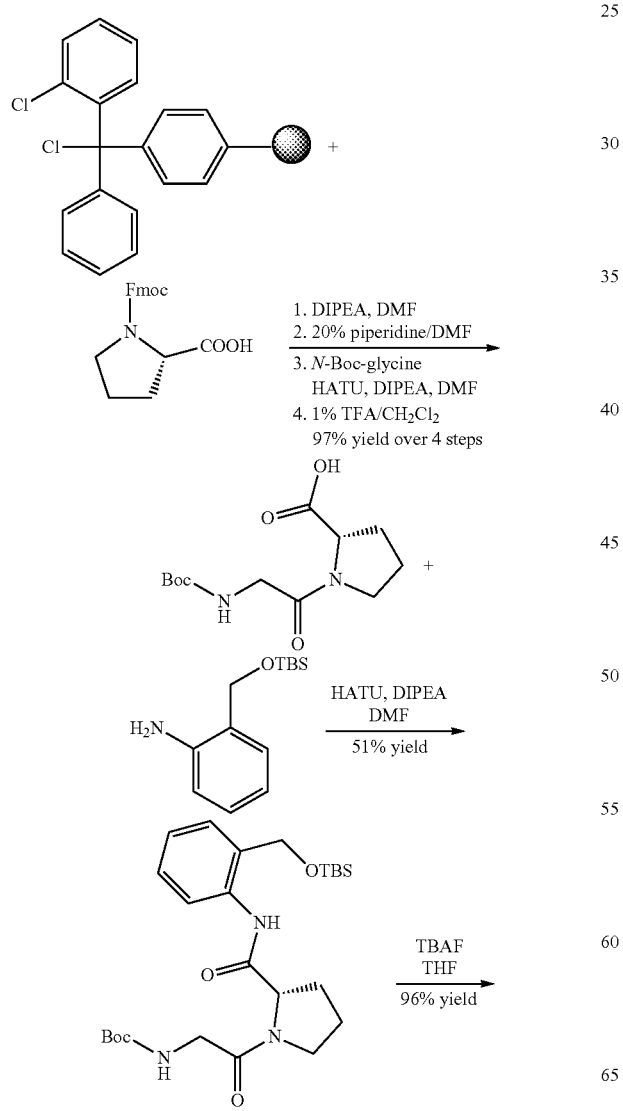

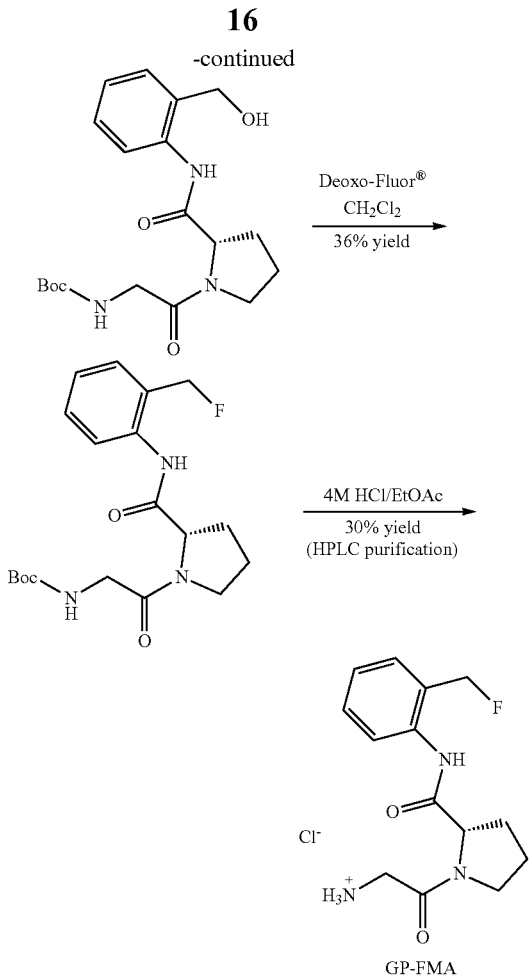

(1) Synthesis of Compound 4 tert-butyl(S)-(2-(2-((2-(((tert-butyldimethylsilyl)oxy) methyl)phenyl)carbamoyl 7)pyrrolidin-1-yl)-2-oxoethyl) carbamate (86.4 mg, 0.176 mmol) was dissolved in dehydrated DMF (2 mL) and cooled to 0° C. HATU (206 mg, 0.532 mmol) and DIPEA (183 μL, 1.06 mmol) were added and stirred for five minutes at 0° C. Next, 2-(tert-butyldimethylsilyl)oxy)methyl)aniline (101 mg, 0.425 mol) dissolved in dehydrated DMF (1 mL) was added, and the resulting solution was warmed to room temperature and stirred for another 12 hours. The end of the reaction was confirmed, water was added, and the solution was extracted twice by ethyl acetate. The ethyl acetate layer was washed with saturated sodium bicarbonate aqueous solution and saline, dried by sodium sulfate, and then concentrated. A residue was generated by silica gel chromatography (34 g silica gel, 40%→50% ethyl acetate/hexane), and the target substance was obtained as a white solid (88.1 mg, 51%).

$^1$H NMR (CD$_3$OD, 400 MHz): δ7.44-7.41 (m, 2H), 7.28-7.18 (m, 2H), 4.75 (d, 1H, HBn, J$_{gem}$=14 Hz), 4.70 (d, 1H, HBn', J$_{gem}$=14 Hz), 4.53 (dd, 1H, J=8.5 Hz, J=2.7 Hz), 3.95 (d, 1H, J$_{gem}$=17 Hz), 3.88 (d, 1H, J$_{gem}$=17 Hz), 3.71-3.56 (m, 2H), 2.17-1.91 (m, 3H), 1.41 (s, 9H, NHCOO(CH$_3$)$_3$), 0.91 (s, 9H, Si(CH$_3$)$_3$), 0.09 (s, 6H, Si(CH$_3$)$_2$).

(2) Synthesis of Compound 5

Compound 5

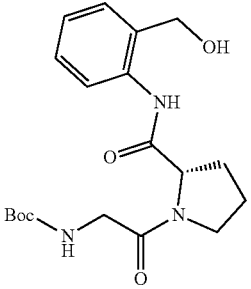

Compound 4 (96.5 mg, 0.354 mmol) was dissolved in dehydrated THF (5 mL), TBAF (ca. 1 mol/L in THF, 879 μL, 0.879 mmol) was added, and the solution was stirred for one hour at room temperature. The end of the reaction was confirmed, and the reaction solution was concentrated. A residue was generated by silica gel chromatography (14 g silica gel, 0%→7% methanol/dichloromethane), and the target substance was obtained as a colorless liquid (63.9 mg, 96%).

$^1$H NMR (CD$_3$OD, 400 MHz): δ7.70 (d, 1H, J=7.8 Hz), 7.30 (d, 1H, J=7.8 Hz), 7.25 (ddd, 1H, J=7.8 Hz, J=7.8 Hz, J=1.4 Hz), 7.13 (ddd, 1H, J=7.8 Hz, J=7.8 Hz, J=1.4 Hz), 4.61 (dd, 1H, HBn, J$_{gem}$=14 Hz, J=4.1 Hz), 4.57 (dd, 1H, HBn, J$_{gem}$=14 Hz, J=4.1 Hz), 4.55 (dd, 1H, J=8.5 Hz, J=3.7 Hz), 3.94 (s, 2H), 3.73-3.55 (m, 2H), 2.30-2.12 (m, 2H), 2.10-2.03 (m, 1H), 1.43 (s, 9H, NHCOO(CH$_3$)$_3$).

(3) Synthesis of Compound 6

Compound 6

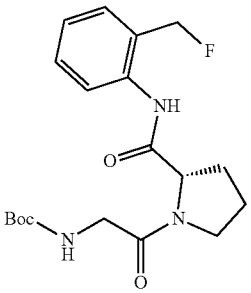

Compound 5 (63.9 mg, 0.169 mmol) was dissolved in dehydrated dichloromethane (2 mL) and cooled to 0° C. Deoxo-Fluor® (166 μL, 0.847 mmol) was added and stirred for one hour at room temperature. The end of the reaction was confirmed, saturated sodium bicarbonate aqueous solution was added, and the solution was extracted twice by ethyl acetate. The ethyl acetate layer was washed with water and saturated sodium bicarbonate aqueous solution and saline, dried by sodium sulfate, and then concentrated. A residue was generated by silica gel chromatography (34 g silica gel, 50%→70% ethyl acetate/hexane), and the target substance was obtained as a light-yellow liquid (22.9 mg, 36%).

$^1$H NMR (CDCl$_3$, 400 MHz): δ8.93 (brs, 1H, —CONH—), 7.95 (d, 1H, J=7.8 Hz), 7.36 (dd, 1H, J=7.8 Hz, J=7.8 Hz), 7.29 (d, 1H, J=7.3 Hz), 7.13 (dd, 1H, J=7.8 Hz, J=7.3 Hz), 5.41 (brs, 1H, —OCONH—), 5.39 (d, 2H, HBn, J$_{HBn-F}$=48 Hz), 4.76 (d, 1H, J=6.9 Hz), 4.03 (dd, 1H, J$_{gem}$=17 Hz, J=5.0 Hz), 3.93 (dd, 1H, J$_{gem}$=17 Hz, J=4.6 Hz), 3.60-3.54 (m, 1H), 3.49-3.40 (m, 1H), 2.22-2.11 (m, 1H), 2.11-2.02 (m, 1H), 2.01-1.90 (m, 1H), 1.44 (s, 9H, NHCOO(CH$_3$)$_3$).

(4) Synthesis of Compound 7

Compound 7

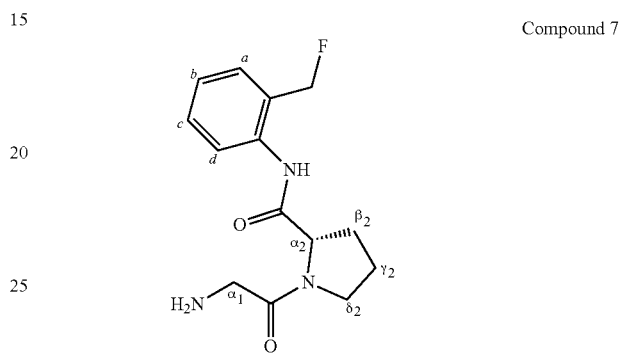

Compound 6 (22.9 mg, 0.0604 mmol) was dissolved in ethyl acetate (1 mL), 4M hydrochloric acid/ethyl acetate (2 mL) was added, and the solution was stirred for 12 hours at room temperature. The end of the reaction was confirmed, and the reaction solution was concentrated. A residue was generated by reverse-phase HPLC (0.1% acetic acid, 0%→100% acetonitrile/water), and the target substance was obtained as a white solid (5.7 mg, 30%).

$^1$H NMR (CD$_3$OD, 400 MHz): δ7.46 (d, 1H, Ha, J$_{Ha-Hb}$=7.3 Hz), 7.41-7.27 (m, 3H, Hb, Hc, Hd), 5.38 (ddd, 2H, HBn, J$_{HBn-F}$=48 Hz, J$_{HBn'-F}$=34 Hz, J$_{gem}$=11 Hz), 4.61 (dd, 1H, Hα$_2$, J$_{α2-β2}$=8.2 Hz, J$_{α2-β2'}$=3.7 Hz), 3.88 (d, 2H, Hα1, J$_{gem}$=4.1 Hz), 3.68-3.52 (m, 2H, H5), 2.39-2.28 (m, 1H, Hβ2), 2.17-1.97 (m, 3H, Hβ2, Hγ2); $^{13}$C NMR (CD$_3$OD, 100 MHz): δ172.1, 164.8, 128.9, 128.1, 126.6, 125.9, 60.6, 46.4, 40.2, 29.5, 24.5; HRMS 280.14657 (M+H$^+$).

Synthesis Example 3

Compound 3 (gGlu-FMA) of the present invention was synthesized according to scheme 3 below.

Scheme 3

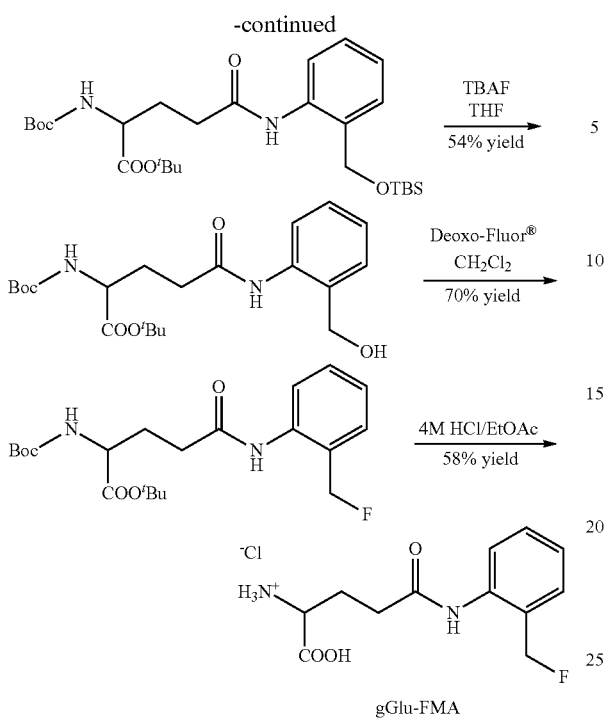

gGlu-FMA (1) Synthesis of Compound 8

Compound 8

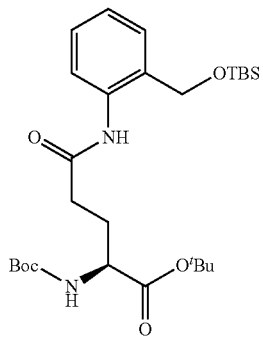

(S)-5-(tert-butoxy)-4-((tert-butoxycarbonyl)amino)-5-oxopentanoic acid (1.26 g, 4.17 mmol) was dissolved in dehydrated DMF (15 mL) and cooled to 0° C. HATU (2.42 g, 6.25 mmol) and DIPEA (2.16 mL, 12.5 mmol) were added and stirred for five minutes at 0° C. Next, 2-(tert-butyldimethylsilyl)oxy)methyl)aniline (1.19 g, 5.00 mmol) dissolved in dehydrated DMF (5 mL) was added, and the solution was warmed to room temperature and stirred for another 12 hours. The end of the reaction was confirmed, water was added, and the solution was extracted twice by ethyl acetate. The ethyl acetate layer was washed with water and saturated sodium bicarbonate aqueous solution and saline, dried by sodium sulfate, and then concentrated. A residue was generated by silica gel chromatography (34 g silica gel, 10%→30% ethyl acetate/hexane), and the target substance was obtained as a yellow liquid (2.18 g, quantitative).

$^1$H NMR (CDCl$_3$, 400 MHz): δ8.88 (brs, 1H, —CONH—), 8.15 (d, 1H, J=8.2 Hz), 7.29 (dd, 1H, J=8.2 Hz, J=7.3 Hz), 7.10 (d, 1H, J=6.9 Hz), 7.13 (dd, 1H, J=7.3 Hz, J=6.9 Hz), 5.20 (brd, 1H, —OCONH—, J=7.8 Hz), 4.75 (d, 1H, HBn, J$_{gem}$=13 Hz), 4.71 (d, 1H, HBn', J$_{gem}$=13 Hz), 4.27-4.15 (m, 1H), 2.52-2.34 (m, 2H), 2.32-2.20 (m, 1H), 2.07-1.95 (m, 1H), 1.46 (s, 9H, COO(CH$_3$)$_3$), 1.42 (s, 9H, NHCOO(CH$_3$)$_3$), 0.90 (s, 9H, Si(CH$_3$)$_3$), 0.07 (s, 6H, Si(CH$_3$)$_2$).

(2) Synthesis of Compound 9

Compound 9

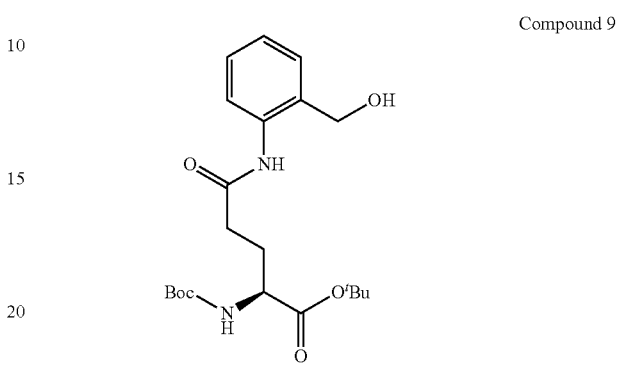

Compound 8 (2.18 g, 4.17 mmol) was dissolved in dehydrated THF (10 mL), TBAF (ca. 1 mol/L in THF, 10 mL, 10 mmol) was added, and the solution was stirred for two hours at room temperature. The end of the reaction was confirmed, and the reaction solution was concentrated. A residue was generated by silica gel chromatography (34 g silica gel, 20%→80% ethyl acetate/hexane), and the target substance was obtained as a white solid (943 mg, 54%).

$^1$H NMR (CD$_2$Cl$_2$, 400 MHz): δ 8.69 (brs, 1H, —CONH—), 7.91 (d, 1H, J=7.3 Hz), 7.29 (dd, 1H, J=7.8 Hz, J=7.3 Hz), 7.23 (d, 1H, J=7.3 Hz), 7.09 (dd, 1H, J=7.8 Hz, J=6.3 Hz), 4.66 (m, 2H, HBn), 4.22-4.11 (m, 1H), 2.80 (brs, 1H, —CH$_2$OH), 2.51-2.35 (m, 2H), 2.29-2.16 (m, 1H), 1.97-1.85 (m, 1H), 1.44 (s, 9H, COO(CH$_3$)$_3$), 1.40 (s, 9H, NHCOO(CH$_3$)$_3$).

(3) Synthesis of Compound 10

Compound 10

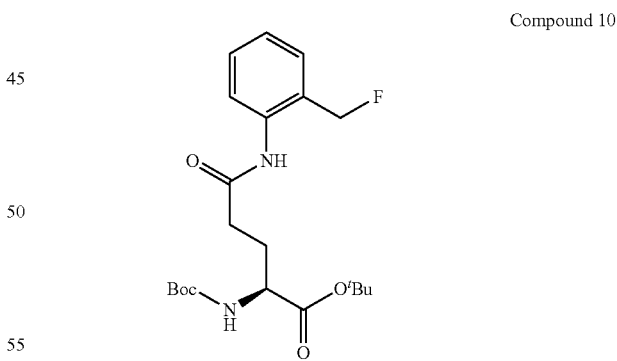

Compound 9 (215 mg, 0.527 mmol) was dissolved in dehydrated dichloromethane (10 mL) and cooled to 0° C. Deoxo-Fluor® (514 μL, 2.64 mmol) was added and stirred for 12 hours at room temperature. The end of the reaction was confirmed, saturated sodium bicarbonate aqueous solution was added, and the solution was extracted twice by ethyl acetate. The ethyl acetate layer was washed with saturated sodium bicarbonate aqueous solution and saline, dried by sodium sulfate, and then concentrated. A residue was generated by silica gel chromatography (34 g silica gel, 20%→30% ethyl acetate/hexane), and the target substance was obtained as a light-yellow liquid (151.8 mg, 70%).

$^1$H NMR (CD$_2$Cl$_2$, 40 MHz): δ8.04 (brs, 1H, —CONH—), 7.84 (d, 1H, J=8.2 Hz), 7.37 (dd, 1H, J=8.2 Hz, J=7.3 Hz), 7.33 (d, 1H, J=6.9 Hz), 7.17 (dd, 1H, J=7.3 Hz, J=6.9 Hz), 5.43 (d, 2H, HBn, 48 Hz, J$_{gem}$=11 Hz), 4.22-4.11 (m, 1H), 2.80 (brs, 1H, —CH$_2$OH), 2.51-2.35 (m, 2H), 2.29-2.16 (m, 1H), 1.97-1.85 (m, 1H), 1.44 (s, 9H, COO(CH$_3$)$_3$), 1.40 (s, 9H, NHCOO(CH$_3$)$_3$).

(4) Synthesis of Compound 11

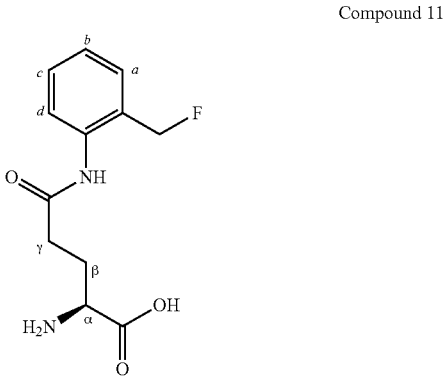 [SMILES: N[C@@H](CCC(=O)Nc1ccccc1CF)C(=O)O]

Compound 11

Compound 10 (70.3 mg, 0.171 mmol) was dissolved in ethyl acetate (2 mL), 4M hydrochloric acid/ethyl acetate (2 mL) was added, and the solution was stirred for 12 hours at room temperature. The end of the reaction was confirmed, and the reaction solution was concentrated. A residue was generated by reverse-phase HPLC (0.1% acetic acid, 0%→100% acetonitrile/water), and the target substance was obtained as a white solid (28.9 mg, 58%).

$^1$H NMR (CD$_2$Cl$_2$, 400 MHz): δ7.49 (d, 1H, Ha, J$_{Ha-Hb}$=7.8 Hz), 7.43 (dd, 1H, Hc, J$_{Hc-Hb}$=J$_{Hc-Hd}$=7.8 Hz), 7.36 (dd, 1H, Hb, J$_{Hb-Ha}$=J$_{Hb-Hc}$=7.8 Hz), 7.29 (d, 1H, Hd, J$_{Hd-Hc}$=7.8 Hz), 5.35 (d, 2H, HBn, J$_{HBn-F}$=4.8 Hz), 3.80-3.77 (m, 1H, Hα), 2.67-2.56 (m, 2H, Hγ), 2.20-2.15 (m, 2H, Hβ); $^{13}$C NMR (D$_2$O, 100 MHz): δ174.7, 173.8, 134.3, 132.0, 130.4, 130.0, 128.1, 127.5, 82.9, 81.3, 54.1, 31.6, 26.3; HRMS 255.11370 (M+H$^+$).

Example 1

Next, enzymatic reactions were carried out under the following conditions using the three compounds synthesized and purified enzymes.
Final compound concentration: 100 μM
Final enzyme concentration: 4 nM (β-Gal), 8.5 μg/mL (DPP-IV), 10 U/mL (GGT)
Reaction temperature: 37° C.
(1) Enzymatic Reaction Using β-Galactosidase
Instrument: ACQUITY UPLC (manufactured by Waters Corporation)
Column: Poroshell 120, 4.6×100 mm (manufactured by Agilent Technologies, Inc.)
Mobile phase A: water (0.01M ammonium formate)
Mobile phase B: 80% acetonitrile/water (0.01M ammonium formate)
Gradient: A/B: 95/5-5/95, 5 min (2) Enzymatic Reaction Using DPP-IV and GGT
Instrument: 1260 Infinity (manufactured by Agilent Technologies, Inc.)
Column: Poroshell 120, 4.6×100 mm (manufactured by Agilent Technologies, Inc.)
Mobile phase A: water (0.01M ammonium formate)
Mobile phase B: 80% acetonitrile/water (0.01M ammonium formate)
Gradient: A/B: 95/5-50/50, 20 min The results are shown in FIG. 4.

Compounds 1-3 were confirmed to be cleaved by β-Gal, DPP-IV, and GGT, respectively, and 2-hydroxybenzyl alcohol (β-Gal) or 2-aminobenzyl alcohol (DPP-IV and GGT) in which quinone methides reacted with water was confirmed as the reaction product.

Experiments were also conducted on GGT using an inhibitor. The enzymatic reaction of the model compound was confirmed to be inhibited when GGsTop®, a GGT inhibitor, was added in a concentration of 100 μM.

Example 2

In Vitro Efficacy Study Using Cells with High and Low Enzyme Expression

Next, it was verified whether compounds 1-3 can change the cell viability by functioning as a prodrug when administered to cells with high and low enzyme expression. The efficacy studies were carried out by using a general colorimetric method called CCK-8 assay (method for quantifying the dehydrogenase activity inside living cells through reduction of colorless WST-8 to orange formazan) to quantify the number of living cells. The CCK-8 assay evaluation method is described below.

(1) Cultured Cells Used

The B-galactosidase-activated prodrug was evaluated using HEK/lac Z cells (cells derived from human kidney cells, high β-Gal expression) and HEK293 cells (cells derived from human kidney cells, low β-Gal expression). The DPP-IV-activated prodrug was evaluated using H226 cells (human lung squamous cell carcinoma cells, high DPP-IV expression) and H460 cells (human non-small cell epithelial lung cancer cells, low DPP-IV expression). The GGT-activated prodrug was evaluated using SHIN3 cells (human ovarian cancer cells, high GGT expression) and H226 cells (human lung squamous cell carcinoma cells, low GGT expression).

(2) Evaluation Method

Each type of cell was seeded in 96-well plates (cell density: 1.0×10$^4$/well) and incubated overnight. The medium was exchanged for fresh medium, and the synthesized derivatives were added (final concentration 1-50 μM, 0.5% DMSO, n=3). After culturing the cells for another 24 hours, a Cell Counting Kit-8 (10 μL/well, manufactured by Promega Corporation) was added. After 2.5 hours, the 450 nm absorbance was measured by a plate reader, and the number of viable cells was quantified.

The results of CCK-8 assay are shown in FIGS. 5-7.

First, compound 1 (β-Gal-FMP) for β-galactosidase was administered to high-expression cells (HEK/lac Z) and low-expression cells (HEK293), and the survival rate was calculated after 24 hours. As a result, the survival rate of the two cells did not drop at all even when a high concentration of 50 μM was administered, and no significant difference was observed (FIG. 5). In contrast to the results with β-galactosidase, changes in the cell viability were observed between cells with high and low enzyme expression when compounds 2 and 3 (GP-FMA and gGlu-FMA) of DPP-IV and GGT, which are aminopeptidases, were used (FIGS. 6 and 7). These results suggested that (i) a difference in the location of DPP-IV and GGT (cell membrane) and β-galactosidase (cytoplasm) and (ii) a difference in the type of quinone methides (DPP-IV and GG release azaquinone methides) are important, but this remains uncertain at present. The majority of the manifestation of effect was expected to depend on the GGT activity since the GGT prodrug in particular had high cell type selectivity and the GGT inhibitor GGsTop® completely restored the survival rate.

Example 3

Study Relating to Cell Death Observation Under Coculture Conditions

Since changing the types of cells and standardizing the medium to RPMI-1640 made coculture possible, the aim then became to observe cell death under coculture conditions and to construct a quantitative method. It was decided to conduct these studies using compound 3 for GGT (gGlu-FMA) based on the results obtained thus far, and the possibility of visually observing cell death by observation of fluorescence using one type of cell was first explored as an initial study (FIG. 8). The experiment was carried out according to protocol 1 shown in FIG. 18.

FIG. 8 shows fluorescence imaging over time of SHIN3 cells (top) and H226 cells (bottom) using compound 3 and EthD-1 (dead cell staining, Ex/Em=525 nm/511-564 nm). Lens: 63×/1.4 oil.
Scan mode: xyzt, x=512, y=512, z=4, t=24. Scale bar: 50 μm.

Since the results in FIG. 8 made it possible to confirm that more cell death occurred in SHIN3 cells, which are a cell line with high GGT expression, evaluation was then carried out in a coculture system. The experiment was carried out according to protocol 2 shown in FIG. 19.

The results are shown in FIG. 9.

FIG. 9 shows time-lapse fluorescence imaging of cells cocultured using compound 3 and EthD-1 (dead cell staining, Ex/Em=525 nm/511-564 nm) (top).
Confocal imaging of cells in three other fields after 24-hr imaging (bottom).
Lens: 63×/1.4 oil.
Scan mode: xyzt, x=512, y=512, z=4, t=24. Scale bar: 50 μm.

As is understood from the results of 24 hr time-lapse imaging shown in the upper part of FIG. 9, it was clarified that compound 3 for GGT (gGlu-FMA) selectively damages high-expression cells even in a coculture system. Also, since phototoxicity was observed (many cells died in the field) in previous studies conducted by imaging 10 slices×24 times, there was concern about the effects of phototoxicity even though this study imaged 4 slices×24 times. When three other fields were imaged after the end of 24-hr imaging (FIG. 9 bottom), the killing was judged to have been achieved by compound 3 working well because the same tendency for dead cells to be present in the gaps between low-expression cells (green) was seen.

Example 4

Efficacy Evaluation by Flow Cytometry

Imaging using fluorescent dye showed that cell death under coculture conditions can be observed in real time. On the other hand, since it is impossible to quantitatively discuss the extent to which the survival rates of high-expression/low-expression cells have changed, the present inventors studied whether this could be evaluated using flow cytometry (FIG. 10). The experiment was carried out according to protocol 3 shown in FIG. 20.

FIG. 10 shows the results of flow cytometry analysis of cell proliferation in SHIN3 cells (green) and H226 cells (not stained) using compound 3. (Top) 25 μM model compound, (middle) 25 μM model compound+100 μM GGsTop, (bottom) 0.25% DMSO control. Analysis was carried out after 24-hr incubation.

From the results in FIG. 10, flow cytometry also clarified that cell death was induced only in the GGT prodrug group (dead staining by EthD-1 seen), triggering selective cell death of SHIN3 cells, which are cells with high GGT expression.

Synthesis of Benzyl-Position Leaving Group-Converted Derivatives

Next, the synthesis of benzyl position-converted derivatives targeting GGT was studied. The possibility of synthesis of a derivative having an acyl-based leaving group was verified as shown in FIG. 11, using as a reference Evans' $pK_a$ table (D. H. Ripin; D. A. Evans, http://evans.rc.fas.harvard.edu/pdf/evans_pKa_table.pdf).

Synthesis Example 4

The compounds of the present invention were synthesized according to scheme 4 below.

Scheme 4

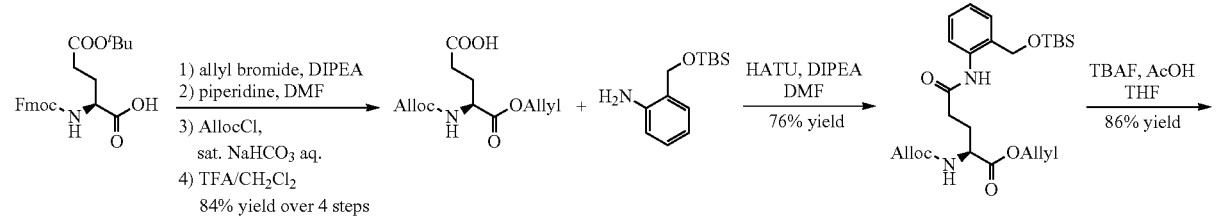

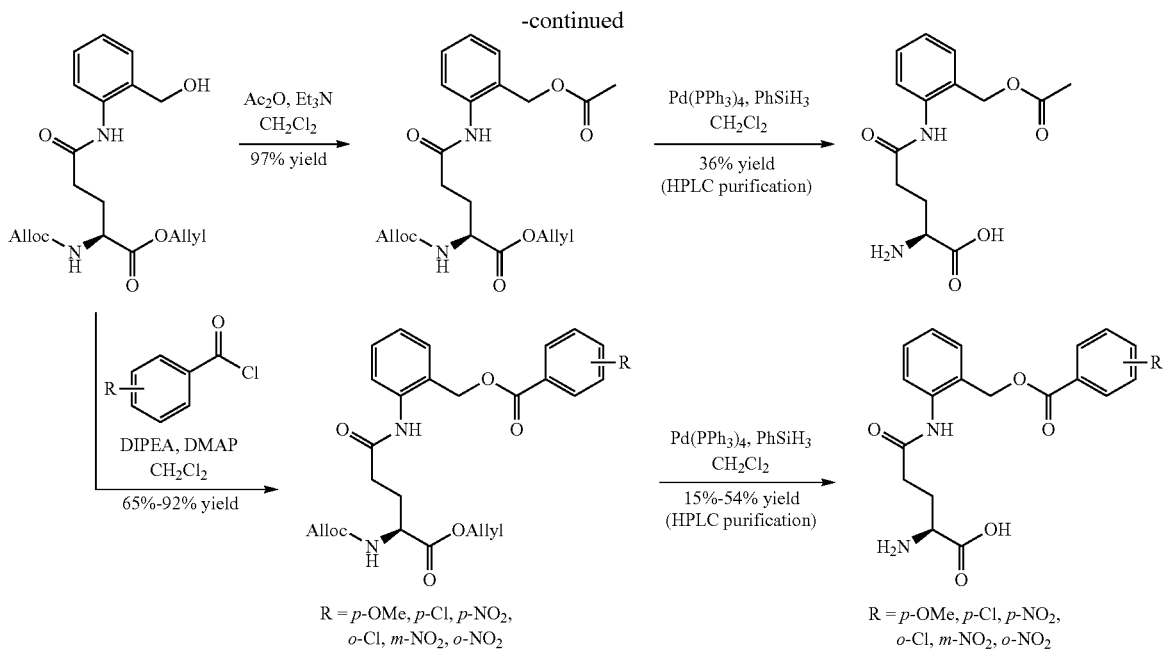

(1) Synthesis of Compound 11

Compound 11

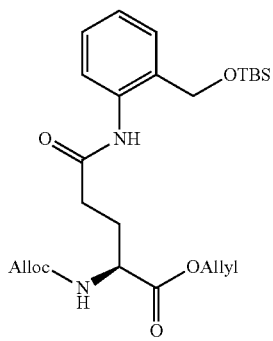

(S)-5-(allyloxy)-4-(((allyloxy)carbonyl)amino)-5-oxopentanoic acid (930 mg, 3.45 mmol) was dissolved in dehydrated DMF (17 mL) and cooled to 0° C. HATU (1.96 g, 5.14 mmol) and DIPEA (1.75 mL, 10.3 mmol) were added and stirred for five minutes at 0° C. Next, 2-(tert-butyldimethylsilyl)oxy)methyl)aniline (1.22 g, 5.14 mmol) dissolved in dehydrated DMF (5 mL) was added, warmed to room temperature, and stirred for another 12 hours. The end of the reaction was confirmed, water was added, and the solution was extracted twice by ethyl acetate. The ethyl acetate layer was washed with water and saturated sodium bicarbonate aqueous solution and saturated saline, dried by sodium sulfate, and then concentrated. The residue was purified by silica gel chromatography (34 ag silica gel, 50%→60% ethyl acetate/hexane), and the target substance was obtained as a yellow liquid (848 mg, 86%).

$^1$H NMR (CDCl$_3$, 400 MHz): δ8.91 (brs, 1H, —CONH—), 8.16 (d, 1H, J=7.8 Hz), 7.29 (dd, 1H, J=7.8 Hz, J=7.3 Hz), 7.08 (d, 1H, J=7.3 Hz), 7.02 (dd, 1H, J=7.3 Hz, J=7.3 Hz), 5.95-5.82 (m, 2H), 5.61 (brd, 1H, —OCONH—, J=7.8 Hz), 5.32 (d, 1H, J=17 Hz), 5.28 (d, 1H, J=17 Hz), 5.24 (d, 1H, J=11 Hz), 5.18 (d, 1H, J=11 Hz), 4.73 (s, 2H, HBn), 4.64 (d, 1H, J=5.5 Hz), 4.56-4.52 (m, 2H), 4.47-4.37 (m, 1H), 2.56-2.39 (m, 2H), 2.38-2.27 (m, 1H), 2.18-2.05 (m, 1H), 0.90 (s, 9H, Si(CH$_3$)$_3$), 0.08 (s, 6H, Si(CH$_3$)$_2$).

(2) Synthesis of Compound 12

Compound 12

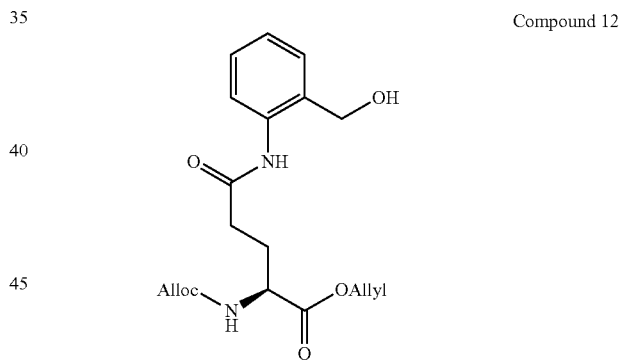

Compound 11 (1.29 g, 2.63 mmol) was dissolved in dehydrated THF (20 mL), TBAF (a. 1 mol/L in THF, 7.89 mL, 7.89 mmol) and acetic acid (304 μL, 5.26 mmol) were added, and the solution was stirred for three hours at room temperature. The end of the reaction was confirmed, water was added, and the solution was extracted twice by ethyl acetate. The ethyl acetate layer was washed with water and saturated saline, dried by sodium sulfate, and then concentrated. The residue was purified by silica gel chromatography (34 g silica gel, 50%→60% ethyl acetate/hexane), and the target substance was obtained as a colorless liquid (848 mg, 86%).

$^1$H NMR (CDCl$_3$, 400 MHz): δ8.73 (brs, 1H, —CONH—), 7.97 (d, 1H, J=8.2 Hz), 7.30 (dd, 1H, J=8.2 Hz, J=7.8 Hz), 7.18 (d, 1H, J=7.3 Hz), 7.07 (dd, 1H, J=7.3 Hz, J=7.3 Hz), 5.95-5.79 (m, 2H), 5.67 (brd, 1H, —OCONH—, J=7.8 Hz), 5.32 (d, 1H, J=17 Hz), 5.27 (d, 1H, J=17 Hz), 5.24 (d, 1H, J=10 Hz), 5.19 (d, 1H, J=10 Hz), 4.74-4.61 (m, 2H, HBn), 4.63 (d, 1H, J=6.0 Hz), 4.57-4.45 (m, 2H), 4.45-4.35 (m, 1H), 2.97 (brs, 1H, CH$_2$OH), 2.55-2.40 (m, 2H), 2.39-2.26 (m, 1H), 2.12-1.96 (m, 1H).

(3) Synthesis of Compound 13

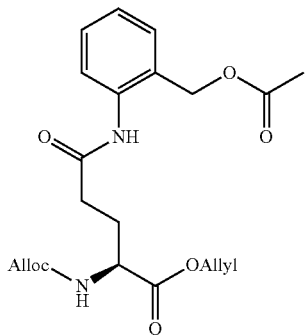

Compound 13

Compound 12 (29.6 mg, 0.0786 mmol) and triethylamine (110 μL, 0.786 mmol) were dissolved in dehydrated dichloromethane (1 mL), and acetic anhydride (15 μL, 0.157 mmol) was added and stirred for one hour at room temperature. The end of the reaction was confirmed, and the reaction solution was concentrated. The residue was refined by silica gel chromatography (14 g silica gel, 30%→40% ethyl acetate/hexane), and the target substance was obtained as a white solid (31.8 mg, 97%).

$^1$H NMR (CDCl$_3$, 400 MHz): δ8.86 (brs, 1H, —CONH—), 7.96 (d, 1H, J=7.8 Hz), 7.35 (dd, 1H, J=7.8 Hz, J=7.3 Hz), 7.34 (d, 1H, J=7.3 Hz), 7.13 (dd, 1H, J=7.8 Hz, J=7.3 Hz), 5.95-5.81 (m, 2H), 5.68 (brd, 1H, —OCONH—, J=7.3 Hz), 5.32 (d, 1H, J=17 Hz), 5.27 (d, 1H, J=17 Hz), 5.24 (d, 1H, J=11 Hz), 5.18 (d, 1H, J=11 Hz), 5.13 (d, 1H, HBn, J$_{gem}$=12 Hz), 5.08 (d, 1H, HBn', J$_{gem}$=12 Hz), 4.63 (d, 1H, J=5.5 Hz), 4.58-4.48 (m, 2H), 4.48-4.39 (m, 1H), 2.62-2.46 (m, 2H), 2.41-2.27 (m, 1H), 2.19-2.05 (m, 1H), 2.08 (s, 3H, OCOCH$_3$).

(4) Synthesis of Compound 14

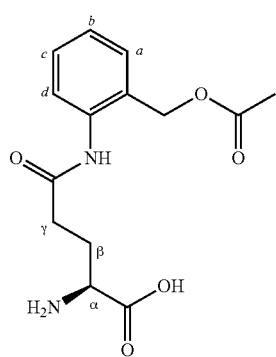

Compound 14

Compound 13 (31.7 mg, 0.0758 mmol) and phenyl silane (234 μL, 1.89 mmol) were dissolved in dehydrated dichloromethane (20 mL), and tetrakis(triphenylphosphine)palladium (21.8 mg, 0.0189 mmol) was added and stirred for two hours at room temperature. The end of the reaction was confirmed, and the reaction solution was concentrated. The residue was purified by reverse-phase HPLC (0%→100% acetonitrile/water), and the target substance was obtained as a white solid (8.0 mg, 36%).

$^1$H NMR (CD$_3$OD, 400 MHz) 7.40 (d, 1H, Ha, J$_{Ha\text{-}Hb}$=7.3 Hz), 7.38 (d, 1H, Hd, J$_{Hd\text{-}Hc}$=7.3 Hz), 7.32 (dd, 1H, Hc, J$_{Hc\text{-}Hb}$=J$_{Hc\text{-}Hd}$=7.3 Hz), 7.24 (dd, 1H, Hb, J$_{Hb\text{-}Ha}$=J$_{Hb\text{-}Hc}$=7.3 Hz), 5.09 (s, 2H, HBn), 3.63 (t, 1H, Hα, J$_{H\alpha\text{-}H\beta}$=6.2 Hz), 2.65 (t, 2H, Hγ, J$_{H\gamma\text{-}H\alpha}$=7.3 Hz), 2.18 (td, 2H, Hβ, J$_{H\beta\text{-}H\gamma}$=7.3 Hz, J$_{H\beta\text{-}H\alpha}$=6.2 Hz), 2.05 (s, 3H, CH$_3$COO—); $^{13}$C NMR (CD$_3$OD, 100 MHz): δ 172.3, 172.4, 171.4, 135.3, 131.1, 129.4, 128.6, 126.3, 126.1, 62.6, 54.3, 32.0, 26.5, 19.5; HRMS 317.11124 (M+Na$^+$).

(5) Synthesis of Compound 15

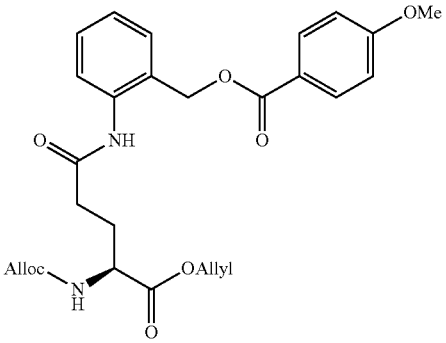

Compound 15

Compound 12 (35.1 mg, 0.0933 mmol) and DIPEA (96 μL, 0.560 mmol) and DMAP (3.5 mg) were dissolved in dehydrated dichloromethane (1 mL), and 4-methoxybenzoyl chloride (19 mg, 0.112 mmol) was added and stirred for four hours at room temperature. The end of the reaction was confirmed, saturated ammonium chloride aqueous solution was added, and the solution was extracted twice by ethyl acetate. The ethyl acetate layer was washed with saturated ammonium chloride aqueous solution and saturated saline, dried by sodium sulfate, and then concentrated. The residue was purified by silica gel chromatography (14 g silica gel, 20%→40% ethyl acetate/hexane), and the target substance was obtained as a white solid (43.2 mg, 91%).

$^1$H NMR (CDCl$_3$, 400 MHz): δ9.20 (brs, 1H, —CONH—), 8.00 (d, 2H, J=9.2 Hz), 8.00 (d, 1H, J=7.3 Hz), 7.43 (d, 1H, J=7.8 Hz), 7.37 (dd, 1H, J=7.8 Hz, J=7.3 Hz), 7.14 (dd, 1H, J=7.3 Hz, J=7.3 Hz), 6.90 (d, 2H, J=9.2 Hz), 5.95-5.82 (m, 2H), 5.71 (brd, 1H, —OCONH—, J=6.9 Hz), 5.35 (d, 1H, HBn, J$_{gem}$=12 Hz), 5.34 (d, 1H, J=19 Hz), 5.31 (d, 1H, HBn', J$_{gem}$=12 Hz), 5.27 (d, 1H, J=19 Hz), 5.23 (d, 1H, J=11 Hz), 5.17 (d, 1H, J=11 Hz), 4.63 (d, 1H, J=6.0 Hz), 4.58-4.50 (m, 2H), 4.50-4.41 (m, 1H), 3.85 (s, 3H, ArOCH$_3$), 2.67-2.52 (m, 2H), 2.42-2.30 (m, 1H), 2.24-2.07 (m, 1H).

(6) Synthesis of Compound 16

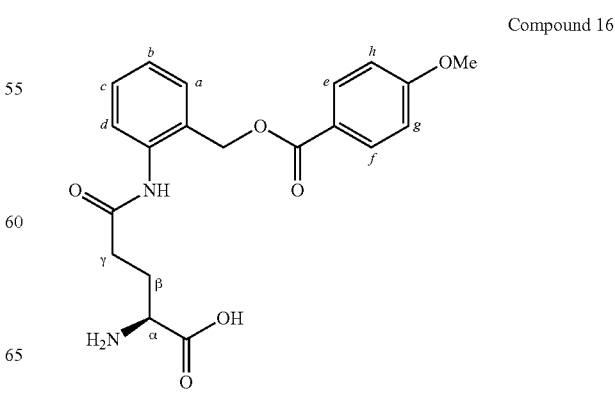

Compound 16

Compound 15 (26.4 mg, 0.0517 mmol) and phenyl silane (160 μL, 1.29 mmol) were dissolved in dehydrated dichloromethane (2 mL), and tetrakis(triphenylphosphine)palladium (14.9 mg, 0.0129 mmol) was added and stirred for three hours at room temperature. The end of the reaction was confirmed, and the reaction solution was concentrated. The residue was purified by reverse-phase HPLC (20%→100% acetonitrile/water), and the target substance was obtained as a white solid (7.8 mg, 39%).

$^1$H NMR (CD$_3$OD, 400 MHz) δ7.96 (d, 2H, He, Hf, $J_{He-Hh}$=$J_{Hf-Hg}$=9.2 Hz), 7.50 (d, 1H, Ha, $J_{Ha-Hb}$=7.3 Hz), 7.41 (d, 1H, Hd, $J_{Hd-Hc}$=6.9 Hz), 7.34 (dd, 1H, Hc, $J_{Hc-Hb}$=7.8 Hz, $J_{Hc-Hd}$=6.9 Hz), 7.26 (dd, 1H, Hb, $J_{Hb-Hc}$=7.8 Hz, $J_{Hb-Ha}$=7.3 Hz), 6.97 (d, 2H, Hg, Hh, $J_{hg-Hf}$=$J_{Hh-He}$=9.2 Hz), 5.32 (s, 2H, HBn), 3.83 (s, 3H, —OCH$_3$), 3.62 (t, 1H, Hα, $J_{Hα-Hβ}$=6.0 Hz), 2.66 (t, 2H, Hγ, $J_{Hγ-Hα}$=$J_{Hγ-Hβ}$=7.3 Hz), 2.17 (td, 2H, Hβ, $J_{Hβ-Hγ}$=7.3 Hz, $J_{Hβ-Hα}$=6.0 Hz); $^{13}$C NMR (CD$_3$OD, 100 MHz) δ172.9, 166.5, 164.0, 135.3, 131.4, 131.3, 129.4, 128.6, 126.4, 126.0, 122.0, 113.6, 62.8, 54.7, 54.4, 32.0, 26.5; HRMS 409.13271 (M+Na$^+$).

(7) Synthesis of Compound 17

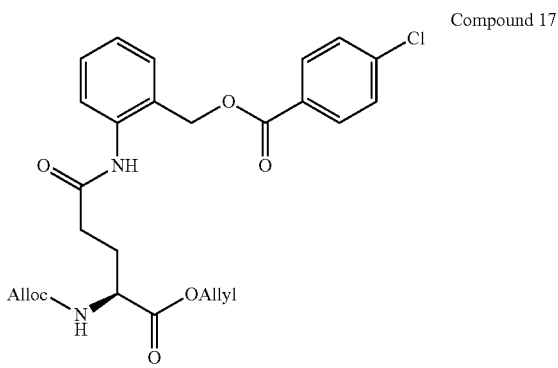

Compound 17

Compound 12 (29.7 mg, 0.0789 mmol) and DIPEA (82 μL, 0.473 mmol) and DMAP (3.0 mg) were dissolved in dehydrated dichloromethane (1 mL), and 4-chlorobenzoyl chloride (13 μL, 0.0947 mmol) was added and stirred for four hours at room temperature. The end of the reaction was confirmed, saturated ammonium chloride aqueous solution was added, and the solution was extracted twice by ethyl acetate. The ethyl acetate layer was washed with saturated ammonium chloride aqueous solution and saturated saline, dried by sodium sulfate, and then concentrated. The residue was purified by silica gel chromatography (14 g silica gel, 20%→40% ethyl acetate/hexane), and the target substance was obtained as a white solid (33.8 mg, 83%).

$^1$H NMR (CDCl$_3$, 400 MHz): δ9.02 (brs, 1H, —CONH—), 7.97 (d, 2H, J=8.7 Hz), 7.95 (d, 1H, J=7.3 Hz), 7.43 (d, 1H, J=7.8 Hz), 7.43 (d, 2H, J=8.7 Hz), 7.37 (dd, 1H, J=7.8 Hz, J=7.3 Hz), 7.16 (dd, 1H, J=7.3 Hz, J=7.3 Hz), 5.95-5.79 (m, 2H), 5.69 (brd, 1H, —OCONH—, J=7.8 Hz), 5.38 (d, 1H, HBn, $J_{gem}$=12 Hz), 5.35 (d, 1H, J=17 Hz), 5.33 (d, 1H, HBn', $J_{gem}$=12 Hz), 5.26 (d, 1H, J=17 Hz), 5.23 (d, 1H, J=9.6 Hz), 5.16 (d, 1H, J=9.6 Hz), 4.63 (d, 1H, J=6.0 Hz), 4.56-4.48 (m, 2H), 4.49-4.40 (m, 1H), 2.66-2.51 (m, 2H), 2.43-2.30 (m, 1H), 2.20-2.05 (m, 1H).

(8) Snthesis of Compound 18

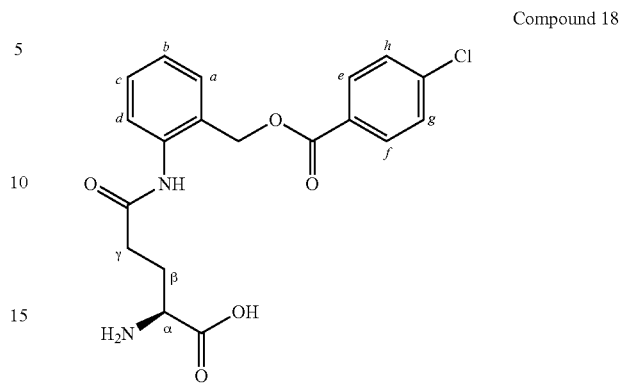

Compound 18

Compound 17 (33.7 mg, 0.0654 mmol) and phenyl silane (203 μL, 1.63 mmol) were dissolved in dehydrated dichloromethane (2 mL), and tetrakis(triphenylphosphine)palladium (18.9 mg, 0.0163 mmol) was added and stirred for three hours at room temperature. The end of the reaction was confirmed, and the reaction solution was concentrated. The residue was purified by reverse-phase HPLC (20%→100% acetonitrile/water), and the target substance was obtained as a white solid (3.8 mg, 15%).

$^1$H NMR (CD$_3$OD, 400 MHz) δ7.99 (d, 2H, He, Hf, $J_{He-Hh}$=$J_{Hf-Hg}$=7.8 Hz), 7.51 (d, 1H, Ha, $J_{Ha-Hb}$=7.8 Hz), 7.48 (d, 2H, Hg, Hh, $J_{Hg-Hf}$=$J_{Hh-He}$=7.8 Hz), 7.40 (d, 1H, Hd, $J_{Hd-Hc}$=7.8 Hz), 7.34 (dd, 1H, Hc, $J_{Hc-Hd}$=7.8 Hz, $J_{Hc-Hb}$=7.3 Hz), 7.27 (dd, 1H, Hb, $J_{Hb-Ha}$=7.8 Hz, $J_{Hb-Hc}$=7.3 Hz), 5.36 (s, 2H, HBn), 3.62 (t, 1H, Hα, $J_{Hα-Hβ}$=6.0 Hz), 2.66 (t, 2H, Hγ, $J_{Hγ-Hα}$=$J_{Hγ-Hβ}$=7.3 Hz), 2.16 (td, 2H, Hβ, $J_{Hβ-Hγ}$=7.3 Hz, $J_{Hβ-Hα}$=6.0 Hz); $^{13}$C NMR (CD$_3$OD, 100 MHz): δ172.9, 172.5, 165.6, 139.4, 135.4, 131.1, 130.9, 129.5, 128.8, 128.6, 126.5, 126.2, 63.3, 54.3, 32.0, 26.5; HRMS 413.08817 (M+Na$^+$).

(9) Synthesis of Compound 19

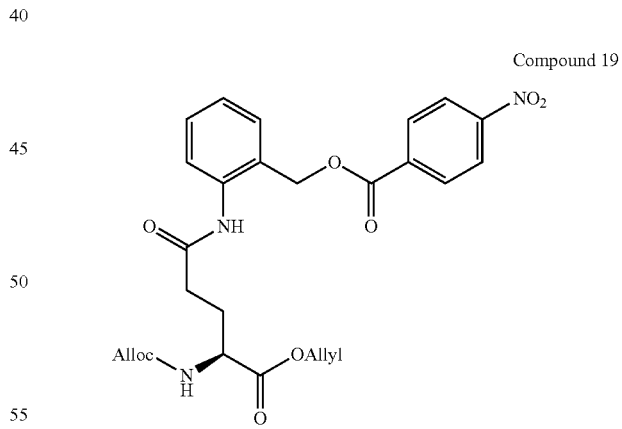

Compound 19

Compound 12 (31.5 mg, 0.0837 mmol) and DIPEA (87 μL, 0.502 mmol) and DMAP (3.2 mg) were dissolved in dehydrated dichloromethane (1 mL), and 4-nitrobenzoyl chloride (18.6 mg, 0.100 mmol) was added and stirred for one hour at room temperature. The end of the reaction was confirmed, saturated ammonium chloride aqueous solution was added, and the solution was extracted twice by ethyl acetate. The ethyl acetate layer was washed with saturated ammonium chloride aqueous solution and saturated saline, dried by sodium sulfate, and then concentrated. The residue was purified by silica gel chromatography (14 ag silica gel, 30%→40% ethyl acetate/hexane), and the target substance was obtained as a white solid (40.5 mg, 92%).

$^1$H NMR (CDCl$_3$, 400 MHz): δ 8.86 (brs, 1H, —CONH—), 8.27 (d, 2H, J=8.7 Hz), 8.21 (d, 2H, J=8.7 Hz), 7.91 (d, 1H, J=7.8 Hz), 7.45 (d, 1H, J=7.3 Hz), 7.38 (dd, 1H, J=7.8 Hz, J=7.3 Hz), 7.18 (dd, 1H, J=7.3 Hz, J=7.3 Hz), 5.95-5.78 (m, 2H), 5.67 (brd, 1H, —OCONH—, J=7.8 Hz), 5.44 (d, 1H, HBn, J$_{gem}$=12 Hz), 5.39 (d, 1H, HBn', H$_{gem}$=12 Hz), 5.31 (d, 1H, J=17 Hz), 5.25 (d, 1H, J=17 Hz), 5.23 (d, 1H, J=11 Hz), 5.16 (d, 1H, J=11 Hz), 4.63 (d, 1H, J=6.0 Hz), 4.56-4.39 (m, 3H), 2.65-2.51 (m, 2H), 2.43-2.29 (m, 1H), 2.20-2.03 (m, 1H).

(10) Synthesis of Compound 20 (N$^5$-(2-(((4-nitrobenzoyl)oxy)methyl)phenyl)-L-glutamine)

Compound 20

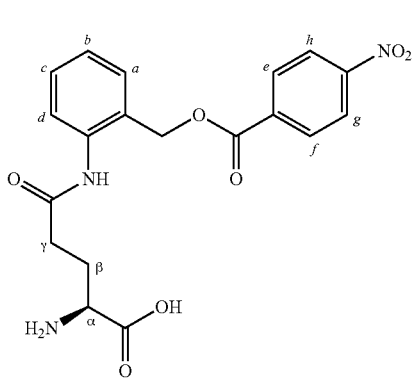

Compound 19 (40.5 mg, 0.0771 mmol) and phenyl silane (239 μL, 1.92 mmol) were dissolved in dehydrated dichloromethane (2 mL), and tetrakis(triphenylphosphine)palladium (22.3 mg, 0.0192 mmol) was added and stirred for two hours at room temperature. The end of the reaction was confirmed, and the reaction solution was concentrated. The residue was purified by reverse-phase HPLC (20%→100% acetonitrile/water), and the target substance was obtained as a white solid (6.3 mg, 20%).

$^1$H NMR (CD$_3$OD, 400 MHz): δ 8.31 (d, 2H, He, Hf, J$_{He-Hh}$=J$_{Hf-Hg}$=9.2 Hz), 8.22 (d, 2H, Hg, Hh, J$_{Hg-Hf}$=J$_{Hh-He}$=9.2 Hz), 7.53 (d, 1H, Ha, J$_{Ha-Hb}$=7.3 Hz), 7.40-7.34 (m, 2H, Hc, Hd), 7.29 (ddd, 1H, Hb, J$_{Hb-Ha}$=J$_{Hb-Hc}$=7.3 Hz, J$_{Hb-Hd}$=1.8 Hz), 5.41 (s, 2H, HBn), 3.62 (t, 1H, Hα, J$_{Hα-Hβ}$=6.0 Hz), 2.66 (t, 2H, Hγ, J$_{Hγ-Hα}$=J$_{Hγ-Hβ}$=7.3 Hz), 2.16 (td, 2H, Hβ, J$_{Hβ-Hγ}$=7.3 Hz, J$_{Hβ-Hα}$=6.0 Hz); $^{13}$C NMR (CD$_3$OD, 100 MHz): δ 173.0, 172.5, 164.7, 150.8, 135.5, 130.9, 130.5, 129.7, 129.0, 128.0, 127.6, 126.5, 125.6, 124.6, 123.3, 63.9, 54.3, 32.0, 26.6; HRMS 413.11126 (M+Na$^+$).

(11) Synthesis of Compound 21

Compound 21

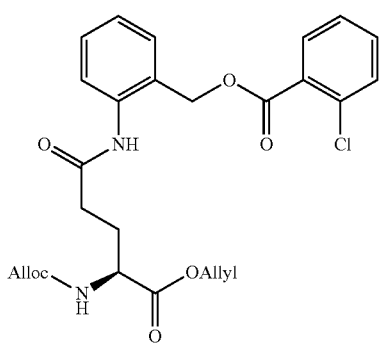

Compound 12 (30.8 mg, 0.0818 mmol) and DIPEA (85 μL, 0.491 mmol) and DIMAP (3.1 mg) were dissolved in dehydrated dichloromethane (1 mL), and 2-chlorobenzoyl chloride (12.4 μL, 0.0978 mmol) was added and stirred for 1.5 hour at room temperature. The end of the reaction was confirmed, saturated ammonium chloride aqueous solution was added, and the solution was extracted twice by ethyl acetate. The ethyl acetate layer was washed with saturated ammonium chloride aqueous solution and saturated saline, dried by sodium sulfate, and then concentrated. The residue was purified by silica gel chromatography (14 silica gel, 20%→30% ethyl acetate/hexane), and the target substance was obtained as a white solid (27.3 mg, 6%).

$^1$H NMR (CDCl$_3$, 400 MHz): δ 8.74 (brs, 1H, —CONH—), 7.94 (d, 1H, J=8.2 Hz), 7.83 (d, 1H, J=7.6 Hz), 7.47-7.41 (m, 3H), 7.37 (ddd, 1H, J=7.8 Hz, J=7.8 Hz, J=1.4 Hz), 7.30 (ddd, 1H, J=7.3 Hz, J=6.9 Hz, J=1.8 Hz), 7.16 (dd, 1H, J=7.3 Hz, J=7.3 Hz), 5.95-5.80 (m, 2H), 5.66 (brd, 1H, —OCONH—, J=7.8 Hz), 5.40 (d, 1H, HBn, J$_{gem}$=12 Hz), 5.36 (d, 1H, HBn', J$_{gem}$=12 Hz), 5.31 (d, 1H, J=17 Hz), 5.26 (d, 1H, J=17 Hz), 5.22 (d, 1H, J=11 Hz), 5.16 (d, 1H, J=11 Hz), 4.63 (d, 1H, J=6.0 Hz), 4.58-4.49 (m, 2H), 4.49-4.39 (m, 1H), 2.67-2.50 (m, 2H), 2.44-2.30 (m, 1H), 2.18-2.04 (m, 1H).

(12) Synthesis of Compound 22

Compound 22

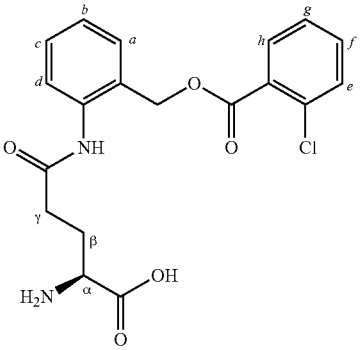

Compound 21 (27.3 mg, 0.0530 mmol) and phenyl silane (164 μL, 1.32 mmol) were dissolved in dehydrated dichloromethane (2 mL), and tetrakis(triphenylphosphine)palladium (15.3 mg, 0.0132 mmol) was added and stirred for one hour at room temperature. The end of the reaction was confirmed, and the reaction solution was concentrated. The residue was purified by reverse-phase HPLC (20%→100% acetonitrile/water), and the target substance was obtained as a white solid (11.1 mg, 54%).

$^1$H NMR (CD$_3$OD, 400 MHz): δ 7.81 (d, 1H, He, J$_{He-Hf}$=7.3 Hz), 7.53 (d, 1H, Ha, J$_{Ha-Hb}$=7.3 Hz), 7.49-7.48 (m, 2H, Hc, Hd), 7.41-7.34 (m, 3H, Hb, Hg, Hh), 7.29 (dd, 1H, Hb, J$_{Hb-Ha}$=J$_{Hb-Hc}$=7.3 Hz), 5.37 (s, 2H, HBn), 3.63 (t, 1H, Hα, J$_{Hα-Hβ}$=6.0 Hz), 2.67 (t, 2H, Hγ, J$_{Hγ-Hα}$=J$_{Hγ-Hβ}$=7.3 Hz), 2.18 (td, 2H, Hβ, J$_{Hβ-Hγ}$=7.3 Hz, J$_{Hβ-Hα}$=6.0 Hz); $^{13}$C NMR (CD$_3$OD, 100 MHz): δ 172.9, 172.7, 135.4, 133.1, 132.6, 131.1, 130.8, 130.7, 130.1, 129.6, 128.8, 126.7, 126.4, 126.1, 63.6, 54.4, 32.0, 26.6; HRMS 413.08882 (M+Na$^+$).

(13) Synthesis of Compound 23

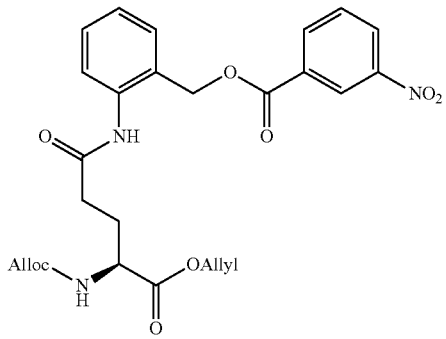

Compound 23

Compound 12 (32.2 mg, 0.0855 mmol) and DIPEA (89 μL, 0.513 mmol) and DMAP (3.2 mg) were dissolved in dehydrated dichloromethane (1 mL), and 3-nitrobenzoyl chloride (14 μL, 0.103 mmol) was added and stirred for three hours at room temperature. The end of the reaction was confirmed, saturated ammonium chloride aqueous solution was added, and the solution was extracted twice by ethyl acetate. The ethyl acetate layer was washed with saturated ammonium chloride aqueous solution and saturated saline, dried by sodium sulfate, and then concentrated. The residue was purified by silica gel chromatography (14 g silica gel, 30%→50% ethyl acetate/hexane), and the target substance was obtained as a white solid (37.8 mg, 84%).

$^1$H NMR (CDCl$_3$, 400 MHz): δ 8.90 (brs, 1H, —CONH—), 8.85 (s, 1H), 8.41 (dd, 1H, J=8.0 Hz, J=2.3 Hz), 8.36 (d, 1H, J=7.8 Hz), 7.91 (d, 1H, J=7.8 Hz), 7.65 (dd, 1H, J=8.2 Hz, J=7.8 Hz), 7.47 (d, 1H, J=7.8 Hz), 7.38 (dd, 1H, J=7.8 Hz, J=7.3 Hz), 7.18 (dd, 1H, J=7.3 Hz, J=7.3 Hz), 5.95-5.78 (m, 2H), 5.68 (brd, 1H, —OCONH—, J=7.8 Hz), 5.45 (d, 1H, HBn, J$_{gem}$=12 Hz), 5.40 (d, 1H, HBn', J$_{gem}$=12 Hz), 5.31 (d, 1H, J=17 Hz), 5.25 (d, 1H, J=17 Hz), 5.23 (d, 1H, J=11 Hz), 5.15 (d, 1H, J=11 Hz), 4.63 (d, 1H, J=6.0 Hz), 4.56-4.40 (m, 2H), 2.67-2.51 (m, 2H), 2.44-2.30 (m, 1H), 2.22-2.05 (m, 1H).

(14) Synthesis of Compound 24

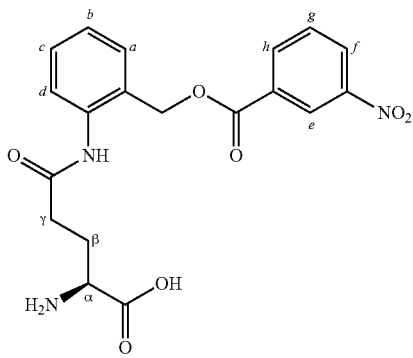

Compound 24

Compound 23 (36.9 mg, 0.0702 mmol) and phenyl silane (217 μL, 1.76 mmol) were dissolved in dehydrated DMF (2 mL), and tetrakis(triphenylphosphine)palladium (20.3 mg, 0.0176 mmol) was added and stirred for two hours at room temperature. The end of the reaction was confirmed, the reaction solution was purified as it was by reverse-phase HPLC (20%→100% acetonitrile/water), and the target substance was obtained as a white solid (10.0 mg, 35%).

$^1$H NMR (CD$_3$OD, 400 MHz): δ 8.78 (s, 1H, He), 8.45 (d, 1H, Hh, J$_{Hh-Hg}$=8.2 Hz), 8.39 (d, 1H, Hf, J$_{Hf-Hg}$=7.6 Hz), 7.75 (dd, 1H, Hg, J$_{Hg-Hh}$=8.2 Hz, J$_{Hg-Hf}$=7.6 Hz), 7.54 (d, 1H, Ha, J$_{Ha-Hb}$=7.3 Hz), 7.43-7.35 (m, 2H, Hc, Hd), 7.41-7.34 (m, 3H, Hb, Hg, Hh), 7.30 (dd, 1H, Hb, J$_{Hb-Ha}$=J$_{Hb-Hc}$=7.3 Hz), 5.43 (s, 2H, HBn), 3.60 (t, 1H, Hα, J$_{Hα-Hβ}$=6.0 Hz), 2.66 (t, 2H, Hγ, J$_{Hγ-Hα}$=J$_{Hγ-Hβ}$=7.3 Hz), 2.16 (td, 2H, Hβ, J$_{Hβ-Hγ}$=7.3 Hz, J$_{Hβ-Hα}$=6.0 Hz); $^{13}$C NMR (CD$_3$OD, 100 MHz): no data; HRMS 424.11063 (M+Na$^+$).

(15) Synthesis of Compound 25

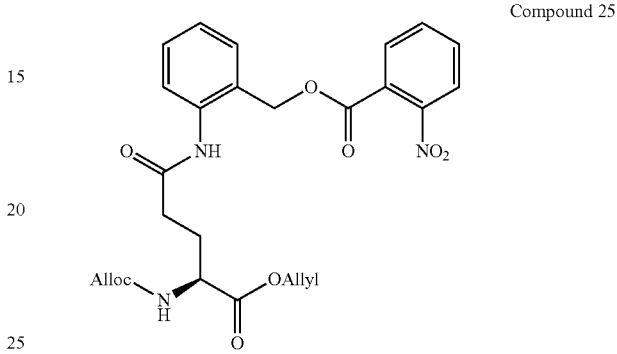

Compound 25

Compound 12 (37.3 mg, 0.0991 mmol) and DIPEA (103 μL, 0.595 mmol) and DMAP (3.7 mg) were dissolved in dehydrated dichloromethane (1 mL), and 2-nitrobenzoyl chloride (16 μL, 0.119 mmol) was added and stirred for 1.5 hour at room temperature. The end of the reaction was confirmed, saturated ammonium chloride aqueous solution was added, and the solution was extracted twice by ethyl acetate. The ethyl acetate layer was washed with saturated ammonium chloride aqueous solution and saturated saline, dried by sodium sulfate, and then concentrated. The residue was purified by silica gel chromatography (14 g silica gel, 30%→50% ethyl acetate/hexane), and the target substance was obtained as a white solid (40.5 mg, 78%).

$^1$H NMR (CDCl$_3$, 400 MHz): δ 8.23 (brs, 1H, —CONH—), 7.91 (d, 1H, J=7.8 Hz), 7.74 (d, 1H, J=8.0 Hz), 7.71-7.60 (m, 2H), 7.38 (dd, 1H, J=7.8 Hz, J=7.3 Hz), 7.37 (d, 1H, J=7.3 Hz), 7.16 (dd, 1H, J=7.3 Hz, J=7.3 Hz), 5.95-5.80 (m, 2H), 5.69 (brd, 1H, —OCONH—, J=7.8 Hz), 5.38 (d, 1H, HBn, J$_{gem}$=12 Hz), 5.31 (d, 1H, HBn', J$_{gem}$=12 Hz), 5.31 (d, 1H, J=17 Hz), 5.26 (d, 1H, J=17 Hz), 5.22 (d, 1H, J=11 Hz), 5.15 (d, 1H, J=11 Hz), 4.63 (d, 1H, J=6.0 Hz), 4.58-4.40 (m, 2H), 2.68-2.53 (m, 2H), 2.42-2.30 (m, 1H), 2.18-2.20 (m, 1H).

(16) Synthesis of Compound 26

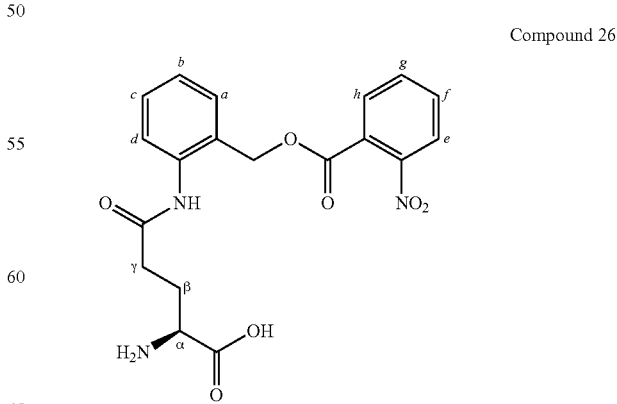

Compound 26

Compound 25 (40.2 mg, 0.0765 mmol) and phenyl silane (236 μL, 1.91 mmol) were dissolved in dehydrated dichloromethane (2 mL), and tetrakis(triphenylphosphine)palladium (22.1 mg, 0.0191 mmol) was added and stirred for one hour at room temperature. The end of the reaction was confirmed, the reaction solution was purified without further modification by reverse-phase HPCL (20%→100% acetonitrile/water), and the target substance was obtained as a white solid (7.2 mg, 23%).

$^1$H NMR (CD$_3$OD, 400 MHz): δ 7.94 (d, 1H, He, $J_{He-Hf}$=7.8 Hz), 7.82-7.69 (m, 3H, Hf, Hg, Hh), 7.46 (d, 1H, Ha, $J_{Ha-Hb}$=7.3 Hz), 7.42-7.33 (m, 2H, Hc, Hd), 7.27 (dd, 1H, Hb, $J_{Hb-Ha}$=$J_{Hb-Hc}$=7.3 Hz), 5.34 (s, 2H, HBn), 3.63 (t, 1H, Hα, $J_{Hα-Hβ}$=5.3 Hz), 2.69 (t, 2H, Hγ, $J_{Hγ-Hα}$=$J_{Hγ-Hβ}$=6.6 Hz), 2.18 (td, 2H, Hβ, $J_{Hβ-Hγ}$=6.6 Hz, $J_{Hβ-Hα}$=5.3 Hz); $^{13}$C NMR (CD$_3$OD, 100 MHz): 173.0, 172.6, 165.3, 135.5, 133.0, 132.3, 130.2, 129.8, 129.0, 126.9, 126.4, 126.1, 123.8, 64.4, 54.4, 32.0, 26.5; HRMS 424.11207 (M+Na$^+$).

Example 5

(1) Confirmation of Enzyme Recognition Capacity Using Benzyl-Position Leaving Group-Converted Derivatives Next, enzymatic reactions were carried out under the following conditions using the benzyl-position leaving group-converted derivatives synthesized and purified enzyme.

Final compound concentration: 100 μM

Final enzyme concentration: 10 U/mL (GGT)

Reaction temperature: 37° C.

Enzymatic reaction using GGT

Instrument: 1260 Infinity (manufactured by Agilent Technologies, Inc.)

Column: Poroshell 120, 4.6×100 mm (manufactured by Agilent Technologies, Inc.)

Mobile phase A: water (0.01M ammonium formate)

Mobile phase B: 80% acetonitrile/water (0.01M ammonium formate)

Gradient: A/B: 95/5-50/50, 20 min

The results are shown in FIG. 12. FIG. 12 shows, from the top of each graph, chromatograms of the mass peak of the raw material after 0 hours and after one hour and chromatograms of the mass peak of the enzyme reaction product after 0 hours and after one hour.

The results in FIG. 12 confirmed that the derivative group having acyl-based leaving groups releases azaquinone methides, although at different rates depending on the purified GGT.

(2) In Vitro Efficacy Study Using Benzyl-Position Leaving Group-Converted Derivatives (CCK-8 Assay)

Next, benzyl-position leaving group-converted derivatives were subjected to the CCK-8 assay described above. The results are shown in FIG. 13.

As shown in FIG. 13, none of the derivatives having an acyl-based leaving group showed antitumor activity at a concentration of 25 μM at which the model compound in which the leaving group is a fluorine showed an effect.

Synthesis of Benzene Ring Substituent-Converted Derivatives

In addition, the following four compounds having substituents introduced as the 4 and 5 positions on the benzene ring were synthesized as GGT prodrug derivatives. An effect on cell death is also expected because introduction of a methyl group (electron donating group) and methyl ester group (electron withdrawing group) changes the electron density of the benzene ring and changes the reactivity of the azaquinone methides released.

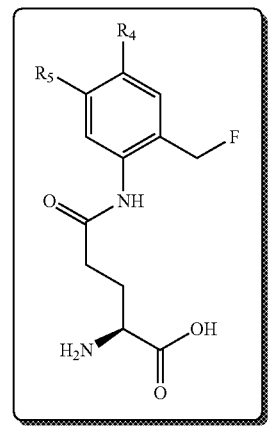

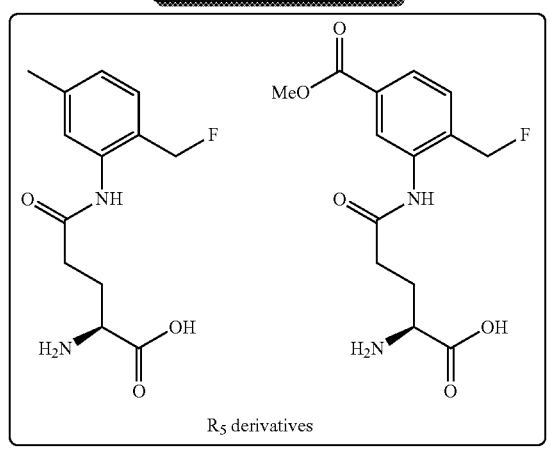

R$_5$ derivatives

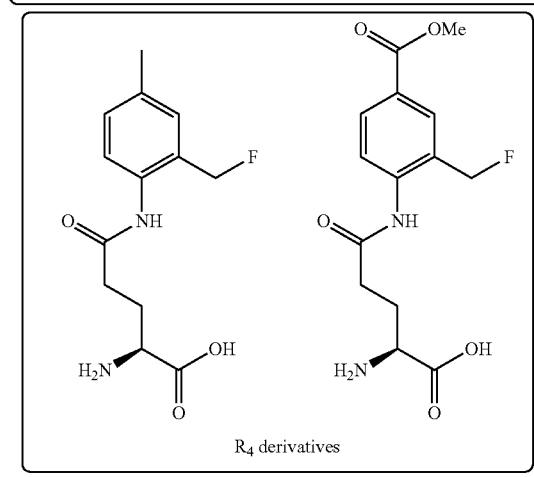

R$_4$ derivatives

Synthesis Example 5

4-Substituted compounds were synthesized according to synthesis scheme 5 below.

(Scheme 5)

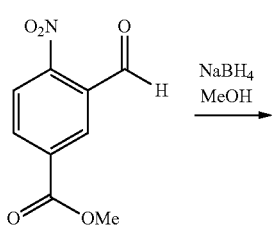

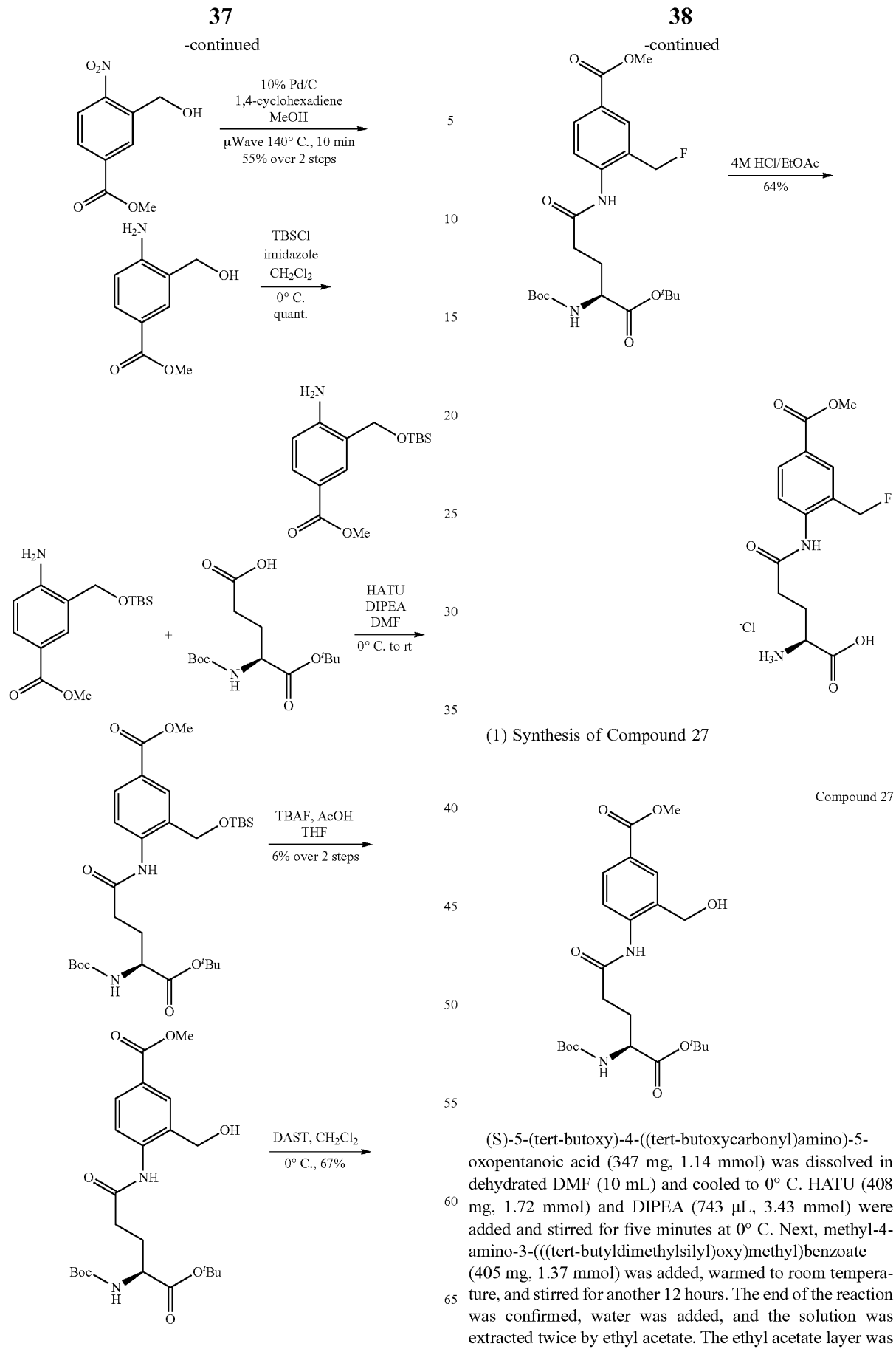

(1) Synthesis of Compound 27

Compound 27

(S)-5-(tert-butoxy)-4-((tert-butoxycarbonyl)amino)-5-oxopentanoic acid (347 mg, 1.14 mmol) was dissolved in dehydrated DMF (10 mL) and cooled to 0° C. HATU (408 mg, 1.72 mmol) and DIPEA (743 μL, 3.43 mmol) were added and stirred for five minutes at 0° C. Next, methyl-4-amino-3-(((tert-butyldimethylsilyl)oxy)methyl)benzoate (405 mg, 1.37 mmol) was added, warmed to room temperature, and stirred for another 12 hours. The end of the reaction was confirmed, water was added, and the solution was extracted twice by ethyl acetate. The ethyl acetate layer was washed with water and saturated sodium bicarbonate aqueous solution and saturated saline, dried by sodium sulfate, and then concentrated. The residue was purified by silica gel chromatography (34 g silica gel 10%→20% ethyl acetate/hexane), and the target substance was obtained as a mixture (197 mg). This mixture was dissolved in dehydrated THF (5 mL), and TBAF (ca. 1 mol/L in THF, 1 mL, 1.00 mmol) and acetic acid (46 μL, 0.678 mmol) were added and stirred for one hour at room temperature. The end of the reaction was confirmed, saturated ammonium chloride aqueous solution was added, and the solution was extracted twice by ethyl acetate. The ethyl acetate layer was washed with water and saturated saline, dried by sodium sulfate, and then concentrated. The residue was purified by silica gel chromatography (14 g silica gel, 40%→60% ethyl acetate/hexane), and the target substance was obtained as a colorless liquid (39.9 mg, 2-step 6%).

$^1$H NMR (CDCl$_3$, 400 MHz): δ 9.16 (brs, 1H, —CONH—), 8.24 (d, 1H, J=8.2 Hz), 7.97 (d, 1H, J=8.2 Hz), 7.85 (s, 1H), 5.31 (brd, 1H, —OCONH—, J=7.3 Hz), 4.84-4.64 (m, 2H, HBn), 4.27-4.15 (m, 1H), 3.88 (s, 3H, ArCOOCH$_3$), 3.26-3.18 (m, 1H, CH$_2$OH), 2.36-2.22 (m, 1H), 2.03-1.88 (m, 1H), 1.45 (s, 9H, COO(CH$_3$)$_3$), 1.41 (s, 9H, NHCOO(CH$_3$)$_3$).

(2) Synthesis of Compound 28

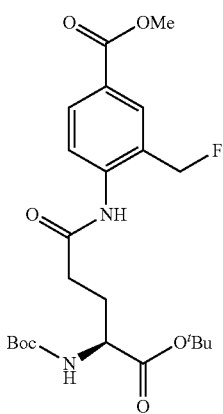

Compound 28

Compound 27 (38.6 mg, 0.0824 mmol) was dissolved in dehydrated dichloromethane (2 mL) and cooled to 0° C. DAST (54 μL, 0.412 mmol) was added and stirred for one hour at room temperature. The end of the reaction was confirmed, saturated sodium bicarbonate aqueous solution was added, and the solution was extracted twice by ethyl acetate. The ethyl acetate layer was washed with saturated sodium bicarbonate aqueous solution and saturated saline, dried by sodium sulfate, and then concentrated. The residue was purified by silica gel chromatography (34 g silica gel, 20%→60% ethyl acetate/hexane), and the target substance was obtained as a colorless liquid (25.9 mg, 67%).

$^1$H NMR (CDCl$_3$, 400 MHz): δ 8.48 (brs, 1H, —CONH—), 8.23 (d, 1H, J=8.2 Hz), 8.07 (d, 1H, J=8.2 Hz), 7.99 (s, 1H), 5.70-5.38 (m, 2H, HBn), 5.30 (brs, 1H, —OCONH—), 4.28-4.18 (m, 1H), 3.91 (s, 3H, ArCOOCH$_3$), 2.62-2.42 (m, 2H), 2.40-2.26 (m, 1H), 2.20-1.82 (m, 1H), 1.46 (s, 9H, COO(CH$_3$), 1.44 (s, 9H, NHCOO(CH$_3$)$_3$).

(3) Synthesis of Compound 29

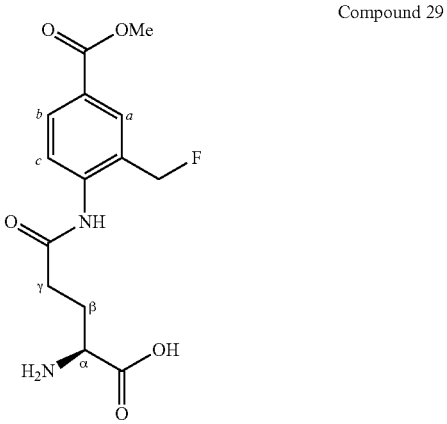 [SMILES: COC(=O)c1ccc(NC(=O)CC[C@H](N)C(=O)O)c(CF)c1]

Compound 29

Compound 28 (29.5 mg, 0.0553 mmol) was dissolved in 4M hydrochloric acid/ethyl acetate (2 mL) and stirred for 12 hours at room temperature. The end of the reaction was confirmed, and the reaction solution was concentrated. The residue was purified by reverse-phase HPLC (0%→100% acetonitrile/water), and the target substance was obtained as a white solid (11 mg, 64%).

$^1$H NMR (CD$_3$OD, 400 MHz): δ 8.09 (s, 1H, Ha), 7.99 (d, 1H, Hb, J$_{Hb-Hc}$=8.7 Hz), 7.66 (d, 1H, Hb, J$_{Hb-Hc}$=8.7 Hz), 5.44 (d, 2H, HBn, J$_{HBn-F}$=48 Hz), 4.06 (t, 1H, Hα, J$_{Hα-Hβ}$=6.4 Hz), 3.89 (s, 3H, ArCOOCH$_3$), 2.76 (t, 2H, Hγ, J$_{Hγ-Hα}$=6.9 Hz), 2.25 (tt, 2H, Hβ, J$_{Hβ-Hγ}$=6.9 Hz, J$_{Hβ-Hα}$=6.4 Hz); $^{13}$C NMR (CD$_3$OD, 100 MHz): δ 173.1, 171.4, 167.7, 140.7, 131.9, 131.4, 131.0, 128.7, 126.0, 82.2 (d, CH$_2$F, J$_{C-F}$=164 Hz), 53.4, 52.7, 32.7, 26.8; HRMS 335.10105 (M+Na$^+$).

Synthesis Example 6

A 4-substituted form was synthesized according to synthesis scheme 6 below.

(Scheme 6)

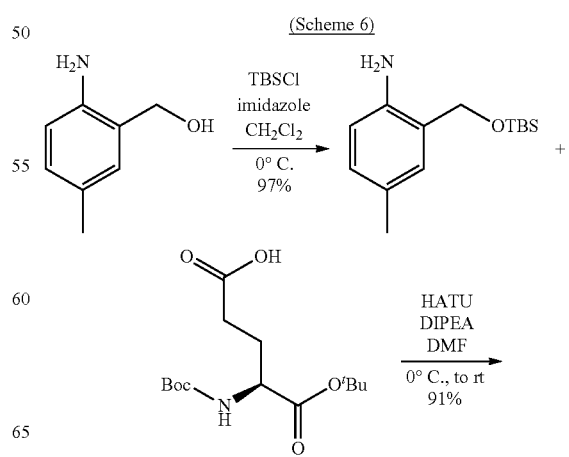

-continued

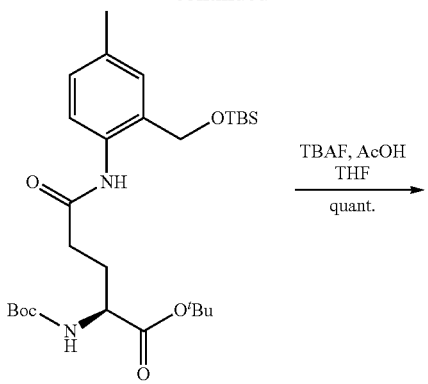

TBAF, AcOH
THF
quant.

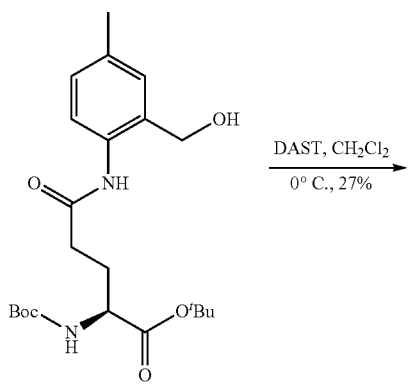

DAST, CH₂Cl₂
0° C., 27%

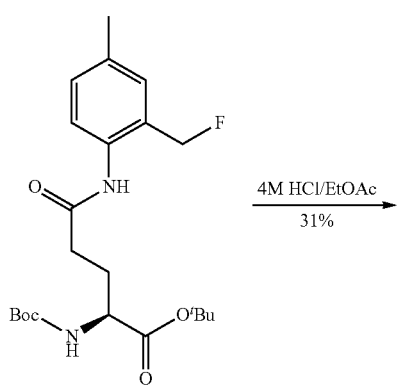

4M HCl/EtOAc
31%

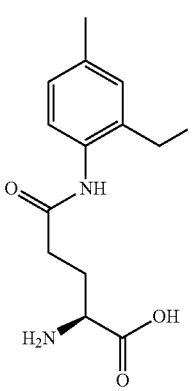

(1) Synthesis of Compound 30

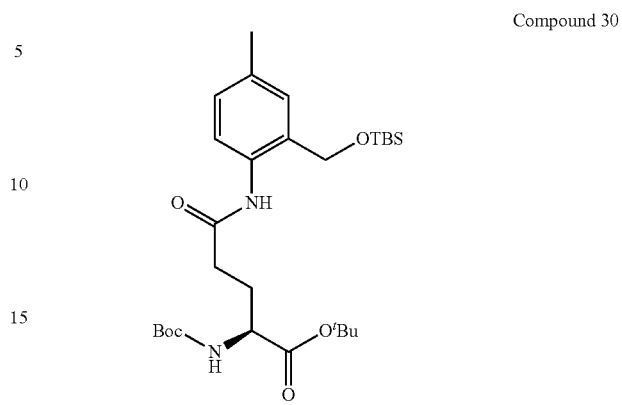

Compound 30

(S)-5-(tert-butoxy)-4-((tert-butoxycarbonyl)amino)-5-oxopentanoic acid (811 mg, 2.67 mmol) was dissolved in dehydrated DMF (20 mL) and cooled to 0° C. HATU (952 mg, 4.01 mmol) and DIPEA (174 µL, 8.02 mmol) were added and stirred for five minutes at 0° C. Next, 2-(tert-butyldimethylsilyl)oxy)methyl)-4-methylaniline (807 mg, 3.21 mmol) was added, warmed to room temperature, and stirred for another 12 hours. The end of the reaction was confirmed, water was added, and the solution was extracted twice by ethyl acetate. The ethyl acetate layer was washed with water and saturated sodium bicarbonate aqueous solution and saturated saline, dried by sodium sulfate, and then concentrated. The residue was purified by silica gel chromatography (34 g silica gel, 10%→20% ethyl acetate/hexane), and the target substance was obtained as a colorless liquid (1.31 g, 91%).

¹H NMR (CDCl₃, 400 MHz): δ 8.78 (brs, 1H, —CONH—), 8.00 (d, 1H, J=7.8 Hz), 7.09 (d, 1H, J=7.8 Hz), 6.91 (s, 1H), 5.21 (brd, 1H, —OCONH—, J=7.8 Hz), 4.70 (d, 1H, HBn, $J_{gem}$=13 Hz), 4.67 (d, 1H, HBn', $J_{gem}$=13 Hz), 4.28-4.14 (m, 1H), 2.52-2.33 (m, 2H), 2.32-2.18 (m, 1H), 2.29 (s, 3H, ArCH₃), 2.06-1.92 (m, 1H), 1.46 (s, 9H, COO(CH₃)), 1.42 (s, 9H, NHCOO(CH₃)), 0.90 (s, 9H, Si(CH₃)₃), 0.08 (s, 6H, Si(CH₃)₂).

(2) Synthesis of Compound 31

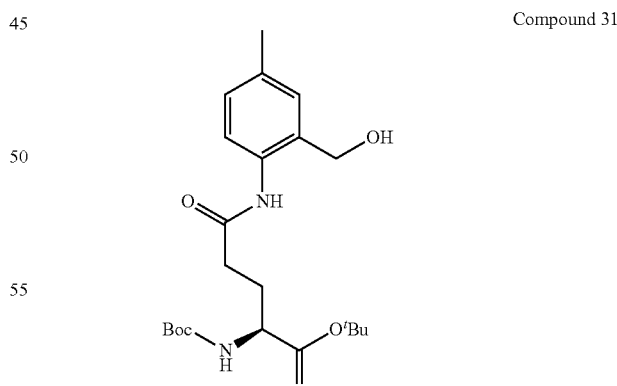

Compound 31

Compound 30 (1.31 g, 2.43 mmol) was dissolved in dehydrated THF (14 mL), and TBAF (ca. 1 mol/L in THF, 7.3 mL, 7.3 mmol) and acetic acid (329 µL, 4.87 mmol) were added and stirred for one hour at room temperature. The end of the reaction was confirmed, water was added, and the solution was extracted twice by ethyl acetate. The ethyl acetate layer was washed with water and saturated saline, dried by sodium sulfate, and then concentrated. The residue was purified by silica gel chromatography (34 g silica gel, 40%→60% ethyl acetate/hexane), and the target substance was obtained as a colorless liquid (1.03 g, quantitative).

$^1$H NMR (CDCl$_3$, 400 MHz): δ 8.75 (brs, 1H, —CONH—), 7.68 (d, 1H, J=7.8 Hz), 7.07 (d, 1H, J=7.8 Hz), 7.01 (s, 1H), 5.36 (brd, 1H, —OCONH—, J=8.2 Hz), 4.60 (d, 1H, HBn, J$_{gem}$=13 Hz), 4.54 (d, 1H, HBn', J$_{gem}$=13 Hz), 4.22-4.10 (m, 1H), 2.48-2.32 (m, 2H), 2.32-2.06 (m, 1H), 2.27 (s, 3H, ArCH$_3$), 2.20-1.82 (m, 1H), 1.44 (s, 9H, COO(CH$_3$), 1.40 (s, 9H, NHCOO(CH$_3$)$_3$).

(3) Synthesis of Compound 32

Compound 32

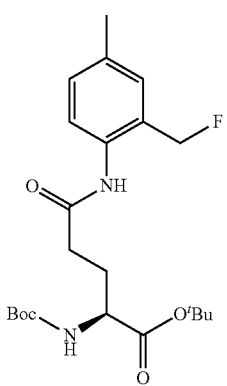

Compound 31 (476 mg, 1.13 mmol) was dissolved in dehydrated dichloromethane (10 mL) and cooled to 0° C. DAST (738 µL, 5.63 mmol) was added and stirred for one hour. The end of the reaction was confirmed, saturated sodium bicarbonate aqueous solution was added, and the solution was extracted twice by ethyl acetate. The ethyl acetate layer was washed with saturated sodium bicarbonate aqueous solution and saturated saline, dried by sodium sulfate, and then concentrated. The residue was purified by silica gel chromatography (34 g silica gel, 20%→30% ethyl acetate/hexane), and the target substance was obtained as a colorless liquid (129 mg, 27%).

$^1$H NMR (CDCl$_3$, 400 MHz): δ 8.14 (brs, 1H, —CONH—), 7.68 (d, 1H, J=8.2 Hz), 7.17 (d, 1H, J=8.2 Hz), 7.12 (s, 1H), 5.38 (d, 2H, HBn, J$_{HBn\text{-}F}$=48 Hz, J$_{gem}$=11 Hz), 5.30 (brd, 1H, —OCONH—, J=6.0 Hz), 4.32-4.16 (m, 1H), 2.56-2.36 (m, 2H), 2.36-2.20 (m, 1H), 2.31 (s, 3H, ArCH$_3$), 2.20-1.84 (m, 1H), 1.45 (s, 9H, COO(CH$_3$), 1.43 (s, 9H, NHCOO(CH$_3$).

(4) Synthesis of Compound 33

Compound 33

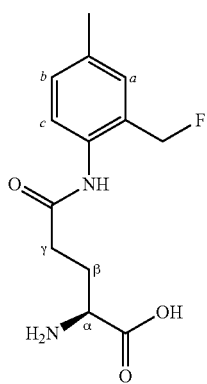 [SMILES: Cc1ccc(NC(=O)CC[C@H](N)C(=O)O)c(CF)c1]

Compound 32 (38.5 mg, 0.0907 mmol) was dissolved in 4M hydrochloric acid/ethyl acetate (1 mL) and stirred for 12 hours at room temperature. The end of the reaction was confirmed, and the reaction solution was concentrated. The residue was purified by reverse-phase HPLC (0%→100% acetonitrile/water), and the target substance was obtained as a white solid (7.5 mg, 31%).

$^1$H NMR (CD$_2$Cl$_2$, 400 MHz): δ 7.26 (s, 1H), 7.23 (d, 1H, Hc, J$_{Hc\text{-}Hb}$=7.8 Hz), 7.17 (d, 1H, Hb, J$_{Hb\text{-}Hc}$=7.8 Hz), 5.32 (d, 2H, HBn, J$_{HBn\text{-}F}$=48 Hz), 3.62 (t, 1H, Hα, J$_{H\alpha\text{-}H\beta}$=6.0 Hz), 2.63 (t, 2H, Hγ, J$_{H\gamma\text{-}H\beta}$=7.3 Hz), 2.33 (s, 3H, ArCH$_3$), 2.22-2.10 (m, 2H, Hβ); $^{13}$C NMR (CD$_3$OD, 100 MHz): δ 174.2, 173.6, 137.7, 133.6, 132.8, 130.8, 130.2, 127.2, 82.5 (d, CH$_2$F, J$_{C\text{-}F}$=163 Hz), 55.4, 33.2, 27.8, 21.0; HRMS 269.13277 (M+H$^+$).

Synthesis Example 7

Next, a 5-substituted form was synthesized according to scheme 7 below.

(Scheme 7)

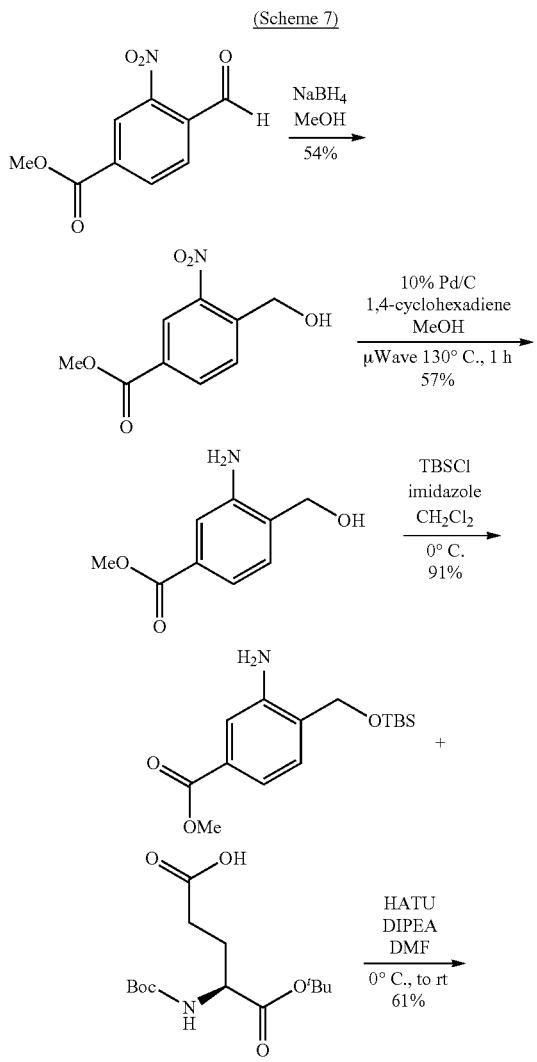

(1) Synthesis of Compound 34

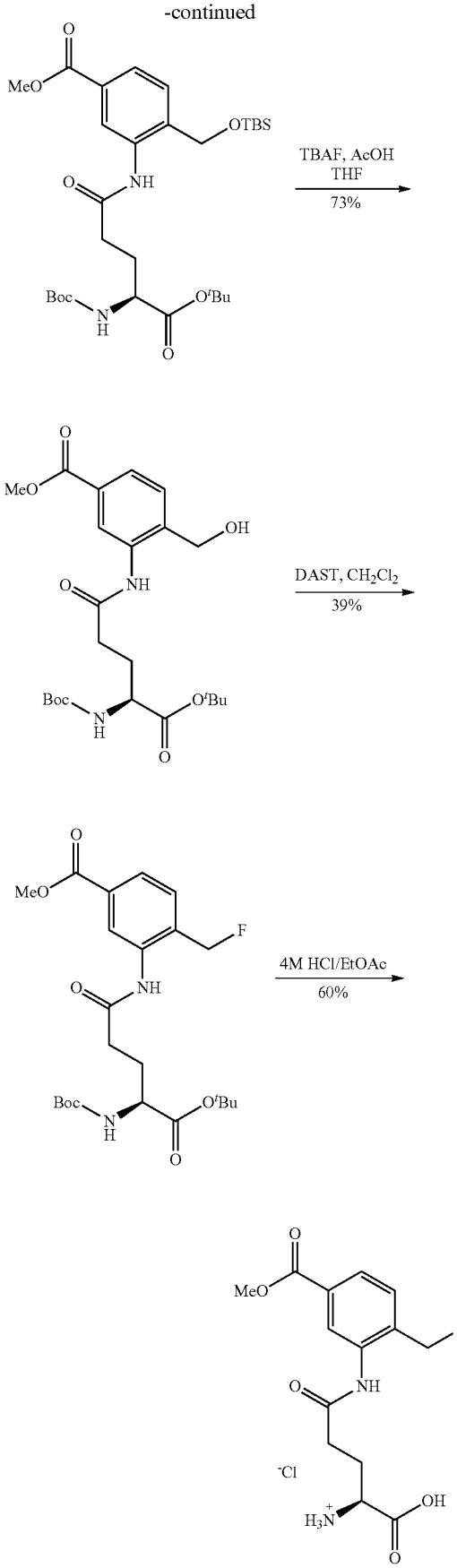

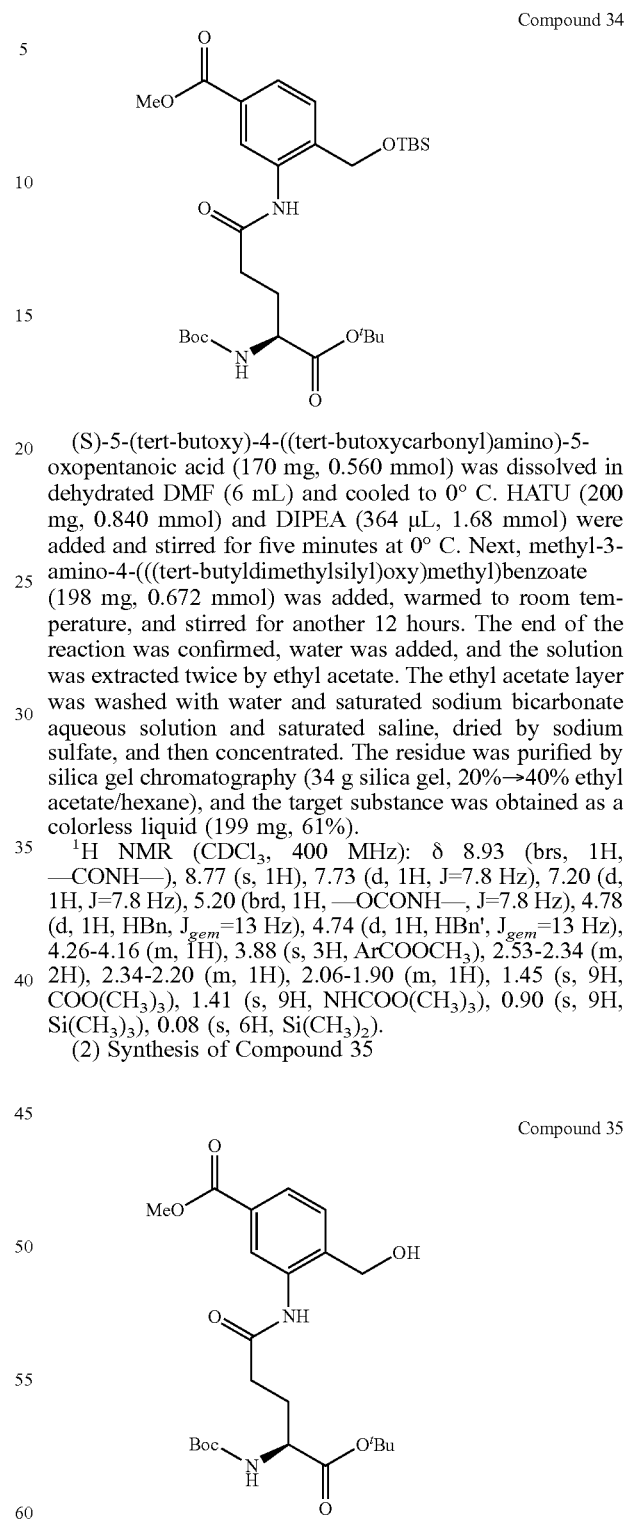

Compound 34

(S)-5-(tert-butoxy)-4-((tert-butoxycarbonyl)amino)-5-oxopentanoic acid (170 mg, 0.560 mmol) was dissolved in dehydrated DMF (6 mL) and cooled to 0° C. HATU (200 mg, 0.840 mmol) and DIPEA (364 μL, 1.68 mmol) were added and stirred for five minutes at 0° C. Next, methyl-3-amino-4-(((tert-butyldimethylsilyl)oxy)methyl)benzoate (198 mg, 0.672 mmol) was added, warmed to room temperature, and stirred for another 12 hours. The end of the reaction was confirmed, water was added, and the solution was extracted twice by ethyl acetate. The ethyl acetate layer was washed with water and saturated sodium bicarbonate aqueous solution and saturated saline, dried by sodium sulfate, and then concentrated. The residue was purified by silica gel chromatography (34 g silica gel, 20%→40% ethyl acetate/hexane), and the target substance was obtained as a colorless liquid (199 mg, 61%).

$^1$H NMR (CDCl$_3$, 400 MHz): δ 8.93 (brs, 1H, —CONH—), 8.77 (s, 1H), 7.73 (d, 1H, J=7.8 Hz), 7.20 (d, 1H, J=7.8 Hz), 5.20 (brd, 1H, —OCONH—, J=7.8 Hz), 4.78 (d, 1H, HBn, J$_{gem}$=13 Hz), 4.74 (d, 1H, HBn', J$_{gem}$=13 Hz), 4.26-4.16 (m, 1H), 3.88 (s, 3H, ArCOOCH$_3$), 2.53-2.34 (m, 2H), 2.34-2.20 (m, 1H), 2.06-1.90 (m, 1H), 1.45 (s, 9H, COO(CH$_3$)$_3$), 1.41 (s, 9H, NHCOO(CH$_3$)$_3$), 0.90 (s, 9H, Si(CH$_3$)$_3$), 0.08 (s, 6H, Si(CH$_3$)$_2$).

(2) Synthesis of Compound 35

Compound 35

Compound 34 (199 mg, 0.343 mmol) was dissolved in dehydrated THF, and TBAF (ca. 1 mol/L in THF, 1.03 mL, 1.03 mmol) and acetic acid (42 μL, 0.687 mmol) were added and stirred for two hours at room temperature. The end of the reaction was confirmed, water was added, and the solution was extracted twice by ethyl acetate. The ethyl acetate layer was washed with water and saturated saline, dried by sodium sulfate, and then concentrated. The residue was purified by silica gel chromatography (34 g silica gel, 40%→60% ethyl acetate/hexane), and the target substance was obtained as a colorless liquid (116 mg, 73%).

$^1$H NMR (CDCl$_3$, 400 MHz): δ 8.96 (brs, 1H, —CONH—), 8.55 (d, 1H, J=8.2 Hz), 7.75 (d, 1H, J=7.8 Hz), 7.29 (d, 1H, J=7.8 Hz), 5.34 (brd, 1H, —OCONH—, J=7.8 Hz), 4.74 (dd, 1H, HBn, J$_{gem}$=13 Hz, J=6.0 Hz), 4.67 (dd, 1H, HBn', J$_{gem}$=13 Hz, J=5.5 Hz), 4.26-4.12 (m, 1H), 3.88 (s, 3H, ArCOOCH$_3$), 3.51 (dd, 1H, CH$_2$OH, J=6.0 Hz, J=5.5 Hz), 2.54-2.38 (m, 2H), 2.34-2.20 (m, 1H), 2.01-1.84 (m, 1H), 1.45 (s, 9H, COO(CH$_3$)$_3$), 1.41 (s, 9H, NHCOO(CH$_3$)$_3$).

(3) Synthesis of Compound 36

Compound 36

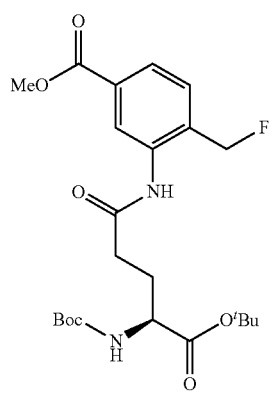

Compound 35 (110 mg, 0.236 mmol) was dissolved in dehydrated dichloromethane (10 mL) and cooled to 0° C. Fluolead® (119 mg, 0.472 mmol) was added and stirred for 1.5 hour. The end of the reaction was confirmed, saturated sodium bicarbonate aqueous solution was added, and the solution was extracted twice by dichloromethane. The dichloromethane layer was washed with saturated sodium bicarbonate aqueous solution and saturated saline, dried by sodium sulfate, and then concentrated. The residue was purified by silica gel chromatography (34 g silica gel, 20%→40% ethyl acetate/hexane), and the target substance was obtained as a colorless liquid (43.6 mg, 39%).

$^1$H NMR (CDCl$_3$, 400 MHz): δ 8.47 (brs, 1H, —CONH—), 8.45 (s, 1H), 7.85 (d, 1H, J=8.2 Hz), 7.43 (d, 1H, J=8.2 Hz), 5.48 (d, 2H, HBn, J$_{HBn-F}$=48 Hz, J$_{gem}$=12 Hz), 5.33 (brd, 1H, —OCONH—, J=7.8 Hz), 4.28-4.17 (m, 1H), 3.90 (s, 3H, ArCOOCH$_3$), 2.57-2.40 (m, 2H), 2.35-2.22 (m, 1H), 1.97-1.82 (m, 1H), 1.45 (s, 9H, COO(CH$_3$), 1.43 (s, 9H, NHCOO(CH$_3$)).

(4) Synthesis of Compound 37

Compound 37

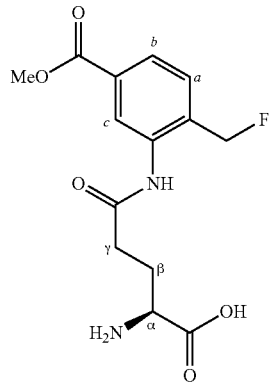

Compound 36 (43.6 mg, 0.0931 mmol) was dissolved in 4M hydrochloric acid/ethyl acetate (10 mL) and stirred for 12 hours at room temperature. The end of the reaction was confirmed, and the reaction solution was concentrated. The residue was purified by reverse-phase HPLC (20%→100% acetonitrile/water), and the target substance was obtained as a white solid (19.4 mg, 60%).

$^1$H NMR (CD$_3$OD, 400 MHz): δ 8.04 (s, 1H, Hc), 7.91 (d, 1H, Hb, J$_{Hb-Ha}$=7.8 Hz), 7.56 (d, 1H, Ha, J$_{Ha-Hb}$=7.8 Hz), 5.44 (d, 2H, HBn, J$_{HBn-F}$=48 Hz), 4.07 (t, 1H, Hα, J$_{Hα-Hβ}$=6.4 Hz), 2.75 (t, 2H, Hγ, J$_{Hγ-Hα}$=7.3 Hz), 2.26 (tt, 2H, Hβ, J$_{Hβ-Hγ}$=7.3 Hz, J$_{Hβ-Hα}$=6.4 Hz); $^{13}$C NMR (CD$_3$OD, 100 MHz): δ 172.0, 170.2, 166.3, 136.5, 134.6, 130.7, 127.8, 126.9, 126.6, 80.7 (d, CH$_2$F, J$_{C-F}$=165 Hz), 52.1, 51.5, 31.1, 25.6; HRMS 313.11879 (M+H$^+$).

Synthesis Example 8

A 5-substituted form was also synthesized according to scheme 8 below.

(Scheme 8)

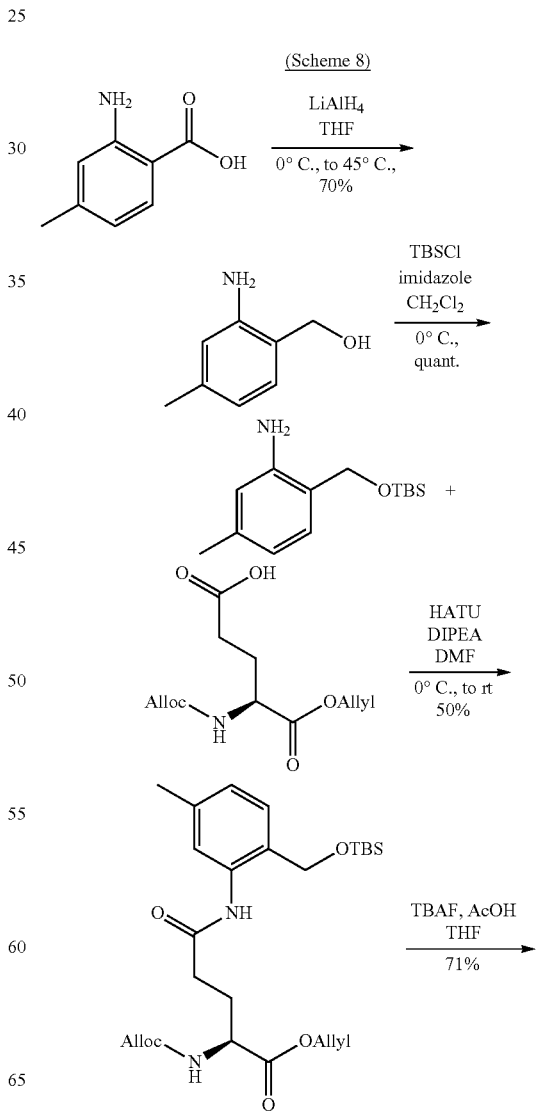

49

-continued

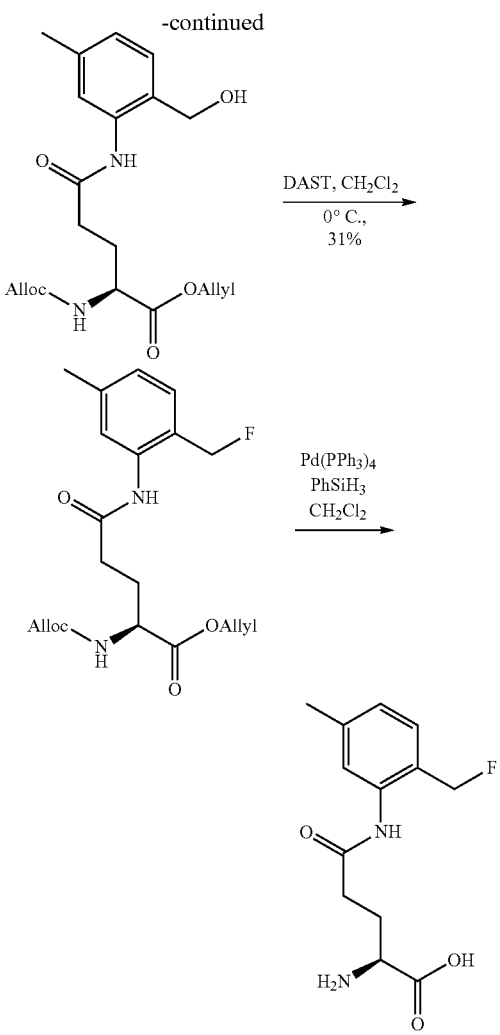

(1) Synthesis of Compound 38

Compound 38

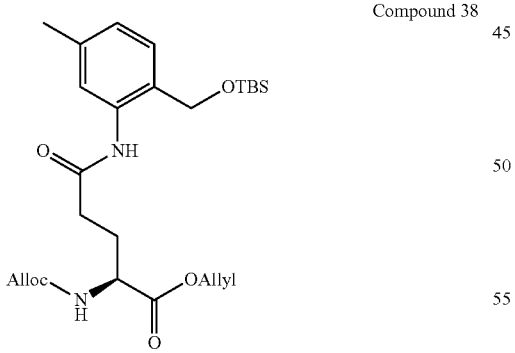

(S)-5-(allyloxy)-4-(((allyloxy)carbonyl)amino)-5-oxopentanoic acid (63.0 mg, 0.232 mmol) was dissolved in dehydrated DMF (5 mL) and cooled to 0° C. HATU (83.0 mg, 0.348 mmol) and DIPEA (151 μL, 0.697 mmol) were added and stirred for five minutes at 0° C. Next, 2-(tert-butyldimethylsilyl)oxy)methyl)-5-methylaniline (70 mg, 0.279 mmol) was added, warmed to room temperature, and stirred for another 12 hours. The end of the reaction was confirmed, water was added, and the solution was extracted twice by ethyl acetate. The ethyl acetate layer was washed with water and saturated sodium bicarbonate aqueous solution and saturated saline, dried by sodium sulfate, and then concentrated. The residue was purified by silica gel chromatography (34 g silica gel, 20%→30% ethyl acetate/hexane), and the target substance was obtained as a colorless liquid (59.0 mg, 50%).

$^1$H NMR (CDCl$_3$, 400 MHz): δ 8.80 (brs, 1H, —CONH—), 7.93 (s, 1H), 6.89 (d, 1H, J=7.6 Hz), 6.76 (d, 1H, J=7.6 Hz), 5.90-5.70 (m, 2H), 5.56 (brd, 1H, —OCONH—, J=8.0 Hz), 5.28-5.10 (m, 4H), 4.62 (s, 2H, HBn), 4.58-4.40 (m, 4H), 4.40-4.30 (m, 1H), 2.51-2.30 (m, 2H), 2.36-2.21 (m, 1H), 2.26 (s, 3H, ArCH$_3$), 2.13-1.95 (m, 1H), 0.83 (s, 9H, Si(CH$_3$)$_3$), 0.00 (s, 6H, Si(CH$_3$)$_2$).

(2) Synthesis of Compound 39

Compound 39

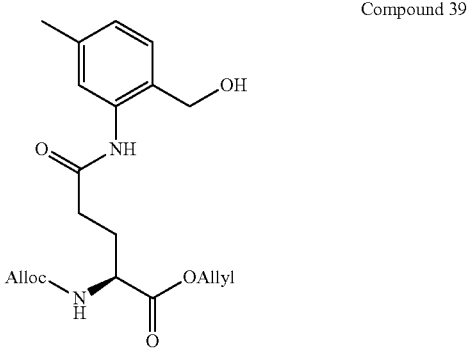

Compound 39 (59.0 mg, 0.117 mmol) was dissolved in dehydrated THF (3 mL), and TBAF (ca. 1 mol/L in THF, 351 μL, 0.351 mmol) and acetic acid (16 μL, 0.234 mmol) were added and stirred for 12 hours at room temperature. The end of the reaction was confirmed, water was added, and the solution was extracted twice by ethyl acetate. The ethyl acetate layer was washed with water and saturated saline, dried by sodium sulfate, and then concentrated. The residue was purified by silica gel chromatography (14 g silica gel, 40%→60% ethyl acetate/hexane), and the target substance was obtained as a colorless liquid (32.6 mg, 71%).

$^1$H NMR (CDCl$_3$, 400 MHz): δ 8.68 (brs, 1H, —CONH—), 7.80 (s, 1H), 7.06 (d, 1H, J=7.8 Hz), 6.88 (d, 1H, J=7.8 Hz), 5.96-5.80 (m, 2H), 5.66 (brd, 1H, —OCONH—, J=7.8 Hz), 5.36-5.14 (m, 4H), 4.71-4.35 (m, 8H), 2.87 (brs, 1H, CH$_2$OH), 2.55-2.41 (m, 2H), 2.39-2.27 (m, 1H), 2.32 (s, 3H, ArCH$_3$), 2.14-1.97 (m, 1H).

(3) Synthesis of Compound 40

Compound 40

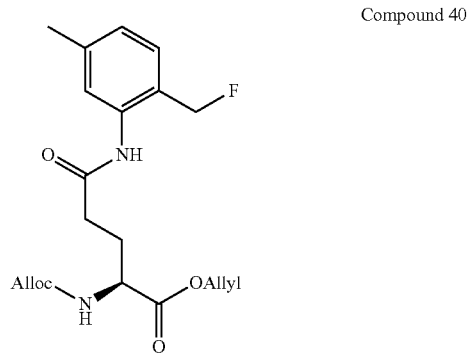

Compound 39 (32.6 mg, 0.0835 mmol) was dissolved in dehydrated dichloromethane (2 mL) and cooled to 0° C. DAST (55 μL, 0.417 mmol) was added and stirred for three hours. The end of the reaction was confirmed, saturated sodium bicarbonate aqueous solution was added, and the solution was extracted twice by ethyl acetate. The ethyl acetate layer was washed with saturated sodium bicarbonate aqueous solution and saturated saline, dried by sodium sulfate, and then concentrated. The residue was purified by silica gel chromatography (14 g silica gel, 20%→40% ethyl acetate/hexane), and the target substance was obtained as a light-yellow liquid (10.3 mg, 31%).

$^1$H NMR (CDCl$_3$, 400 MHz): δ 7.77 (s, 1H), 7.17 (d, 1H, J=7.3 Hz), 6.96 (d, 1H, J=7.3 Hz), 5.97-5.82 (m, 2H), 5.57 (brd, 1H, —OCONH—, J=6.9 Hz), 5.40 (d, 2H, HBn, J$_{HBn-F}$=48 Hz, J$_{gem}$=11 Hz), 5.36-5.17 (m, 4H), 4.65 (d, 2H, J=5.5 Hz), 4.59-4.42 (m, 3H), 2.59-2.42 (m, 2H), 2.45-2.27 (m, 1H), 2.36 (s, 3H, ArCH$_3$), 2.15-2.00 (m, 1H).

(4) Synthesis of Compound 41

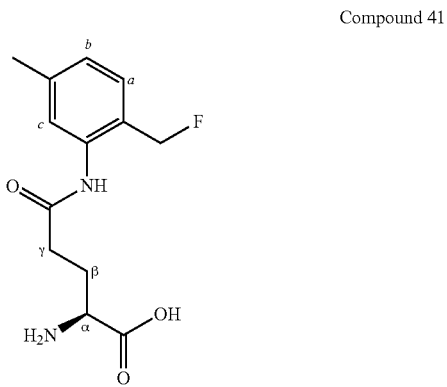 [SMILES: Cc1ccc(CF)c(NC(=O)CC[C@H](N)C(=O)O)c1]

Compound 41

Compound 40 (10.3 mg, 0.0262 mmol) and phenyl silane (33 μL, 0.262 mmol) were dissolved in dehydrated dichloromethane (1 mL), and tetrakis(triphenylphosphine)palladium (7.6 mg, 25 mol %) was added and stirred for one hour at room temperature. The end of the reaction was confirmed, the reaction solution was purified as it was by reverse-phase HPLC (20%→100% acetonitrile/water), and the target substance was obtained as a white solid (3.1 mg, 44%).

$^1$H NMR (CD$_3$OD, 400 MHz): δ 7.31 (d, 1H, Hb, J$_{Hb-Ha}$=7.8 Hz), 7.22 (s, 1H, Hc), 7.09 (d, 1H, Ha, J$_{Ha-Hb}$=7.8 Hz), 5.32 (d, 2H, HBn, J$_{HBn-F}$=48 Hz), 3.65 (t, 1H, Hα, J$_{Hα-Hβ}$=6.0 Hz), 2.71-2.59 (m, 2H, Hγ), 2.32 (s, 3H, ArCH$_3$), 2.23-2.10 (m, 2H, Hβ); $^{13}$C NMR (CD$_3$OD, 100 MHz): δ 172.0, 170.1, 139.4, 134.8, 130.0, 128.7, 127.0, 126.4, 81.1 (d, CH$_2$F, J$_{C-F}$=163 Hz), 52.3, 31.2, 25.7, 19.8; HRMS 291.08980 (M+Na$^+$).

Example 6

In Vitro Efficacy Evaluation of Benzene Ring Substituent-Converted Derivatives

FIG. 14 shows the results of CCK-8 assay of the 4-substituted derivatives. A tendency was seen for derivatives substituted with electron donating groups to show relatively strong antitumor activity.

FIG. 15 shows the results of CCK-8 assay of the 5-substituted derivatives. The effect of the substituent at the 5 position, which is the para position of the leaving group, was stronger than at the 4 position, and the differences in the efficacy of 5-COOMe, 5-H, and 5-Me were more striking. In addition, an efficacy evaluation of the 5-COOMe derivative using low GGT expression cells is shown in the lower part of FIG. 15.

As was demonstrated above, the prodrug-type anticancer agents of the present invention show an antitumor effect by releasing a highly reactive substance (toxic attractant) having an azaquinone methides structure simultaneously with cleavage of the L-glutamic acid portion by GGT on the cancer cell membrane that expresses a high level of GGT. Based on the results of confirming efficacy by coculture imaging using cell lines that express high/low levels of GGT, the prodrug-type anticancer agents of the present invention were able to selectively kill only the high GGT expression cell line without killing the adjacent low GGT expression cells. This result suggests the possibility that the prodrug-type anticancer agents of the present invention will show a wide safety range in vivo as well.

Example 7

Administration Study of gGlu-FMA (Compound 3) in Peritoneal Dissemination Model Mice (1) Pertaining to Peritoneal Dissemination Peritoneal dissemination refers to a state in which tumor cells have been spread and engrafted on the surface of the peritoneum that lines the peritoneum (*1). In clinical practice, stomach cancer, colon cancer, ovarian cancer, etc. often metastasize, and breakthrough treatment methods, including chemotherapy, have not been established.

(2) Model Mouse Creation and Study Outline

Peritoneal dissemination model mice were created by intraperitoneal administration of SHIN3 cells (cancer cell line derived from ovarian cancer, high GGT activity) suspended in PBS. From day seven after cell dissemination, 5 mg/kg of gGlu-FMA or PBS (control) was administered intraperitoneally each day. On day 21 after cell dissemination, gGlu-HMRG was administered intraperitoneally, and the mice were sacrificed ten minutes later. After laparotomy, fluorescence images were acquired by a Maestro in vivo imaging device (FIG. 16).

(3) Results

FIG. 17 shows two examples of macro images and fluorescence images of the mesentery of mice administered PBS and gGlu-FMA. Tumors appear to be decreased overall in the mice administered gGlu-FMA in both the macro and fluorescence images.

INDUSTRIAL APPLICABILITY

The prodrug-type anticancer agents of the present invention are expected to serve as innovative clinical drugs that can recognize differences in the metabolic enzyme activity of two adjacent cells and kill only the cancer cells having enhanced enzyme activity and that can improve upon major problems with cancer chemotherapy such as reduction of a patient's QOL due to serious side effects. Furthermore, the azaquinone methides release-type prodrugs of the present invention which do not use existing anticancer agents can be synthesized easily, which is expected to make a significant contribution to the development costs. Thus, the prodrugs developed will be highly valuable from a medical and economic standpoint as well as industrial utility.

The invention claimed is:

1. A compound represented by general formula (I) or a salt thereof,

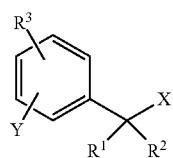

(I)

wherein
- X is selected from the group consisting of a fluorine atom, ester group (—OC(═O)—R'), and carbamate group (—OCONH—R'),
  where R' is selected from unsubstituted alkyl groups or substituted or unsubstituted aryl groups;
- Y is —NH—CO-L, —NH-L', or —OL',
  where L, together with the C═O to which L bonds, constitutes an amino acid residue or a peptide,
  L' is a saccharide or a partial structure of a saccharide, or a saccharide or partial structure of a saccharide having a self-cleaving linker, an amino acid or a peptide having a self-cleaving linker, wherein the partial structure of the saccharide is a saccharide in which a hydroxyl group is lacking, and wherein —Y bonds to —C(R$^1$)(R$^2$)X on the ortho position or para position of the benzene ring;
- R$^1$ and R$^2$ are each a hydrogen atom;
- R$^3$ represents a hydrogen atom or one to four monovalent substituents present on a benzene ring, which are the same or different, wherein the monovalent substituent of R$^3$ is an alkyl group, OR", OCOR", or a halogen atom, wherein R" is a substituted or unsubstituted alkyl group or a substituted or unsubstituted aryl group.

2. The compound or a salt thereof according to claim 1, wherein the saccharide is β-D-galactose.

3. The compound or salt thereof according to claim 1, wherein Y has a structure selected from the following:

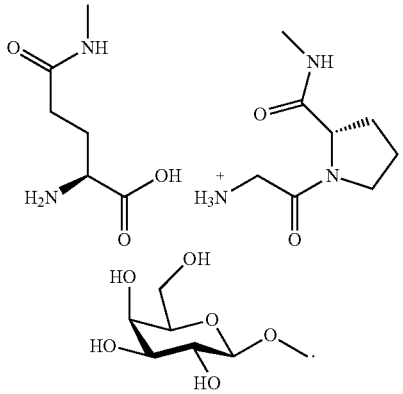

4. The compound or a salt thereof according to claim 1, wherein the monovalent substituent of R$^3$ is a methyl group or a methoxycarbonyl group.

\* \* \* \* \*